(12) United States Patent
Tamatani et al.

(10) Patent No.: US 7,932,358 B2
(45) Date of Patent: Apr. 26, 2011

(54) ANTIBODIES TO JTT-1 PROTEIN AND CELLS SECRETING SUCH ANTIBODIES

(75) Inventors: Takuya Tamatani, Kanagawa (JP); Katsunari Tezuka, Kanagawa (JP)

(73) Assignee: Japan Tobacco Inc., Tokyo (JP)

( * ) Notice: Subject to any disclaimer, the term of this patent is extended or adjusted under 35 U.S.C. 154(b) by 35 days.

(21) Appl. No.: 11/938,753

(22) Filed: Nov. 12, 2007

(65) Prior Publication Data

US 2008/0248031 A1 Oct. 9, 2008

Related U.S. Application Data

(60) Continuation of application No. 10/721,404, filed on Nov. 25, 2003, now Pat. No. 7,294,473, which is a continuation of application No. 10/301,056, filed on Nov. 21, 2002, now abandoned, which is a division of application No. 09/383,551, filed on Aug. 26, 1999, now Pat. No. 7,030,225, which is a continuation-in-part of application No. PCT/JP98/00837, filed on Feb. 27, 1998.

(30) Foreign Application Priority Data

Feb. 27, 1997 (JP) ...................................... 9-062290
Feb. 26, 1998 (JP) ...................................... 10-062217

(51) Int. Cl.
*C07K 16/00* (2006.01)
*A61K 39/395* (2006.01)
*C12N 5/10* (2006.01)

(52) U.S. Cl. ................... 530/387.1; 424/130.1; 435/70.1

(58) Field of Classification Search ........................ None
See application file for complete search history.

(56) References Cited

U.S. PATENT DOCUMENTS

| | | | |
|---|---|---|---|
| 5,484,892 A | 1/1996 | Tedder et al. |
| 5,506,126 A | 4/1996 | Seed et al. |
| 5,521,288 A | 5/1996 | Linsley et al. |
| 5,770,197 A | 6/1998 | Linsley et al. |
| 5,914,112 A | 6/1999 | Bednar et al. |
| 6,075,181 A | 6/2000 | Kucherlapati et al. |
| 6,803,039 B2 | 10/2004 | Tsuji et al. |
| 7,030,225 B1 | 4/2006 | Tamatani et al. |
| 7,045,615 B2 | 5/2006 | Tamatani et al. |
| 7,112,655 B1 | 9/2006 | Tamatani et al. |
| 7,125,551 B2 | 10/2006 | Kroczek |
| 7,132,099 B2 | 11/2006 | Kroczek |
| 7,166,283 B2 | 1/2007 | Tsuji et al. |
| 7,196,175 B2 | 3/2007 | Tamatani et al. |
| 7,217,792 B2 | 5/2007 | Tamatani et al. |
| 7,226,909 B2 | 6/2007 | Tamatani et al. |
| 7,247,612 B2 | 7/2007 | Tamatani et al. |
| 7,259,147 B2 | 8/2007 | Tamatani et al. |
| 7,259,247 B1 | 8/2007 | Kroczek |
| 7,279,560 B2 | 10/2007 | Tamatani et al. |
| 7,294,473 B2 | 11/2007 | Tamatani et al. |
| 7,306,800 B2 | 12/2007 | Kroczek |
| 2002/0164697 A1 | 11/2002 | Coyle et al. |
| 2004/0131608 A1 | 7/2004 | Watanabe |
| 2004/0229790 A1 | 11/2004 | Tezuka et al. |
| 2004/0253229 A1 | 12/2004 | Suzuki et al. |
| 2008/0199466 A1* | 8/2008 | Tsuji et al. .................. 424/134.1 |

FOREIGN PATENT DOCUMENTS

| | | |
|---|---|---|
| AU | 13320/99 | 4/1999 |
| DE | 19821060 | 4/1999 |
| EP | 0 984 023 | 3/2000 |
| EP | 1 125 585 | 8/2001 |
| JP | 11-228442 | 8/1999 |
| JP | 2000-154151 | 6/2000 |
| WO | WO 95/33770 | 12/1995 |
| WO | WO 97/26912 | 7/1997 |
| WO | WO 98/11909 | 3/1998 |
| WO | WO 98/19706 | 5/1998 |
| WO | WO 98/37415 | 8/1998 |
| WO | WO 98/38216 | 9/1998 |
| WO | WO 98/45331 | 10/1998 |
| WO | WO 00/19988 | 4/2000 |
| WO | WO 00/46240 | 8/2000 |
| WO | WO 00/67788 | 11/2000 |
| WO | WO 01/08700 | 2/2001 |
| WO | WO 01/12658 | 2/2001 |
| WO | WO 01/15732 | 3/2001 |
| WO | WO 01/18022 | 3/2001 |
| WO | WO 01/21796 | 3/2001 |
| WO | WO 01/32675 | 5/2001 |
| WO | WO 01/64704 | 9/2001 |
| WO | WO 01/87981 | 11/2001 |
| WO | WO 02/44364 | 6/2002 |
| WO | WO 02/070010 | 9/2002 |
| WO | WO 02/076504 | 10/2002 |

OTHER PUBLICATIONS

Blazar, BR et al., J. Immunol. 1996, 157(8):3250-9.
Finck, BK et al., Science 1994, 125:1225-7.
Kaneko, H. et al., Nippon Rinsho. 1997, 55 Suppl. 6:215-220.
Mohler, KM et al., J. Immunol. 1993, 151(3):1548-61.
Moreland, LW et al., J. Rheumatol. 1996, 23(11):1849-55. Vidric, M. et al., Infect. Immun. 2006, 74(2):1050-61.
Aicher et al., "Characterization of Human Inducible Costimulator Ligand Expression and Function," J. Immunol., 164(9):4689-4696 (2000).
Bajorath "A molecular model of inducible costimulator protein and three-dimensional analysis of its relation to the CD28 family of T cell-specific costimulatory receptors," J. Mol. Model. 5:169-176 (1999).
Beier et al., "Induction, binding specificity and function of human ICOS," Eur. J. Immunol., 30(12):3707-3717 (2000).
Bensimon et al., "Human lupus anti-DNA autoantibodies undergo essentially primary V kappa gene rearrangements," EMBO J. 13(13):2951-62 (1994).

(Continued)

*Primary Examiner* — Ilia Ouspenski
(74) *Attorney, Agent, or Firm* — Fish & Richardson P.C.

(57) ABSTRACT

Novel cell surface molecules recognized by monoclonal antibodies against a cell surface molecule of lymphocytic cells that play an important role in autoimmune diseases and allergic diseases have been isolated, identified, and analyzed for their functions. The cell surface molecules are expressed specifically in thymocytes, lymphocytes activated by ConA-stimulation, and peripheral blood lymphocytes, and induce cell adhesion. Antibodies against the cell surface molecules significantly ameliorate pathological conditions of autoimmune diseases and allergic diseases.

26 Claims, 21 Drawing Sheets

OTHER PUBLICATIONS

Brodie et al., "LICOS, a primordial costimulatory ligand?" Current Biology, 10(6):333-336 (2000).

Buonfiglio et al., "Characterization of a novel human surface molecule selectively expressed by mature thymocytes, activated T cells and subsets of T cell lymphomas," Eur. J. Immunol., 29(9)2863-2874 (1999).

Buonfiglio et al. "The T cell activation molecule H4 and the CD28-like molecule ICOS are identical," Eur. J. Immunol., 30:3463-3467 (2000).

Cameron "Recent advances in transgenic technology" Molecular Biotechnology 7:253-65 (1997).

Chambers, "The expanding world of co-stimulation: the two-signal model revisited," Trends in Immunology, 22(4):217-223 (2001).

Cocks et al. "A novel receptor involved in T-cell activation," Nature, 376:260-263 (Jul. 20, 1995).

Coyle et al., "The CD28-Related Molecule ICOS Is Required for Effective T Cell-Dependent Immune Responses," Immunity, 13:95-105, (2000).

Dong et al., "Cutting Edge: Critical Role of Inducible Costimulator in Germinal Center Reactions," J. Immunol., 166(6):3659-3662 (2001).

Dong, "ICOS co-stimulatory receptor is essential for T-cell activation and function," Nature 409(6816):97-101 (2001).

Goding, "Monoclonal Antibodies: Principles and Practice," $2^{nd}$ Edition, Academic Press, Orlando, Florida, Chapter 8, pp. 281-293 (1986).

Goni et al., "Structural and idiotypic characterization of the L chains of human IgM autoantibodies with different specificities," J. Immunol. 142(9):3158-63 (1989).

Gonzalo et al., "The Related Molecules CD28 and Inducible Costimulator Deliver Both Unique and Complementary Signals Required for Optimal T Cell Activation," J. Immunol., 166(1):1-5 (2001).

Guo et al., "Stimulatory Effects of B7-Related Protein-1 on Cellular and Humoral Immune Responses in Mice," J. Immunol., 166(9):5578-5584 (2001).

Harlow and Lane, "Antibodies: A Laboratory Manual," Cold Spring Harbor Laboratory, p. 285 (1988).

Hanzawa et al., "Characteristics of a TTH1 antibody which blocks an unknown adhesion phenomenon," Proceedings of the Japanese Society for Immunology, vol. 24, Abstract No. W17-13 (1994) [Original Japanese and English Language Translation].

Heyeck et al. "Developmental regulation of a murine T-cell-specific tyrosine kinase gene, Tsk," Proc. Natl. Acad. Sci. USA, vol. 90, pp. 669-673 (1993).

Houdebine "Production of pharmaceutical proteins from transgenic animals" J. Biotechnol. 34:269-87 (1994).

Hutloff et al. "ICOS is an inducible T-cell co-stimulator structurally and functionally related to CD28," Nature 397:263-266 (1999).

Iiyama et al., "The role of inducible co-stimulator (ICOS)/B7-related protein-1 (B7RP-1) interaction in the functional development of Peyer's patches," Immunology Letters, In Press, Uncorrected Proof available online Apr. 11, 2003, http://www.sciencedirect.com/science/journal/01652478.

Ishikawa et al., "Prediction of the Coding Sequences of Unidentified Human Genes. X. The Complete Sequences of 100 New cDNA Clones from Brain Which Can Code for Large Proteins in vitro," DNA Research, 5:169-176 (1998).

Kappel et al. "Regulating gene expression in transgenic animals" Current Opinion in Biotechnology 3:548-53 (1992).

Kopf et al., "Inducible Costimulator Protein (ICOS) Controls T Helper Cell Subset Polarization after Virus and Parasite Infection," J. Exp. Med., 192(1):53-61 (2000).

Kuchroo et al. "B7-1 and B7-2 costimulatory molecules activate differentially the Th1/Th2 developmental pathways: Application to autoimmune disease therapy," Cell, 80:707-718 (Mar. 10, 1995).

Ling et al., "Identification of GL50, a Novel B7-Like Protein That Functionally Binds to ICOS Receptor," J. Immunol., 164(4):1653-1657 (2000).

Mages et al. "Molecular cloning and characterization of murine ICOS and identification of B7h as ICOS ligand," Eur. J. Immunol. 30:1040-1047 (2000).

Marguet et al. "cDNA Cloning for Mouse Thymocyte-activating Molecule," The Journal of Biological Chemistry, vol. 267, No. 4, pp. 2200-2208 (1992).

McAdam, "ICOS is critical for CD40-mediated antibody class switching," Nature 409(6816):102-105 (2001).

McAdam, "Mouse Inducible Costimulatory Molecule (ICOS) Expression Is Enhanced by CD28 Costimulation and Regulates Differentiation of $CD4_+T$ Cells," J. Immunol., 165(9):5035-5040 (2000).

McAdam et al., "Mouse inducible costimulatory (ICOS) molecule expression is increased by CD28 costimulation and regulates development of Th2 cells," FASEB Journal, 14(6):A1169 (2000).

Mueller, "T cells: A proliferation of costimulatory molecules," Curr. Biol. 10(6):R227-R230 (2000).

Mullins et al. "Expression of the DBA/2J Ren-2 gene in the adrenal gland of transgenic mice" EMBO J., 8:4065-72 (1989).

Mullins et al. "Fulminant hypertension in transgenic rats harbouring the mouse Ren-2 gene" Nature, 344:541-44 (1990).

Mullins et al. "Transgenesis in nonmurine species" Hypertension 22:630-33 (1993).

Niemann "Transgenic farm animals get off the ground" Transgenic Research, 7:73-75 (1998).

Nojima et al. "The 4F9 antigen is a member of the tetra spans transmembrane protein family and functions as an accessory molecule in T cell activation and adhesion," Cellular Immunology, 152:249-260 (1993).

Nurieva et al., "Inducible costimulator is essential for collagen-induced arthritis," J. Clin. Invest. 111 (5):701-06 (2003).

Overbeek "Factors affecting transgenic animal production," Transgenic Animal Technology, A Laboratory Handbook 96-98 (1994).

Özkaynak et al., "Importance of ICOS-B7RP-1 costimulation in acute and chronic allograft rejection," Nature Immunology 2(7):591-596 (2001).

Pech et al., "A large section of the gene locus encoding human immunoglobulin variable regions of the kappa type is duplicated," J. Mol Biol. 183(3):291-9 (1985).

Poster, Kyoto International Conference Hall, Takaragaike Sakyo-ku, Kyoto, Japan (Nov. 30, 1994) [Original Japanese and English Language Translation].

Redoglia et al. "Characterization of H4: a mouse T lymphocyte activation molecule functionally associated with the CD3/T cell receptor," Eur. J. Immunol., 26:2781-2789 (1996).

Riley et al., "ICOS Costimulation Requires IL-2 and Can Be Presented by CTLA-4 Engagement," J. Immunol., 166(8):4943-4948 (2001).

Robert et al. "Antibody Cross-Linking of the Thymocyte-Specific Cell Surface Molecule CTX Causes Abnormal Mitosis and Multinucleation of Tumor Cells," Experimental Cell Research, 235:227-237 (1997).

Sakamoto et al., "AILIM/ICOS: its expression and functional analysis with monoclonal antibodies," Hybridoma and Hybridomics, 20(5):293-303 (2001).

Sato et al. (2000) "Up-regulation of inducible co-stimulator (ICOS) expression and its regulation of cytokine production in inflammatory bowel disease," Gastroenterology, 118(4):A662.

Sharpe "Analysis of lymphocyte costimulation in vivo using transgenic and 'knockout' mice," Current Opinion in Immunology, 7:389-395 (1995).

Sigmund "Are studies in genetically altered mice out of control?" Arterioscler. Thromb. Vasc. Biol., 20:1425-29 (2000).

Swallow et al., "B7h, a Novel Costimulatory Homolog of B7.1 and B7.2, Is Induced by TNFα," Immunity, 11:423-432, (1999).

Tafuri et al., "ICOS is essential for effective T-helper-cell responses," Nature 409(6816):105-109 (2001).

Tai et al. "A role for CD9 molecules in T cell activation," J. Exp. Med., 184:753-758 (Aug. 1996).

Tamatani et al., "Characteristics of an antibody which induces an ICAM-1-LFA-1-independent adhesion pathway," Proceedings of the Japanese Society for Immunology, vol. 23, Abstract No. H-160 (1993) [Original Japanese and English Language Translation].

Tamatani et al. "AILIM/ICOS: a novel lymphocyte adhesion molecule," International Immunology, 12(1):51-55 (2000).

Tezuka et al., "Genetic cloning of a lymphocyte surface signal transduction molecule which induces an unknown adhesion phenomenon," Proceedings of the Japanese Society for Immunology, vol. 24, Abstract No. W17-14 (1994) [Original Japanese and English Language Translation].

Tezuka et al. "Identification and characterization of rat AILIM/ICOS, a novel T-cell costimulatory molecule, related to the CD28/CTLA4 family," Biochemical and Biophysical Research Communications, 276:335-345 (2000).

Tomlinson et al., "The repertoire of human germline VH sequences reveals about fifty groups of VH segments with different hypervariable loops," J. Mol. Biol. 227(3):776-98 (1992).

Wall "Transgenic livestock: progress and prospects for the future" Theriogenology 45:57-68 (1996).

Wang et al., "Costimulation of T cells by B7-H2, a B7-like molecule that binds ICOS," Blood, 96(8):2808-2813 (2000).

Yoshinaga et al., "T-cell co-stimulation through B7RP-1 and ICOS," Nature, 402:827-832 (1999).

Yoshinaga et al., "Characterization of a new human B7-related protein: B7RP-1 is the ligand to the co-stimulatory protein ICOS," International Immunology, 12(10):1439-1441 (2000).

Carlesso et al., "Depletion of inducible co-stimulator (ICOS) bearing T cells inhibits expansion of T follicular helper cells ($T_{FH}$) and prevents disease in a graft versus host mouse model of scleroderma" Poster Presentation, American College of Rheumatology, 2009 Annual Scientific Meeting, Oct. 19, 2009.

Mittereder et al., "ICOS is critical for follicular helper T cells ($T_{FH}$)-mediated maintenance of germinal center B cells in non human primates" Poster Presentation, American College of Rheumatology, 2008 Annual Scientific Meeting, Oct. 28, 2008.

Mittereder, "ICOS is critical for T follicular helper cell-mediated maintenance of germinal center B cells in non-human primates" FASEB Summer Research Conference—Autoimmunity, Jul. 2, 2009.

Taylor et al. "Unraveling Functions of ICOS Bearing T Cells: New Insights about Treating Autoimmune Disorders" Poster Presentation, Keystone Symposia on Tolerance and Autoimmunity, Feb. 21-26, 2010.

Carlesso et al., "Targeted depletion of inducible co-stimulator (ICOS) bearing T cells prevents disease in a graft versus host model of scleroderma" Poster Presentation, $9^{th}$ International Conference on Systemic Lupus Erythematosus, Jun. 25, 2010.

Cook et al., "The human immunoglobulin $V_H$ repertoire," *Immunology Today* (1995) 16(5):237-42.

Faggioni et al., "Determination of the minimum anticipated biological level (MABEL) for an ADCC-enhanced inducible co-stimulator (ICOS) monoclonal antibody for the treatment of autoimmune diseases" Poster Presentation, Annual Congress of the European League Against Rheumatism, Jun. 2010.

Ghosh et al. "Ulcerative colitis" (2000) BMJ. 320(7242):1119-23.

Hanauer et al. "Management of Crohn's disease in adults" (2001) Am J Gastroenterol. 96(3):635-43.

Koh et al., "A screening method of SH2 domain ligands and blockers using a solid phase binding" (1997) Cancer Lett. 120(1):1-7.

Mendez et al. "Functional transplant of megabase human immunoglobulin loci recapitulates human antibody response in mice" (1997) Nat Genet. 15(2):146-56.

Soderlind et al., "Domain libraries: Synthetic diversity for de novo design of antibody V-regions," *Gene* (1995) 160(2):269-72.

Takai et al. "Epitope analysis and primary structures of variable regions of anti-human FcepsilonRl monoclonal antibodies, and expression of the chimeric antibodies fused with human constant regions" Biosci Biotechnol Biochem . (2000) 64(9):1856-67.

van der Merwe et al., "CD80 (B7-1) binds both CD28 and CTLA-4 with a low affinity and very fast kinetics," *Journal of Experimental Medicine* (1997) 185(3):393-403.

* cited by examiner

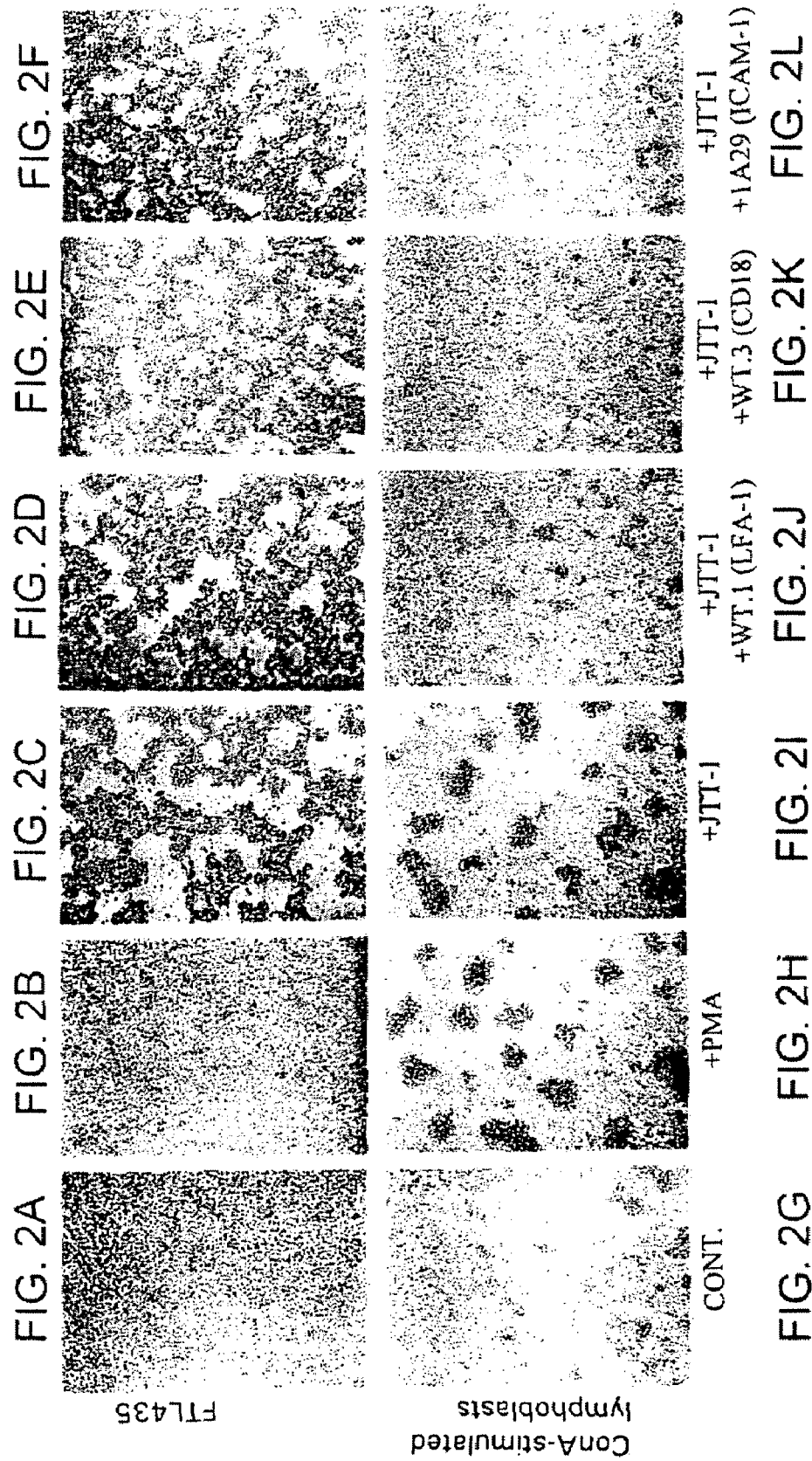

```
rat          MKPYFSCVFV FCFLIKLLTG ELNDLANHRM FSFHDGGVQI SCNYPETVQQ    50
rat mutant   MKPYFSCVFV FCFLIKLLTG ELNDLANHRM FSFHDGGVQI SCNYPETVQQ    50
consensus    MKPYFSCVFV FCFLIKLLTG ELNDLANHRM FSFHDGGVQI SCNYPETVQQ    50 rat          LKMQLFKDRE VLCDLTKTKG SGNTVSIKNP MSCPYQLSNN SVSFFLDNAD   100
rat mutant   LKMQLFKDRE VLCDLTKTKG SGNTVSIKNP MSCPYQLSNN SVSFFLDNAD   100
consensus    LKMQLFKDRE VLCDLTKTKG SGNTVSIKNP MSCPYQLSNN SVSFFLDNAD   100 rat          SSQGSYFLCS LSIFDPPPFQ EKNLSGGYLL IYESQLCCQL KLWLPVGCAA   150
rat mutant   SSQGSYFLCS LSIFDPPPFQ EKNLSGGYLL IYESQLCCQL KLWLPVGCAA   150
consensus    SSQGSYFLCS LSIFDPPPFQ EKNLSGGYLL IYESQLCCQL KLWLPVGCAA   150 rat          FVAALLFGCI FIWFAKKKY RSSVHDPNSE YMFMAAVNTN KKSRLAG MTS     200
rat mutant   FVAALLFGCI FIWFAKKKY RSSVHDPNSE YMFMAAVNTN KKSRLAG TAP     200
consensus    FVAALLFGCI FIWFAKKKY RSSVHDPNSE YMFMAAVNTN KKSRLAG ...     200 rat          ---------- ------                                         200
rat mutant   LRALGRGEHS SCQDRN                                        216
consensus    .......... ......                                        216
```

FIG. 14

SEQUENCE LISTING

<160> NUMBER OF SEQ ID NOS: 26

<210> SEQ ID NO 1
<211> LENGTH: 600

```
<212> TYPE: DNA
<213> ORGANISM: Homo sapiens
<220> FEATURE:
<221> NAME/KEY: CDS
<222> LOCATION: (1)...(597)

<400> SEQUENCE: 1 atg aag tca ggc ctc tgg tat ttc ttt ctc ttc tgc ttg cgc att aaa      48
Met Lys Ser Gly Leu Trp Tyr Phe Phe Leu Phe Cys Leu Arg Ile Lys
1               5                   10                  15 gtt tta aca gga gaa atc aat ggt tct gcc aat tat gag atg ttt ata      96
Val Leu Thr Gly Glu Ile Asn Gly Ser Ala Asn Tyr Glu Met Phe Ile
            20                  25                  30 ttt cac aac gga ggt gta caa att tta tgc aaa tat cct gac att gtc     144
Phe His Asn Gly Gly Val Gln Ile Leu Cys Lys Tyr Pro Asp Ile Val
        35                  40                  45 cag caa ttt aaa atg cag ttg ctg aaa ggg ggg caa ata ctc tgc gat     192
Gln Gln Phe Lys Met Gln Leu Leu Lys Gly Gly Gln Ile Leu Cys Asp
    50                  55                  60 ctc act aag aca aaa gga agt gga aac aca gtg tcc att aag agt ctg     240
Leu Thr Lys Thr Lys Gly Ser Gly Asn Thr Val Ser Ile Lys Ser Leu
65                  70                  75                  80 aaa ttc tgc cat tct cag tta tcc aac aac agt gtc tct ttt ttt cta     288
Lys Phe Cys His Ser Gln Leu Ser Asn Asn Ser Val Ser Phe Phe Leu
                85                  90                  95 tac aac ttg gac cat tct cat gcc aac tat tac ttc tgc aac cta tca     336
Tyr Asn Leu Asp His Ser His Ala Asn Tyr Tyr Phe Cys Asn Leu Ser
            100                 105                 110 att ttt gat cct cct cct ttt aaa gta act ctt aca gga gga tat ttg     384
Ile Phe Asp Pro Pro Pro Phe Lys Val Thr Leu Thr Gly Gly Tyr Leu
        115                 120                 125 cat att tat gaa tca caa ctt tgt tgc cag ctg aag ttc tgg tta ccc     432
His Ile Tyr Glu Ser Gln Leu Cys Cys Gln Leu Lys Phe Trp Leu Pro
    130                 135                 140 ata gga tgt gca gcc ttt gtt gta gtc tgc att ttg gga tgc ata ctt     480
Ile Gly Cys Ala Ala Phe Val Val Val Cys Ile Leu Gly Cys Ile Leu
145                 150                 155                 160 att tgt tgg ctt aca aaa aag aag tat tca tcc agt gtg cac gac cct     528
Ile Cys Trp Leu Thr Lys Lys Lys Tyr Ser Ser Ser Val His Asp Pro
                165                 170                 175 aac ggt gaa tac atg ttc atg aga gca gtg aac aca gcc aaa aaa tct     576
Asn Gly Glu Tyr Met Phe Met Arg Ala Val Asn Thr Ala Lys Lys Ser
            180                 185                 190 aga ctc aca gat gtg acc cta taa                                     600
Arg Leu Thr Asp Val Thr Leu
        195

<210> SEQ ID NO 2
<211> LENGTH: 199
<212> TYPE: PRT
<213> ORGANISM: Homo sapiens

<400> SEQUENCE: 2

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60
```

```
Leu Thr Lys Thr Lys Gly Ser Gly Asn Thr Val Ser Ile Lys Ser Leu
 65                  70                  75                  80

Lys Phe Cys His Ser Gln Leu Ser Asn Asn Ser Val Ser Phe Phe Leu
                 85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Val His Asp Pro
            165                 170                 175

Asn Gly Glu Tyr Met Phe Met Arg Ala Val Asn Thr Ala Lys Lys Ser
        180                 185                 190

Arg Leu Thr Asp Val Thr Leu
        195
```

```
<210> SEQ ID NO 3
<211> LENGTH: 2610
<212> TYPE: DNA
<213> ORGANISM: Homo sapiens
<220> FEATURE:
<221> NAME/KEY: CDS
<222> LOCATION: (26)...(622)

<400> SEQUENCE: 3
```

```
ggactgttaa ctgtttctgg caaac atg aag tca ggc ctc tgg tat ttc ttt        52
                            Met Lys Ser Gly Leu Trp Tyr Phe Phe
                             1               5 ctc ttc tgc ttg cgc att aaa gtt tta aca gga gaa atc aat ggt tct       100
Leu Phe Cys Leu Arg Ile Lys Val Leu Thr Gly Glu Ile Asn Gly Ser
 10              15                  20                  25 gcc aat tat gag atg ttt ata ttt cac aac gga ggt gta caa att tta       148
Ala Asn Tyr Glu Met Phe Ile Phe His Asn Gly Gly Val Gln Ile Leu
             30                  35                  40 tgc aaa tat cct gac att gtc cag caa ttt aaa atg cag ttg ctg aaa       196
Cys Lys Tyr Pro Asp Ile Val Gln Gln Phe Lys Met Gln Leu Leu Lys
         45                  50                  55 ggg ggg caa ata ctc tgc gat ctc act aag aca aaa gga agt gga aac       244
Gly Gly Gln Ile Leu Cys Asp Leu Thr Lys Thr Lys Gly Ser Gly Asn
     60                  65                  70 aca gtg tcc att aag agt ctg aaa ttc tgc cat tct cag tta tcc aac       292
Thr Val Ser Ile Lys Ser Leu Lys Phe Cys His Ser Gln Leu Ser Asn
 75                  80                  85 aac agt gtc tct ttt ttt cta tac aac ttg gac cat tct cat gcc aac       340
Asn Ser Val Ser Phe Phe Leu Tyr Asn Leu Asp His Ser His Ala Asn
 90                  95                 100                 105 tat tac ttc tgc aac cta tca att ttt gat cct cct cct ttt aaa gta       388
Tyr Tyr Phe Cys Asn Leu Ser Ile Phe Asp Pro Pro Pro Phe Lys Val
            110                 115                 120 act ctt aca gga gga tat ttg cat att tat gaa tca caa ctt tgt tgc       436
Thr Leu Thr Gly Gly Tyr Leu His Ile Tyr Glu Ser Gln Leu Cys Cys
        125                 130                 135 cag ctg aag ttc tgg tta ccc ata gga tgt gca gcc ttt gtt gta gtc       484
Gln Leu Lys Phe Trp Leu Pro Ile Gly Cys Ala Ala Phe Val Val Val
    140                 145                 150 tgc att ttg gga tgc ata ctt att tgt tgg ctt aca aaa aag aag tat       532
Cys Ile Leu Gly Cys Ile Leu Ile Cys Trp Leu Thr Lys Lys Lys Tyr
```

```
                 155                 160                 165
tca tcc agt gtg cac gac cct aac ggt gaa tac atg ttc atg aga gca   580
Ser Ser Ser Val His Asp Pro Asn Gly Glu Tyr Met Phe Met Arg Ala
170                 175                 180                 185 gtg aac aca gcc aaa aaa tct aga ctc aca gat gtg acc cta           622
Val Asn Thr Ala Lys Lys Ser Arg Leu Thr Asp Val Thr Leu
                190                 195 taatatggaa ctctggcacc caggcatgaa gcacgttggc cagttttcct caacttgaag  682
tgcaagattc tcttatttcc gggaccacgg agagtctgac ttaactacat acatcttctg  742
ctggtgtttt gttcaatctg gaagaatgac tgtatcagtc aatggggatt ttaacagact  802
gccttggtac tgccgagtcc tctcaaaaca acaccctct tgcaaccagc tttggagaaa   862
gcccagctcc tgtgtgctca ctgggagtgg aatccctgtc tccacatctg ctcctagcag  922
tgcatcagcc agtaaaacaa acacatttac aagaaaaatg ttttaaagat gccaggggta  982
ctgaatctgc aaagcaaatg agcagccaag gaccagcatc tgtccgcatt tcactatcat  1042
actacctctt ctttctgtag ggrtgagaat tcctctttta atcagtcaag ggagatgctt  1102
caaagctggr gctattttat ttctgagatg ttgatgtgaa ctgtacatta gtacatactc  1162
agtactctcc ttcaattgct gaaccccagt tgaccatttt accaagactt tagatgcttt  1222
cttgtgccct caattttctt tttaaaaata cttctacatg actgcttgac agcccaacag  1282
ccactctcaa tagagagcta tgtcttacat tctttcctct gctgctcaat agttttatat  1342
atctatgcat acatatatac acacatatgt atataaaatt cataatgaat atatttgcct  1402
atattctccc tacaagaata ttttgctcc agaaagacat gttctttct caaattcagt    1462 taaaatggtt tactttgttc aagttagtgg taggaaacat tgcccggaat tgaaagcaaa  1522
tttawwttat tatcctattt tctaccatta tctatgtttt catggtgcta ttaattacaa  1582
gtttagttct ttttgtagat catattaaaa ttgcaaacaa atcatctttt aatgggccag  1642
cattctcatg gggtagagca gaatattcat ttagcctgaa agctgcagtt actataggtt  1702
gctgtcagac tatacccatg gtgcctctgg gcttgacagg tcaaaatggt ccccatcagc  1762
ctggagcagc cctccagacc tgggtggaat tccagggttg agagactccc ctgagccaga  1822
ggccactagg tattcttgct cccagaggct gaagtcaccc tgggaatcac agtggtctac  1882
ctgcattcat aattccagga tctgtgaaga gcacatatgt gtcagggcac aattccctct  1942
cataaaaacc acacagcctg gaaattggcc ctggcccttc aagatagcct tctttagaat  2002
atgatttggc tagaaagatt cttaaatatg tggaatatga ttattcttag ctggaatatt  2062
ttctctactt cctgtctgca tgcccaaggc ttctgaagca gccaatgtcg atgcaacaac  2122
atttgtaact ttaggtaaac tgggattatg ttgtagttta acattttgta actgtgtgct  2182
tatagtttac aagtgagacc cgatatgtca ttatgcatac ttatattatc ttaagcatgt  2242
gtaatgctgg atgtgtacag tacagtacwt aacttgtaat ttgaatctag tatggtgttc  2302
tgttttcagc tgacttggac aacctgactg gctttgcaca ggtgttccct gagttgtttg  2362
caggtttctg tgtgtggggt ggggtatggg gaggagaacc ttcatggtgg cccacctggc  2422
ctggttgtcc aagctgtgcc tcgacacatc ctcatcccaa gcatgggaca cctcaagatg  2482
aataataatt cacaaaattt ctgtgaaatc aaatccagtt ttaagaggag ccacttatca  2542
aagagatttt aacagtagta agaaggcaaa gaataaacat ttgatattca gcaactgaaa  2602
aaaaaaaa                                                         2610
```

<210> SEQ ID NO 4

```
<211> LENGTH: 2072
<212> TYPE: DNA
<213> ORGANISM: Rattus norvegicus
<220> FEATURE:
<221> NAME/KEY: CDS
<222> LOCATION: (35)...(634)

<400> SEQUENCE: 4
ctggagggga agagtgcagc tgttcctggc agac atg aag ccc tac ttc tcg tgc        55
                                     Met Lys Pro Tyr Phe Ser Cys
                                      1               5 gtc ttt gtc ttc tgc ttc cta atc aaa ctt tta aca gga gaa ctc aat         103
Val Phe Val Phe Cys Phe Leu Ile Lys Leu Leu Thr Gly Glu Leu Asn
         10                  15                  20 gac ttg gcc aat cac agg atg ttt tcg ttt cac gat gga ggt gta cag         151
Asp Leu Ala Asn His Arg Met Phe Ser Phe His Asp Gly Gly Val Gln
 25                  30                  35 att tct tgt aac tac cct gag act gtc cag cag tta aaa atg cag ttg         199
Ile Ser Cys Asn Tyr Pro Glu Thr Val Gln Gln Leu Lys Met Gln Leu
 40                  45                  50                  55 ttc aaa gac aga gaa gtc ctc tgc gac ctc acc aag acc aag gga agc         247
Phe Lys Asp Arg Glu Val Leu Cys Asp Leu Thr Lys Thr Lys Gly Ser
             60                  65                  70 gga aac acc gtg tcc atc aag aat ccg atg tcc tgt cca tat cag ctg         295
Gly Asn Thr Val Ser Ile Lys Asn Pro Met Ser Cys Pro Tyr Gln Leu
     75                  80                  85 tcc aac aac agt gtc tct ttt ttc cta gac aac gca gac agc tcc cag         343
Ser Asn Asn Ser Val Ser Phe Phe Leu Asp Asn Ala Asp Ser Ser Gln
 90                  95                  100 ggc agc tac ttt tta tgc agc ctg tcg att ttc gac cca ccc cct ttt         391
Gly Ser Tyr Phe Leu Cys Ser Leu Ser Ile Phe Asp Pro Pro Pro Phe
         105                 110                 115 caa gaa aag aac ctt agt gga gga tat ttg ctt att tat gaa tcc cag         439
Gln Glu Lys Asn Leu Ser Gly Gly Tyr Leu Leu Ile Tyr Glu Ser Gln
120                 125                 130                 135 ctt tgt tgc cag ctg aag ctt tgg tta ccc gta ggg tgt gca gct ttt         487
Leu Cys Cys Gln Leu Lys Leu Trp Leu Pro Val Gly Cys Ala Ala Phe
             140                 145                 150 gtg gca gcg ctc ctt ttt gga tgc ata ttt atc gtc tgg ttt gca aaa         535
Val Ala Ala Leu Leu Phe Gly Cys Ile Phe Ile Val Trp Phe Ala Lys
     155                 160                 165 aag aag tac aga tcc agt gtg cac gac cct aat agc gag tac atg ttc         583
Lys Lys Tyr Arg Ser Ser Val His Asp Pro Asn Ser Glu Tyr Met Phe
 170                 175                 180 atg gcg gca gtc aac aca aac aaa aag tcc aga ctt gca ggt atg acc         631
Met Ala Ala Val Asn Thr Asn Lys Lys Ser Arg Leu Ala Gly Met Thr
         185                 190                 195 tca taatctggaa cacgggaacc catggaggaa ctacactgtc tagttcccct              684
Ser
200 gaaacttgaa tggagaaagt cttctatttt ctggaccaca gggcatctga cttgattaac       744 tactgatacc tccttttggk gttttgtttg tctggatcag tgactatcag tcactcggaa       804 tttcagcaga ctgccctggg tttgctgagt ccttttaagg caaaccccct cttatagaag       864 acccggctca tatgtattca acaaacagac ctcactggga tacaatcccc tctttctgcg       924 cctgcttcta gctatgcacc ggccagcaag acaaacatat ctccagcatt tttacaaaaa       984 tgccagggta tgaatctgta aagtacacag gcagccattg accacgtct  gtcctcgttt      1044 tttcagattc tatttttttc catagagatc agcattcctt ctagaatcag acagtagagg      1104 gagatgcttc acaacagaag ctcttatgtt tctgagatgt tgatgaattc atgctttagt      1164
```

```
accaccatgt tctctaacaa cttctatatt ccagctgatc actgcttcag ggcttagatg    1224
cctgcttttg ccttcaagtc tccccttaaa gatactccca caggtctact tggtggcctg    1284
cagccactct gaataggaag tttggtctac aatttccccc ctctgctgct caaaaaaaaa    1344
aattagtaga tatgattttc ccatattctc cctgccaaag taattttttc cagcaaagac    1404
atctaaattc agttaatatg gtttactgtg ttgatattag tggcagtaaa catttctcag    1464
aatcaaaagc aaattaattt tgcggtggtg tttttctacc attatcttgg gtttccatgg    1524
tgctattact cacaagttta gctatttttt tatgcatcat attaaagttg caagcaagca    1584
gagcaaccct cggttaatgg gcaaacattc tcctggggta gaatgaattg tctatttagc    1644
ccgaaaactg cagtttctgt gggtggctgc cagactacag ccgtgctttg ctctggcttt    1704
gacaggttga aatagyCCCC atgascstgg aacagwactc cagactgtgc tggagtccca    1764
aagttaggag ggccatggag cctgggacag gctgctgctt tggtctttag gatctaggaa    1824
raattacaga ggggccaaga cagagttccc tcccctagaa actgtgcagc ctggaagtca    1884
gccctggcac tttaagatag ccttctttag aacatgagtt agttggtagt attctgacgt    1944
gtaaacagcc tatkgttgct cggagctgga ccatttctc cacttccctg tctgcatgcc     2004
taagacttct agagcagcca acgtatatgc aacattaaag aaaaaaaaaa aaaaaaaaa    2064 aaaaaaaa                                                             2072

<210> SEQ ID NO 5
<211> LENGTH: 603
<212> TYPE: DNA
<213> ORGANISM: Mus musculus
<220> FEATURE:
<221> NAME/KEY: CDS
<222> LOCATION: (1)...(600)

<400> SEQUENCE: 5 atg aag ccg tac ttc tgc cat gtc ttt gtc ttc tgc ttc cta atc aga      48
Met Lys Pro Tyr Phe Cys His Val Phe Val Phe Cys Phe Leu Ile Arg
 1               5                  10                  15 ctt tta aca gga gaa atc aat ggc tcg gcc gat cat agg atg ttt tca      96
Leu Leu Thr Gly Glu Ile Asn Gly Ser Ala Asp His Arg Met Phe Ser
             20                  25                  30 ttt cac aat gga ggt gta cag att tct tgt aaa tac cct gag act gtc     144
Phe His Asn Gly Gly Val Gln Ile Ser Cys Lys Tyr Pro Glu Thr Val
         35                  40                  45 cag cag tta aaa atg cga ttg ttc aga gag aga gaa gtc ctc tgc gaa     192
Gln Gln Leu Lys Met Arg Leu Phe Arg Glu Arg Glu Val Leu Cys Glu
     50                  55                  60 ctc acc aag acc aag gga agc gga aat gcg gtg tcc atc aag aat cca     240
Leu Thr Lys Thr Lys Gly Ser Gly Asn Ala Val Ser Ile Lys Asn Pro
 65                  70                  75                  80 atg ctc tgt cta tat cat ctg tca aac aac agc gtc tct ttt ttc cta     288
Met Leu Cys Leu Tyr His Leu Ser Asn Asn Ser Val Ser Phe Phe Leu
                 85                  90                  95 aac aac cca gac agc tcc cag gga agc tat tac ttc tgc agc ctg tcc     336
Asn Asn Pro Asp Ser Ser Gln Gly Ser Tyr Tyr Phe Cys Ser Leu Ser
            100                 105                 110 att ttt gac cca cct cct ttt caa gaa agg aac ctt agt gga gga tat     384
Ile Phe Asp Pro Pro Pro Phe Gln Glu Arg Asn Leu Ser Gly Gly Tyr
        115                 120                 125 ttg cat att tat gaa tcc cag ctc tgc tgc cag ctg aag ctc tgg cta     432
Leu His Ile Tyr Glu Ser Gln Leu Cys Cys Gln Leu Lys Leu Trp Leu
    130                 135                 140
```

```
ccc gta ggg ttg cca gct ttc gtt gtg gta ctc ctt ttt gga tgc ata       480
Pro Val Gly Leu Pro Ala Phe Val Val Val Leu Leu Phe Gly Cys Ile
145                 150                 155                 160 ctt atc atc tgg ttt tca aaa aag aaa tac gga tcc agt gtg cat gac       528
Leu Ile Ile Trp Phe Ser Lys Lys Lys Tyr Gly Ser Ser Val His Asp
                165                 170                 175 cct aat agt gaa tac atg ttc atg gcg gca gtc aac aca aac aaa aag       576
Pro Asn Ser Glu Tyr Met Phe Met Ala Ala Val Asn Thr Asn Lys Lys
            180                 185                 190 tct aga ctt gca ggt gtg acc tca taa                                   603
Ser Arg Leu Ala Gly Val Thr Ser
        195                 200

<210> SEQ ID NO 6
<211> LENGTH: 836
<212> TYPE: DNA
<213> ORGANISM: Rattus norvegicus
<220> FEATURE:
<221> NAME/KEY: CDS
<222> LOCATION: (35)...(682)

<400> SEQUENCE: 6
ctggagggga agagtgcagc tgttcctggc agac atg aag ccc tac ttc tcg tgc      55
                                     Met Lys Pro Tyr Phe Ser Cys
                                       1               5 gtc ttt gtc ttc tgc ttc cta atc aaa ctt tta aca gga gaa ctc aat       103
Val Phe Val Phe Cys Phe Leu Ile Lys Leu Leu Thr Gly Glu Leu Asn
            10                  15                  20 gac ttg gcc aat cac agg atg ttt tcg ttt cac gat gga ggt gta cag       151
Asp Leu Ala Asn His Arg Met Phe Ser Phe His Asp Gly Gly Val Gln
        25                  30                  35 att tct tgt aac tac cct gag act gtc cag cag tta aaa atg cag ttg       199
Ile Ser Cys Asn Tyr Pro Glu Thr Val Gln Gln Leu Lys Met Gln Leu
40                  45                  50                  55 ttc aaa gac aga gaa gtc ctc tgc gac ctc acc aag acc aag gga agc       247
Phe Lys Asp Arg Glu Val Leu Cys Asp Leu Thr Lys Thr Lys Gly Ser
                60                  65                  70 gga aac acc gtg tcc atc aag aat ccg atg tcc tgt cca tat cag ctg       295
Gly Asn Thr Val Ser Ile Lys Asn Pro Met Ser Cys Pro Tyr Gln Leu
            75                  80                  85 tcc aac aac agt gtc tct ttt ttc cta gac aac gca gac agc tcc cag       343
Ser Asn Asn Ser Val Ser Phe Phe Leu Asp Asn Ala Asp Ser Ser Gln
        90                  95                  100 ggc agc tac ttt tta tgc agc ctg tcg att ttc gac cca ccc cct ttt       391
Gly Ser Tyr Phe Leu Cys Ser Leu Ser Ile Phe Asp Pro Pro Pro Phe
105                 110                 115 caa gaa aag aac ctt agt gga gga tat ttg ctt att tat gaa tcc cag       439
Gln Glu Lys Asn Leu Ser Gly Gly Tyr Leu Leu Ile Tyr Glu Ser Gln
120                 125                 130                 135 ctt tgt tgc cag ctg aag ctt tgg tta ccc gta ggg tgt gca gct ttt       487
Leu Cys Cys Gln Leu Lys Leu Trp Leu Pro Val Gly Cys Ala Ala Phe
                140                 145                 150 gtg gca gcg ctc ctt ttt gga tgc ata ttt atc gtc tgg ttt gca aaa       535
Val Ala Ala Leu Leu Phe Gly Cys Ile Phe Ile Val Trp Phe Ala Lys
            155                 160                 165 aag aag tac aga tcc agt gtg cac gac cct aat agc gag tac atg ttc       583
Lys Lys Tyr Arg Ser Ser Val His Asp Pro Asn Ser Glu Tyr Met Phe
        170                 175                 180 atg gcg gca gtc aac aca aac aaa aag tcc aga ctt gca ggt aca gca       631
Met Ala Ala Val Asn Thr Asn Lys Lys Ser Arg Leu Ala Gly Thr Ala
185                 190                 195 ccc ctt agg gct ttg ggg aga gga gaa cac tct tca tgt caa gac cgg       679
Pro Leu Arg Ala Leu Gly Arg Gly Glu His Ser Ser Cys Gln Asp Arg
```

```
Pro Leu Arg Ala Leu Gly Arg Gly Glu His Ser Ser Cys Gln Asp Arg
200                 205                 210                 215 aat taatttgttt atttctattt taaaagaaag acattttttc ccctaaagat            732
Asn aattttttgta ttttttatgtg aaagtctgaa tcttcatttt aactcgactt atatactctg   792
tggtatatta aaataatgt ttgtgaaaaa aaaaaaaaaa aaaa                       836

<210> SEQ ID NO 7
<211> LENGTH: 27
<212> TYPE: DNA
<213> ORGANISM: Artificial Sequence
<220> FEATURE:
<223> OTHER INFORMATION: primer for PCR

<400> SEQUENCE: 7
ctgctcgaga tgaagcccta cttctcg                                          27

<210> SEQ ID NO 8
<211> LENGTH: 32
<212> TYPE: DNA
<213> ORGANISM: Artificial Sequence
<220> FEATURE:
<223> OTHER INFORMATION: primer for PCR

<400> SEQUENCE: 8
accctacggg taacggatcc ttcagctggc aa                                    32

<210> SEQ ID NO 9
<211> LENGTH: 30
<212> TYPE: DNA
<213> ORGANISM: Artificial Sequence
<220> FEATURE:
<223> OTHER INFORMATION: primer for PCR

<400> SEQUENCE: 9
taactgtttc tcgagaacat gaagtcaggc                                       30

<210> SEQ ID NO 10
<211> LENGTH: 30
<212> TYPE: DNA
<213> ORGANISM: Artificial Sequence
<220> FEATURE:
<223> OTHER INFORMATION: primer for PCR

<400> SEQUENCE: 10
atcctatggg taacggatcc ttcagctggc                                       30

<210> SEQ ID NO 11
<211> LENGTH: 35
<212> TYPE: DNA
<213> ORGANISM: Artificial Sequence
<220> FEATURE:
<223> OTHER INFORMATION: primer for PCR

<400> SEQUENCE: 11
cgtgatattg ctgaagagct tggcggcgaa tgggc                                 35

<210> SEQ ID NO 12
<211> LENGTH: 34
<212> TYPE: DNA
<213> ORGANISM: Artificial Sequence
<220> FEATURE:
<223> OTHER INFORMATION: primer for PCR

<400> SEQUENCE: 12
```
cattcaagtt tcagggaact agtccatgcg tttc                        34

<210> SEQ ID NO 13
<211> LENGTH: 200
<212> TYPE: PRT
<213> ORGANISM: Rattus norvegicus

<400> SEQUENCE: 13

Met Lys Pro Tyr Phe Ser Cys Val Phe Val Phe Cys Phe Leu Ile Lys
1               5                   10                  15

Leu Leu Thr Gly Glu Leu Asn Asp Leu Ala Asn His Arg Met Phe Ser
            20                  25                  30

Phe His Asp Gly Gly Val Gln Ile Ser Cys Asn Tyr Pro Glu Thr Val
        35                  40                  45

Gln Gln Leu Lys Met Gln Leu Phe Lys Asp Arg Glu Val Leu Cys Asp
    50                  55                  60

Leu Thr Lys Thr Lys Gly Ser Gly Asn Thr Val Ser Ile Lys Asn Pro
65                  70                  75                  80

Met Ser Cys Pro Tyr Gln Leu Ser Asn Asn Ser Val Ser Phe Phe Leu
                85                  90                  95

Asp Asn Ala Asp Ser Ser Gln Gly Ser Tyr Phe Leu Cys Ser Leu Ser
            100                 105                 110

Ile Phe Asp Pro Pro Phe Gln Glu Lys Asn Leu Ser Gly Gly Tyr
            115                 120                 125

Leu Leu Ile Tyr Glu Ser Gln Leu Cys Cys Gln Leu Lys Leu Trp Leu
    130                 135                 140

Pro Val Gly Cys Ala Ala Phe Val Ala Ala Leu Leu Phe Gly Cys Ile
145                 150                 155                 160

Phe Ile Val Trp Phe Ala Lys Lys Lys Tyr Arg Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Met Thr Ser
        195                 200

<210> SEQ ID NO 14
<211> LENGTH: 200
<212> TYPE: PRT
<213> ORGANISM: Mus musculus

<400> SEQUENCE: 14

Met Lys Pro Tyr Phe Cys His Val Phe Val Cys Phe Leu Ile Arg
1               5                   10                  15

Leu Leu Thr Gly Glu Ile Asn Gly Ser Ala Asp His Arg Met Phe Ser
            20                  25                  30

Phe His Asn Gly Gly Val Gln Ile Ser Cys Lys Tyr Pro Glu Thr Val
        35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80

Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
            100                 105                 110

Ile Phe Asp Pro Pro Phe Gln Glu Arg Asn Leu Ser Gly Gly Tyr
            115                 120                 125

```
Leu His Ile Tyr Glu Ser Gln Leu Cys Cys Gln Leu Lys Leu Trp Leu
    130                 135                 140
Pro Val Gly Leu Pro Ala Phe Val Val Leu Leu Phe Gly Cys Ile
145                 150                 155                 160
Leu Ile Ile Trp Phe Ser Lys Lys Tyr Gly Ser Ser Val His Asp
                165                 170                 175
Pro Asn Ser Glu Tyr Met Phe Met Ala Ala Val Asn Thr Asn Lys Lys
                180                 185                 190
Ser Arg Leu Ala Gly Val Thr Ser
        195                 200

<210> SEQ ID NO 15
<211> LENGTH: 216
<212> TYPE: PRT
<213> ORGANISM: Rattus norvegicus

<400> SEQUENCE: 15

Met Lys Pro Tyr Phe Ser Cys Val Phe Val Cys Phe Leu Ile Lys
1               5                   10                  15
Leu Leu Thr Gly Glu Leu Asn Asp Leu Ala Asn His Arg Met Phe Ser
                20                  25                  30
Phe His Asp Gly Gly Val Gln Ile Ser Cys Asn Tyr Pro Glu Thr Val
                35                  40                  45
Gln Gln Leu Lys Met Gln Leu Phe Lys Asp Arg Glu Val Leu Cys Asp
    50                  55                  60
Leu Thr Lys Thr Lys Gly Ser Gly Asn Thr Val Ser Ile Lys Asn Pro
65                  70                  75                  80
Met Ser Cys Pro Tyr Gln Leu Ser Asn Asn Ser Val Ser Phe Phe Leu
                85                  90                  95
Asp Asn Ala Asp Ser Ser Gln Gly Ser Tyr Phe Leu Cys Ser Leu Ser
                100                 105                 110
Ile Phe Asp Pro Pro Phe Gln Glu Lys Asn Leu Ser Gly Gly Tyr
            115                 120                 125
Leu Leu Ile Tyr Glu Ser Gln Leu Cys Cys Gln Leu Lys Leu Trp Leu
    130                 135                 140
Pro Val Gly Cys Ala Ala Phe Val Ala Ala Leu Leu Phe Gly Cys Ile
145                 150                 155                 160
Phe Ile Val Trp Phe Ala Lys Lys Lys Tyr Arg Ser Ser Val His Asp
                165                 170                 175
Pro Asn Ser Glu Tyr Met Phe Met Ala Ala Val Asn Thr Asn Lys Lys
                180                 185                 190
Ser Arg Leu Ala Gly Thr Ala Pro Leu Arg Ala Leu Gly Arg Gly Glu
        195                 200                 205
His Ser Ser Cys Gln Asp Arg Asn
    210                 215

<210> SEQ ID NO 16
<211> LENGTH: 200
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(200)
<223> OTHER INFORMATION: Xaa = Any Amino Acid

<400> SEQUENCE: 16
```

```
Met Lys Pro Tyr Phe Xaa Xaa Val Phe Val Phe Cys Phe Leu Ile Lys
 1               5                  10                  15

Leu Leu Thr Gly Glu Xaa Asn Xaa Xaa Ala Asn His Arg Met Phe Ser
            20                  25                  30

Phe His Xaa Gly Gly Val Gln Ile Ser Cys Xaa Tyr Pro Glu Thr Val
            35                  40                  45

Gln Gln Leu Lys Met Gln Leu Phe Lys Xaa Arg Glu Val Leu Cys Asp
    50                  55                  60

Leu Thr Lys Thr Lys Gly Ser Gly Asn Thr Val Ser Ile Lys Asn Pro
65                  70                  75                  80

Met Xaa Cys Xaa Tyr Gln Leu Ser Asn Asn Ser Val Ser Phe Phe Leu
            85                  90                  95

Xaa Asn Xaa Asp Ser Ser Gln Gly Ser Tyr Xaa Xaa Cys Ser Leu Ser
            100                 105                 110

Ile Phe Asp Pro Pro Phe Gln Glu Xaa Asn Leu Ser Gly Gly Tyr
            115                 120                 125

Leu Xaa Ile Tyr Glu Ser Gln Leu Cys Cys Gln Leu Lys Leu Trp Leu
    130                 135                 140

Pro Val Gly Cys Ala Ala Phe Val Xaa Xaa Leu Leu Phe Gly Cys Ile
145                 150                 155                 160

Xaa Ile Xaa Trp Phe Xaa Lys Lys Lys Tyr Xaa Ser Ser Val His Asp
            165                 170                 175

Pro Asn Ser Glu Tyr Met Phe Met Ala Ala Val Asn Thr Asn Lys Lys
            180                 185                 190

Ser Arg Leu Ala Gly Xaa Thr Xaa
            195                 200

<210> SEQ ID NO 17
<211> LENGTH: 214
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(214)
<223> OTHER INFORMATION: Xaa = Any Amino Acid

<400> SEQUENCE: 17

Met Leu Xaa Leu Xaa Leu Ala Trp Xaa Leu Xaa Leu Phe Xaa Leu Xaa
 1               5                  10                  15

Ile Xaa Val Xaa Xaa Xaa Xaa Ile Xaa Val Xaa Gln Xaa Xaa Xaa Xaa
            20                  25                  30

Xaa Ala Xaa Xaa Asn Gly Xaa Xaa Xaa Xaa Xaa Cys Lys Tyr Xaa Xaa
            35                  40                  45

Pro Xaa Xaa Xaa Xaa Glu Phe Arg Xaa Xaa Leu Leu Lys Gly Xaa Asp
    50                  55                  60

Ser Xaa Val Xaa Xaa Cys Xaa Xaa Xaa Thr Tyr Xaa Xaa Gly Asn
65                  70                  75                  80

Xaa Val Xaa Xaa Lys Xaa Xaa Xaa Xaa Cys Xaa Gly Xaa Leu Ser Asn
            85                  90                  95

Asn Ser Val Xaa Phe Xaa Leu Gln Asn Leu Xaa Xaa Xaa Xaa Thr Xaa
            100                 105                 110

Xaa Tyr Phe Cys Lys Xaa Glu Xaa Met Tyr Pro Pro Tyr Xaa Xaa
    115                 120                 125

Xaa Xaa Xaa Asn Gly Thr Xaa Ile His Val Xaa Xaa Xaa Xaa Leu Cys
130                 135                 140
```

-continued

```
Pro Xaa Xaa Xaa Phe Xaa Xaa Trp Xaa Leu Xaa Xaa Val Xaa Xaa Xaa
145                 150                 155                 160

Leu Xaa Xaa Tyr Ser Xaa Leu Xaa Thr Ala Xaa Ile Xaa Xaa Xaa Xaa
                165                 170                 175

Xaa Lys Lys Arg Ser Xaa Leu Xaa Xaa Gly Xaa Tyr Met Xaa Met Xaa
        180                 185                 190

Pro Xaa Xaa Pro Xaa Xaa Xaa Xaa Lys Xaa Xaa Gln Pro Tyr Xaa Xaa
        195                 200                 205

Asp Phe Xaa Xaa Xaa Xaa
        210

<210> SEQ ID NO 18
<211> LENGTH: 6
<212> TYPE: PRT
<213> ORGANISM: Homo sapiens

<400> SEQUENCE: 18

Met Tyr Pro Pro Pro Tyr
1               5

<210> SEQ ID NO 19
<211> LENGTH: 4
<212> TYPE: PRT
<213> ORGANISM: Homo sapiens

<400> SEQUENCE: 19

Tyr Met Asn Met
1

<210> SEQ ID NO 20
<211> LENGTH: 4
<212> TYPE: PRT
<213> ORGANISM: Homo sapiens

<400> SEQUENCE: 20

Tyr Val Lys Met
1

<210> SEQ ID NO 21
<211> LENGTH: 6
<212> TYPE: PRT
<213> ORGANISM: Homo sapiens

<400> SEQUENCE: 21

Phe Asp Pro Pro Pro Phe
1               5

<210> SEQ ID NO 22
<211> LENGTH: 4
<212> TYPE: PRT
<213> ORGANISM: Homo sapiens

<400> SEQUENCE: 22

Tyr Met Phe Met
1

<210> SEQ ID NO 23
<211> LENGTH: 216
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(216)
```

<223> OTHER INFORMATION: Xaa = Any Amino Acid

<400> SEQUENCE: 23

```
Met Lys Pro Tyr Phe Ser Cys Val Phe Val Phe Cys Phe Leu Ile Lys
1               5                   10                  15

Leu Leu Thr Gly Glu Leu Asn Asp Leu Ala Asn His Arg Met Phe Ser
            20                  25                  30

Phe His Asp Gly Gly Val Gln Ile Ser Cys Asn Tyr Pro Glu Thr Val
        35                  40                  45

Gln Gln Leu Lys Met Gln Leu Phe Lys Asp Arg Glu Val Leu Cys Asp
    50                  55                  60

Leu Thr Lys Thr Lys Gly Ser Gly Asn Thr Val Ser Ile Lys Asn Pro
65              70                  75                  80

Met Ser Cys Pro Tyr Gln Leu Ser Asn Asn Ser Val Ser Phe Phe Leu
                85                  90                  95

Asp Asn Ala Asp Ser Ser Gln Gly Ser Tyr Phe Leu Cys Ser Leu Ser
            100                 105                 110

Ile Phe Asp Pro Pro Phe Gln Glu Lys Asn Leu Ser Gly Gly Tyr
        115                 120                 125

Leu Leu Ile Tyr Glu Ser Gln Leu Cys Cys Gln Leu Lys Leu Trp Leu
    130                 135                 140

Pro Val Gly Cys Ala Ala Phe Val Ala Ala Leu Leu Phe Gly Cys Ile
145             150                 155                 160

Phe Ile Val Trp Phe Ala Lys Lys Lys Tyr Arg Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Xaa Xaa Xaa Xaa Xaa Xaa Xaa Xaa Xaa
    195                 200                 205

Xaa Xaa Xaa Xaa Xaa Xaa Xaa Xaa
    210                 215
```

<210> SEQ ID NO 24
<211> LENGTH: 16
<212> TYPE: PRT
<213> ORGANISM: Rattus norvegicus

<400> SEQUENCE: 24

```
Leu Arg Ala Leu Gly Arg Gly Glu His Ser Ser Cys Gln Asp Arg Asn
1               5                   10                  15
```

<210> SEQ ID NO 25
<211> LENGTH: 220
<212> TYPE: PRT
<213> ORGANISM: Homo sapiens

<400> SEQUENCE: 25

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65              70                  75                  80
```

```
Lys Thr Gly Phe Asn Cys Asp Gly Lys Leu Gly Asn Glu Ser Val Thr
                 85                  90                  95
Phe Tyr Leu Gln Asn Leu Tyr Val Asn Gln Thr Asp Ile Tyr Phe Cys
                100                 105                 110
Lys Ile Glu Val Met Tyr Pro Pro Tyr Leu Asp Asn Glu Lys Ser
            115                 120                 125
Asn Gly Thr Ile Ile His Val Lys Gly Lys His Leu Cys Pro Ser Pro
            130                 135                 140
Leu Phe Pro Gly Pro Ser Lys Pro Phe Trp Val Leu Val Val Val Gly
145                 150                 155                 160
Gly Val Leu Ala Cys Tyr Ser Leu Leu Val Thr Val Ala Phe Ile Ile
                165                 170                 175
Phe Trp Val Arg Ser Lys Arg Ser Arg Leu Leu His Ser Asp Tyr Met
                180                 185                 190
Asn Met Thr Pro Arg Arg Pro Gly Pro Thr Arg Lys His Tyr Gln Pro
                195                 200                 205
Tyr Ala Pro Pro Arg Asp Phe Ala Ala Tyr Arg Ser
                210                 215                 220
```

<210> SEQ ID NO 26
<211> LENGTH: 223
<212> TYPE: PRT
<213> ORGANISM: Homo sapiens

<400> SEQUENCE: 26

```
Met Ala Cys Leu Gly Phe Gln Arg His Lys Ala Gln Leu Asn Leu Ala
  1               5                  10                  15
Ala Arg Thr Trp Pro Cys Thr Leu Leu Phe Phe Leu Leu Phe Ile Pro
                 20                  25                  30
Val Phe Cys Lys Ala Met His Val Ala Gln Pro Ala Val Val Leu Ala
                 35                  40                  45
Ser Ser Arg Gly Ile Ala Ser Phe Val Cys Glu Tyr Ala Ser Pro Gly
             50                  55                  60
Lys Ala Tyr Glu Val Arg Val Thr Val Leu Arg Gln Ala Asp Ser Gln
 65                  70                  75                  80
Val Thr Glu Val Cys Ala Ala Thr Tyr Met Thr Gly Asn Glu Leu Thr
                 85                  90                  95
Phe Leu Asp Asp Ser Ile Cys Thr Gly Thr Ser Ser Gly Asn Gln Val
                100                 105                 110
Asn Leu Thr Ile Gln Gly Leu Arg Ala Met Asp Thr Gly Leu Tyr Ile
            115                 120                 125
Cys Lys Val Glu Leu Met Tyr Pro Pro Tyr Tyr Leu Gly Ile Gly
            130                 135                 140
Asn Gly Thr Gln Ile Tyr Val Ile Asp Pro Glu Pro Cys Pro Asp Ser
145                 150                 155                 160
Asp Phe Leu Leu Trp Ile Leu Ala Ala Val Ser Ser Gly Leu Phe Phe
                165                 170                 175
Tyr Ser Phe Leu Leu Thr Ala Val Ser Leu Ser Lys Met Leu Lys Lys
                180                 185                 190
Arg Ser Pro Leu Thr Thr Gly Val Tyr Val Lys Met Pro Pro Thr Glu
            195                 200                 205
Pro Glu Cys Glu Lys Gln Phe Gln Pro Tyr Phe Ile Pro Ile Asn
            210                 215                 220
```

ANTIBODIES TO JTT-1 PROTEIN AND CELLS SECRETING SUCH ANTIBODIES

CROSS REFERENCE TO RELATED APPLICATIONS

This application is a continuation and claims the benefit of priority under 35 USC §120 of U.S. application Ser. No. 10/721,404, filed Nov. 25, 2003, issued as U.S. Pat. No. 7,294,473 on Nov. 13, 2007, which is a continuation of U.S. application Ser. No. 10/301,056, filed Nov. 21, 2002, abandoned, which is a divisional of U.S. application Ser. No. 09/383,551, filed Aug. 26, 1999, issued as U.S. Pat. No. 7,030,225 on Apr. 18, 2006, which is a continuation-in-part of international application number PCT/JP98/00837, filed Feb. 27, 1998, which claims the benefit of priority under 35 USC §119 of Japanese application number 10/62217, filed Feb. 26, 1998 and Japanese application number 9/62290, filed Feb. 27, 1997. The disclosures of the prior applications are considered part of (and are incorporated by reference in) the disclosure of this application.

TECHNICAL FIELD

The present invention relates to novel cell surface molecules of mammals; polypeptides and their fragments constituting the molecules; fusion polypeptides comprising the polypeptide fragments and immunoglobulin fragments; genes encoding the polypeptides and the fragments; vectors comprising the genes; transformants into which the vectors are introduced; antibodies having reactivity to the polypeptides or cell surface molecules comprising the polypeptides; hybridomas producing the antibodies; pharmaceutical compositions comprising the polypeptide fragments or the fusion polypeptides; pharmaceutical compositions comprising the antibodies; transgenic mice; and knockout mice.

BACKGROUND ART

A living body of mammals has immune response systems that excludes pathogenic microorganisms (viruses, bacteria, parasites, etc.) or foreign bodies (both are called "antigen" in the following) that have invaded the living body. One of them is called natural immune response system, another acquired immune response system. The former is an exclusion mechanism comprising phagocytosis by phagocytes (polymorphonuclear leukocytes, monocytes, macrophages, etc.), attack by natural killer (NK) cells, and non-specific recognition such as opsonization of antigen by complements. The latter, acquired immune response system, is an exclusion mechanism by lymphocytes (mainly, T cells and B cells) that acquired the specificity to the antigen (namely, activated lymphocytes). B cells that acquired antigen specificity attacks the antigen existing outside of the cells through production of antibodies specific to the antigen. T cells that acquired antigen specificity (namely, activated T cells) are classified into helper T cells and cytotoxic T cells (cytotoxic lymphocyte, CTL). The helper T cells regulate a differentiation of B cells and a production of antibodies, and destroy the antigen cooperating with phagocytes. The latter, CTLs attack virus-infected cells and so on by themselves (Experimental Medicine: SUPPLEMENT, "Bio Science Term Library, Immunity", Yodosha, pp. 14-17 (1995)).

This acquisition of antigen specificity by T cells (namely, activation of T cells) is initiated through recognition by T cells the antigen presented by antigen-presenting cells (APC) such as macrophage, B cells, or dendritic cells. Antigen-presenting cells process the antigens so incorporated and present these processed antigens through binding them to major histocompatibility complex (MHC). T cells receives primary signal for activation of the cells (or acquisition of specificity) by recognizing the processed antigens presented by antigen-presenting cells through a complex between T cell receptor (TcR) and CD3 antigen existing on the surface of the cell membrane (TcR/CD3 complex).

However, the TcR/CD3 complex-mediated primary signal alone cannot activate T cells sufficiently and leads to unresponsiveness or clonal anergy, so that the cells can not react with any stimulation received thereafter. The autocrine of interleukin 2 (IL-2) is necessary for T cells to be activated, to be differentiated into antigen specific T cell clones, and to be proliferated. In clonal anergy, T cells are inactivated due to no production of IL-2 and no cell division. Namely, the activation of T cells accompanied by production of cytokines such as IL-2 requires the secondary signal following the first signal through TcR/CD3 complex. This secondary signal is called costimulatory signal.

T cells receive this secondary signal and transmit it into the cells by interacting (cell adhesion) with molecules other than MHC on antigen-presenting cells through other molecules other than TcR/CD3 complex on the T cell surface. This secondary signal avoids cell anergy (clonal anergy) and activates the cells.

Although some part of the mechanism of the secondary signal transmission between antigen-presenting cells and lymphocytes such as T cells have not yet been elucidated in detail, studies so far have revealed that an important factor for the secondary signal transmission is the interaction of CD28 (also named Tp44, T44, or 9.3 antigen), which is a cell surface molecule expressed mainly on T cells and thymus cells, with CD80 (also named B7-1, B7, BB1, or B7/BB1), which is a cell surface molecule expressed on antigen-presenting cells (macrophages, monocytes, dendritic cells, and so on etc.) and with CD86 (also named B7-2 or B70), which is also a cell surface molecule on antigen-presenting cells (namely, cell adhesion through the binding between these molecules). Moreover, it has been experimentally elucidated that the interaction of Cytolytic T lymphocyte associated antigen 4 (CTLA-4), whose expression is thought to be enhanced depending on the secondary signal, with the CD80 (B7-1) and CD86 (B7-2) (namely, cell adhesion through the binding between these molecules) also plays an important role in the regulation of T cell activation by the secondary signal. In other words, the regulation of T cell activation by the transmission of the secondary signal involves, at least the interaction between CD28 and CD80/CD86, the enhancement of CTLA-4 expression, which is thought to depend on the interaction, and the interaction between CTLA-4 and CD80/CD86.

CD28 is known to be a costimulator molecule transmitting the secondary signal (costimulatory signal) required for the activation of T cells and for the avoidance of anergy. The secondary signal transmitted by binding this molecule to costimulator molecules, CD80 (B7-1) and CD86 (B7-2), on antigen-presenting cells (namely, cell adhesion through the binding between these molecules), stabilizes mRNA of Th1-type cytokines and consequently promotes production by T cells of a large amount of production of Th1-type cytokines such as Il-2, IFNγ, and TNFα. The expression of CTLA-4 is induced by the primary signal transmitted through TcR/CD3, and the expression is also enhanced by the secondary signal transmitted by the binding between CD28 and CD80. It is being revealed that CTLA-4 receives these signals to work to inhibit T cell function, which is contrary to the activation of T cells by the secondary signal transmitted by CD28.

Human CD28 and CTLA-4 are I-type glycoproteins whose molecular weights are 44 kD and 41 to 43 kD, respectively. Both have an immunoglobulin-like domain, belong to the immunoglobulin superfamily, and have both function as a cell adhesion molecule and function as a signal transmission molecule.

Human CD28 forms a homodimer with a disulfide bond while CTLA-4 exists as a monomer. Both CD28 and CTLA-4 genes are located at "2q33" on human chromosome and "1C" on mouse chromosome, and are composed of four (4) exons. Human CD28 and CTLA-4 are composed of 220 and 223 amino acids, respectively, including the leader sequences, and amino acid homology between them is 20 to 30%.

The ligands for CD28 and CTLA-4 are CD80 (B7-1) and CD86 (B7-2) in human and mice. CTLA-4 has about 20 times as higher affinity to both ligands as CD28. It has been elucidated that the amino acid sequence structures "MYPPPY (Met-Tyr-Pro-Pro-Pro-Tyr)" conserved through animal species is important for the binding of CD28 and CTLA-4 to CD80 (B7-1). It has also been reported that, when CD28 is stimulated, PI3 kinase (phosphoinositide 3 kinase, PI3K) associates with the phosphorylated tyrosine residue in a partial sequence "YMNM (Tyr-Met-Asn-Met)" of CD28 "YMNM (Tyr-Met-Asn-Met)" and that CD28 plays an important role in intracellular signal transmission through this "YxxM" structure. Furthermore, it has been reported that CTLA-4 also has a sequence represented by "YxxM," namely "YVKM (Tyr-Val-Lys-Met)" in its cytoplasmic region and that, after being stimulated, SYP associates with this sequence.

CD28 is expressed specifically in thymocytes and peripheral blood T cells, and CTLA-4 is expressed specifically in activated T cells (Cell Engineering: SUPPLEMENT, "Handbook of Adhesion Molecule", Shujunsha, pp. 93-102 (1994); ibid. pp. 120-136; Experimental Medicine: SUPPLEMENT, "BIO SCIENCE Term Library, Immunity", Yodosha, pp. 94-98 (1995); Experimental Medicine: SUPPLEMENT, "BIO SCIENCE Term Library, Intracellular Signal Transduction", Yodosha, pp. 58-59 (1997); Nihon Rinsho, Vol. 55, No. 6, pp. 215-220 (1997)).

In the regulation of T cell function (the activation and the inhibition of function of T cells), the importance of interactions among multiple molecules such as costimulator molecules (CD28, CD80 (B7-1), CD86 (B7-2), etc.) and CTLA-4, which cooperates with them, (in other words, cell adhesion through the binding between these molecules) has thus been recognized, and this has been drawn attention to the relationship between these molecules and diseases, and the treatment of diseases by regulating the function of these molecules have been noted.

As described above, although a living body activates its acquired immune response system against antigens that are foreign bodies to the living body (self), it also has immunological tolerance so as to show no immune response against its own component (autoantigen). If immunological tolerance breaks down by some reason, immune response to the autoantigen occurs, autoantigen-reactive T cells are induced by the same mechanism as mentioned above to fall into abnormal state of immunity, and various autoimmune diseases are caused.

In other words, since non-stimulated antigen presenting cells (APC) in normal tissues do not express costimulatory molecules when the immune system of a living body is normal, T cells fall are in the unresponsiveness state to maintain immunological tolerance even if autoantigen-reactive T cells, which reacts with autoantigen, exist. It has been suggested that in abnormal state of immunity, more autoantigen-reactive T cells are activated due to abnormal excess and continuous expression of costimulatory molecules to thereby cause autoimmune diseases.

From such viewpoints recently, many attempts to treat for various autoimmune diseases by modulating the transmission of costimulatory signals, for example, the above-mentioned signal transmission between CD28/CTLA-4 and CD80/CD86, are proposed.

It has been observed CD80, a costimulatory molecule as the ligand of CD28 and CTLA-4, is abnormally expressed in the antigen presenting cells at the nidus of autoimmune disease such as rheumatoid arthritis, multiple sclerosis, autoimmune thyroiditis, allergic contact-type dermatitis, and chronic inflammatory dermatosis such as squamous lichen planus, and psoriasis. From such observation, many attempts to treat various autoimmune diseases by modulating the function of CD80 have been made.

It has been proposed to block the function of CD80, by methods using an antibody against CD80, solubilized protein of CD28 that is a ligand of CD80, and solubilized protein of CTLA-4 that is also a ligand of CD80. Particularly, based on the fact that the binding affinity of CTLA-4 to CD80 is 20 or more times higher than that of CD28, therapeutic attempts using "solubilized CTLA-4," specifically, the fusion protein (CTLA-4-IgFc) comprising the extracellular domain of "CTLA-4" and the Fc region of human immunoglobulin IgG1, were performed in animal model and clinical tests (Nihon Rinsho, Vol. 55, No. 6, pp. 215-220 (1997)).

As shown in 1 to 5 below, therapeutic effects of CTLA-4-IgFc in model animals of autoimmune diseases has been reported.

1. In a (NZB/NZW)F1 mouse, that is a model for human systemic lupus erythematosus (SLE), the production of autoantibodies and the onset of lupus nephritis were suppressed by administration of CTLA-4-IgFc before the onset, and the pathologic conditions were improved by administration of the drug even after the onset (Science, Vol. 125, p. 1225-1227 (1994)).

2. In experimental allergic encephalomyelitis (EAE), that is a model for multiple sclerosis (MS), the onset was prevented by short-term administration of CTLA-4-IgFc immediately after immunization (J. Clin. Invest., Vol. 95, pp. 2783-2789 (1995)).

3. In an NOD (non-obese diabetes) mouse, which is a model for insulin dependent diabetes mellitus (IDDM), the onset rate was remarkably decreased by administering CTLA-4-IgFc to the 2- or 3-week-old female mouse for two weeks (J. Exp. Med. 181:1145-1155, 1995).

4. In rat nephritis by renal glomerulus basement membrane immunity, Goodpasture's nephritis model, the improvement of the symptom has been improved by the administration of CTLA-4-IgFc (Eur. J. Immunol. 24:1249-1254, 1994).

5. In type II collagen-induced arthritis (CIA) using a DBA/1 mouse, that is a model for human rheumatoid arthritis, the onset of arthritis was suppressed by the administering the test drug at the time of immunization and the production of autoantibodies (IgG1 and IgG2) against collagen was inhibited (Eur. J. Immunol. 26:2320-2328, 1996).

The results of the experiments as mentioned above are have not yet clarified in detail the mechanism of the T cell activation by interaction between costimulatory molecules and the related molecules (in other words, cell adhesion through the binding between these molecules). Other unknown molecules may be involved in this mechanism.

DISCLOSURE OF THE INVENTION

Pharmaceuticals useful for treating or preventing various diseases such as the above-mentioned autoimmune diseases, allergic diseases, and inflammatory diseases can be developed if the mechanism of the activation of lymphocytes such as T cells by cell adhesion through the binding between molecules involved in the transmission of the secondary signal essential for the activation of lymphocytes such as T cells mentioned above and the mechanism of the regulation of lymphocyte function are clarified, and known or unknown molecules capable of mediating cell adhesion involved in the mechanism and of transmitting signals are identified and characterized.

An objective of the present invention is to identify novel cell surface molecules having both functions of mediating such cell adhesion and signal transmission, and to clarify its structural and biological characteristics. Another objective of the present invention is to provide pharmaceuticals useful for treating or preventing various autoimmune diseases and inflammatory diseases by using the novel molecules or antibodies against the molecules.

In order to identify such useful molecules, the present inventors focused on the fact that lymphocytes such as T cells play an important role in autoimmune diseases, and the fact that cell adhesion are essential for the signal transmission of the secondary signal (costimulatory signal) from antigen presenting cells into lymphocytes, and planned to isolate and identify cell surface molecules that are expressed specifically on lymphocytic cells and that mediate cell adhesion.

The present inventors obtained monoclonal antibodies against various cell surface molecules expressed on the surface of lymphocytic cells by immunizing animals against the lymphocytic cells, and isolated and identified desired cell surface molecules that mediate cell adhesion using the monoclonal antibodies so obtained. The methods used are described in detail below.

The present inventors first administered rat lymphocytic cell line as an antigen to mice and prepared various monoclonal antibodies. Then, the monoclonal antibodies obtained were reacted with rat lymphocytic cells used as an antigen and tested the effect of the monoclonal antibodies given to the cells. As a result, one of the monoclonal antibodies was obtained has been found to agglutinate the rat lymphocytic cells strongly (this monoclonal antibody was designated "JTT-1 antibody"). Moreover, other one of the monoclonal antibodies was found to strongly inhibit the agglutination of rat lymphocytic cells induced by the "JTT-1 antibody" (this monoclonal antibody was designated "JTT.2 antibody").

Since the agglutination of rat lymphocytic cells by "JTT-1 antibody" was not inhibited by antibodies against Intercellular adhesion molecule-1 (ICAM-1) or Lymphocyte function-associated antigen-1 (LFA-1), which are the most representative known cell adhesion molecules expressed on the cells, the present inventors thought that this agglutination was caused by cell adhesion through unknown adhesion molecules having that mediate cell adhesion.

Cell surface molecules (designated "JTT-1 antigen" and "JTT.2 antigen") recognized by each of these two monoclonal antibodies were then identified, isolated, and characterized.

First, the analysis of the expression patterns of "JTT-1 antigen" and "JTT.2 antigen" in various cells were analyzed by flow cytometry based on fluorescent antibody technique using "JTT-1 antibody" and "JTT-2 antibody." While both "JTT-1 antigen" and "JTT.2 antigen" were strongly expressed in activated lymphoblast cells (activated T lymphoblast cells, activated B lymphoblast cells, etc.) activated by stimulating thymocytes and spleen cells with Concanavalin A (ConA), a mitogen, in particular, in the activated lymphoblast cells, the expression was hardly found in spleen cells not stimulated at all (these cells are sometimes called "resting lymphocytes" herein). The expression patterns of molecules recognized by each of "JTT-1 antibody" and "JTT-2 antibody" were almost the same.

Using an affinity column prepared by binding "JTT-1 antibody" to adsorbents, molecules trapped by the "JTT-1 antibody", namely, "JTT-1 antigens" were purified from the mixture of soluble cell surface molecules prepared from the above-described rat lymphocytic cells. The molecular weights of these purified "JTT-1 antigens" were analyzed by immunoprecipitation using "JTT-1 antibody" and "JTT-2 antibody" and by SDS-PAGE. As a result, it was found that molecules immunoprecipitated by each of "JTT-1 antibody" and "JTT-2 antibody" were the same, and that each molecule was a homodimer having different sugar chains. Specifically, when N-linked sugar chains were not digested, the molecules were identified as one molecule with about 47 kD under non-reduction condition, and as two molecules with about 24 kD and about 28 kD under reduction condition; and when N-linked sugar chains were digested, the molecules were identified as one molecule with about 36 kD under non-reduction condition and as one molecule with about 20 kD under reduction condition.

The adhesion of rat thymocytes to the plate coated by the purified "JTT-1 antigen" was then analyzed. As a result, thymocytes significantly adhered to the plate (namely, to "JTT-1 antigen") only in the presence of "JTT-1 antibody" and that the adhesion was significantly inhibited in the co-presence of "JTT.2 antibody", indicating that "JTT-1 antigen" was the cell surface molecule mediating cell adhesion.

Next, the present inventors cloned genes encoding "JTT-1 antigen" from rat, human, and mouse, and analyzed their structures.

First, the cDNA encoding the full length of "rat JTT-1 antigen" was isolated from the cDNA library made from the lymphoblasts derived from ConA-stimulated rat spleen by expression cloning method utilizing panning method using "JTT-1 antibody" and a completely novel rat gene was isolated and identified by determining its nucleotide sequence by dideoxy method. The cDNA encoding the full length of "human JTT-1 antigen" was also isolated from the cDNA library made from ConA-stimulated human peripheral blood lymphoblasts by plaque hybridization with using the cDNA encoding "rat JTT-1 antigen" so obtained as a probe and a completely novel human gene was isolated and identified by determining its nucleotide sequence by dideoxy method. Similarly, the cDNA encoding the full length of "mouse JTT-1 antigen" was isolated from the cDNA library made from the lymphoblasts derived from ConA-stimulated mouse spleen and a completely novel mouse gene was isolated and identified by determining its nucleotide sequence by dideoxy method. Furthermore, the cDNA encoding the full length of alternative splicing variant of "rat JTT-1 antigen" mentioned above was isolated similarly from the cDNA library made from the rat thymoma cell line and another completely novel rat gene was isolated and identified by determining its nucleotide sequence by dideoxy method.

"JTT-1 antigen" was found to be a transmembrane protein (cell surface molecule) composed of a signal sequence, an extracellular region having the glycosylation site(s), a transmembrane region, and an intracellular region by hydropathy plot analysis of the amino acid sequence encoded by the isolated cDNA of "human JTT-1 antigen". Homology search with known molecules revealed that of "JTT-1 antigens" from rat, human, and mouse had no significant homology to any known molecules including cell adhesion molecules, indicating that they are novel cell surface molecules that mediates cell adhesion.

As the result that of motif search based on the amino acid sequence of "human JTT-1 antigen", it was found that "human JTT-1 antigen" had structural similarity with the above-mentioned "CD28", a cell surface molecule on lymphocytes such as T cells, which transmits costimulatory signal important for T cell activation through cell adhesion and with "CTLA-4", a cell surface molecule on lymphocytes such as T cells, which regulates the functions of activated lymphocytes such as activated T cells, cooperating with the signal.

The structural similarity is as follows.

1. 20 or more amino acid residues including cysteine residues are highly conserved.

2. Proline repeating sequence "Pro-Pro-Pro (PPP)" essential as the ligand binding region, is conserved in the extracellular region.

3. A sequence "Tyr-Xaa-Xaa-Met (YxxM)" (Xaa and x represents any amino acid) sequence essential as the signal transmitting region is conserved in the cytoplasmic region.

The locus of the gene encoding "mouse JTT-1 antigen" on mouse chromosome was found to be "1C3", which is the same location as that of mouse "CD28" and "CTLA-4" using fluorescence in situ hybridization (FISH) method.

Next, the effectiveness of therapy of autoimmune diseases and allergic diseases by regulating the function of "JTT-1 antigen", was examined by experiments in which "JTT-2 antibody" mentioned above was administered to model rats for experimental allergic encephalomyelitis (EAE) and glomerulus basement membrane (GBM) nephritis. It was found that the pathological states were significantly suppressed in both disease model animals, and that autoimmune diseases or allergic diseases can be treated by regulating the functions of "JTT-1 antigen".

It was also found that the monoclonal antibody against "human JTT-1 antigen" significantly proliferated human peripheral blood lymphocytes, and that the proliferation was further enhanced in the co-presence of a monoclonal antibody against CD3 constituting a TcR/CD3 complex on T cells, which receives the primary signal essential for T cell activation from antigen presenting cells, indicating that "JTT-1 antigen" was a cell surface molecule involved in signal transmission into lymphocytes.

Furthermore, the present inventors succeeded in producing a fusion polypeptide comprising of the extracellular region of "human JTT-1 antigen" and Fc region of human immunoglobulin. The fusion polypeptide is useful as pharmaceuticals for treating autoimmune diseases, allergic diseases, and inflammatory diseases by regulating the "JTT-1 antigen" and/or its ligand.

Moreover, the present inventors succeeded in preparing a transgenic mouse into which a gene encoding "JTT-1 antigen" of other animal species was introduced. The transgenic mouse is useful for analyzing detailed functions of "JTT-1 antigen" and for developing pharmaceuticals for treating autoimmune diseases, allergic diseases, and inflammatory diseases. The inventors also produced a knockout mouse in which the endogenous gene encoding "mouse JTT-1 antigen" was inactivated. This knockout mouse is also useful for the above-mentioned purpose.

The present inventions relate to polypeptides, genes, antibodies, vectors, transformants, pharmaceutical compositions, transgenic mice, knockout mice and so on, which are relevant to a novel mammalian "JTT-1 antigen" isolated and identified as mentioned above. Specifically, the present invention are as described in (1) to (36) below.

(1) A polypeptide constituting a cell surface molecule having characteristics mentioned below,
  (a) said cell surface molecule is expressed in at least thymocytes and mitogen-stimulated lymphoblast cells,
  (b) an antibody reactive to said cell surface molecule induces adhesion between mitogen-stimulated lymphoblast cells,
  (c) an antibody reactive to said cell surface molecule induces proliferation of peripheral blood lymphocytes under the coexistence within the presence of an antibody against CD3,
  (d) said cell surface molecule has a partial amino acid sequence represented by Phe-Asp-Pro-Pro-Pro-Phe in its extracellular region, and
  (e) said cell surface molecule has a partial amino acid sequence represented by Tyr-Met-Phe-Met in its cytoplasmic region.

(2) The polypeptide of (1) comprising the amino acid sequence of SEQ ID NO: 2 or the amino acid sequence of SEQ ID NO: 2 in which one or more amino acids are substituted, deleted, or added.

(3) The polypeptide of (1), which is encoded by a DNA hybridizing with a DNA having the nucleotide sequence of SEQ ID NO: 1 under stringent conditions.

(4) The polypeptide of (1) comprising an amino acid sequence having 60% or more homology with an amino acid sequence of SEQ ID NO: 2.

(5) The polypeptide of any one of (1) to (4) wherein said cell surface molecule is derived from human.

(6) A gene encoding the polypeptide of any one of (1) to (5).

(7) The gene of (6) wherein said gene is a cDNA.

(8) The gene of (7) wherein said cDNA has a nucleotide sequence of SEQ ID NO: 1.

(9) The gene of (7) wherein said cDNA comprises a nucleotide sequence corresponding to nucleotide residues 26 to 625 of SEQ ID NO: 3, nucleotide residues 35 to 637 of SEQ ID NO: 4, nucleotide residues 1 to 603 of SEQ ID NO: 5, or nucleotide residues 35 to 685 of SEQ ID NO: 6.

(10) A vector comprising the gene of any one of (6) to (9).

(11) A transformant into which the vector of (10) has been introduced.

(12) A transformant distinguished identified by an international deposit accession No. FERM BP-5725.

(13) A polypeptide fragment comprising an extracellular region of the polypeptide of any one of (1) to (5).

(14) The polypeptide fragment of (13) wherein said polypeptide is a human-derived polypeptide having an amino acid sequence of SEQ ID NO: 2.

(15) A gene encoding the polypeptide fragment of (13) or (14).

(16) A homodimer molecule comprising two polypeptide fragments, wherein each of the fragments comprises an extracellular region of the polypeptide of any one of (1) to (5) and said two polypeptide fragments bridged through disulfide bonds to each other.

(17) The homodimer molecule of (16) wherein said polypeptide is a human-derived polypeptide having an amino acid sequence of SEQ ID NO: 2.

(18) A pharmaceutical composition comprising either of the polypeptide fragment of (14) or the homodimer molecule of (17), or both of them, and a pharmaceutically acceptable carrier.

(19) A fusion polypeptide comprising an extracellular region of the polypeptide of any one of (1) to (5) and a constant region of a human immunoglobulin (Ig) heavy chain or a portion of the constant region.

(20) The fusion polypeptide of (19) wherein the immunoglobulin is IgG.

(21) The fusion polypeptide of (19) wherein the portion of the constant region comprises a hinge region, C2 domain, and C3 domain of IgG.

(22) The fusion polypeptide of any one of (19) to
(21) wherein said polypeptide is a human-derived polypeptide having an amino acid sequence of SEQ ID NO: 2.

(23) A homodimer molecule comprising two fusion polypeptide of any one of (19) to (22) wherein the two polypeptides bridged through disulfide bonds to each other.

(24) A homodimer molecule comprising two fusion polypeptides of (22) wherein the two polypeptides bridged through disulfide bonds to each other.

(25) A pharmaceutical composition comprising either of the fusion polypeptide of (22) or the homodimer molecule of (24), or both of them, and a pharmaceutically acceptable carrier.

(26) The pharmaceutical composition of (25) wherein said pharmaceutical composition is utilized for treating autoimmune diseases or allergic diseases, or for preventing said disease symptom.

(27) An antibody or a portion thereof reactive to the polypeptide of any one of (1) to (5), the polypeptide fragment of (13) or (14), or the cell surface molecule comprising said polypeptide.

(28) The antibody of (27) or a portion of it wherein said antibody is a monoclonal antibody.

(29) An monoclonal antibody or a portion thereof reactive to the polypeptide having an amino acid sequence of SEQ ID NO: 2, the polypeptide fragment of (14), or the human-derived cell surface molecule comprising said polypeptide.

(30) A monoclonal antibody or a portion thereof reactive to the polypeptide of any one of (1) to (5) or the cell surface molecule comprising said polypeptide, wherein the effect of said monoclonal antibody on mitogen-stimulated lymphoblast cells is substantially the same as the effect of a monoclonal antibody produced by a hybridoma identified by an international deposit accession No. FERM BP-5707 on mitogen-stimulated rat lymphoblast cells.

(31) A monoclonal antibody or a portion thereof reactive to the polypeptide of any one of (1) to (5) or the cell surface molecule comprising said polypeptide, wherein the effect of said monoclonal antibody on mitogen-stimulated lymphoblast cells is substantially the same as the effect of a monoclonal antibody produced by a hybridoma identified by an international deposit accession No. FERM BP-5708 on mitogen-stimulated rat lymphoblast cells.

(32) A pharmaceutical composition comprising the monoclonal antibody of (29) or a portion thereof and a pharmaceutically acceptable carrier.

(33) The pharmaceutical composition of (32) wherein said pharmaceutical composition is are utilized for treating autoimmune diseases or allergic diseases, or for preventing said disease symptom.

(34) A hybridoma producing the monoclonal antibody of any one of (28) to (31).

(35) A transgenic mouse in which a gene encoding the polypeptide of (1) which is a human-derived gene comprising a nucleotide sequence of SEQ ID NO: 1 or a rat-derived gene comprising a nucleotide sequence corresponding to nucleotide residues 35 to 637 of SEQ ID NO: 4, which is integrated into the mouse its endogenous gene.

(36) A knockout mouse in which its endogenous gene encoding the mouse polypeptide of claim 1 comprising the amino acid sequence encoded by the gene of SEQ ID NO: 5 is inactivated so that said mouse polypeptide is not produced.

As described above, the cell surface molecule of the present invention ("JTT-1 antigen") is involved in cell adhesion through the molecule, signal transmission into lymphocytes such as T cells, and function regulation of function of activated lymphocytes. General knowledge of lymphocytic cells, cell adhesion molecules, and the relationship between them and diseases are described below just for general understanding of these biological events but the following general knowledge is not for interpreting the present invention limitedly.

Lymphocytes are roughly classified into two kinds, T cells and B cells. After differentiation from multipotent stem cells in bone marrow to lymphoid stem cells, some of them flow into blood to reach thymus. Lymphocytes differentiated and matured in thymus, which are called T cells (Thymus-derived T cells), get into blood again, and circulate through the whole body. Matured T cells have a molecule called CD3 on their surface. The existence of CD3 molecule is an marker to determine whether the cells are matured T cells or not. CD3 is a convincing T cell marker. In addition, T cells express CD4 or CD8. T cells are classified into helper T cells (Th cells) assisting the antibody production by B lymphocytes, cytotoxic T cells (Tc cells, CTL) or killer T cells that are bound to target cells to destroy them directly, suppressor T cells that suppress the antibody production by B lymphocytes, and effector T cells that secrete effector substances such as lymphokines to cause delayed allergy.

B cells are derived from the lymphoid stem cells differentiated and matured in bone marrow. B cells are those antibody-producing precursor cells since they produce antibodies with an appropriate stimulus. B cells have immunoglobulins on their cell surface, which were produced in a cell. Such immunoglobulins function as receptors for antigens. Matured B cells have both IgM and IgD on their surface. If B cells are differentiated with antigen stimulation and signals from T cells, the production of IgM increases and their C-terminal cell membrane binding regions are changed to be secreted. With sufficient stimulation, not only the surface immunoglobulins change into IgG, IgE, and IgA, but also the immunoglobulins of each class are secreted. The immunoglobulin on the B cell surface is sometimes represented as Ig, abbreviation of surface Ig, or mIg, abbreviation of membrane Ig. All Igs on the surface of the same B cell have the same antigen binding sites.

There are lymphocytes called large granular lymphocytes (LGL) or null cells, which are neither T cells nor B cells. These cells can destroy tumor cells and virus-infected cells without pre-stimulation with antigen, which is comparative to the case of cytotoxic T cells. So, they are also called natural killer cells (NK cells).

Among the T cells mentioned above, CD4-positive T cells secrete various cytokines, newly express receptors for these cytokines, enlarge their own size, start cell dividing, and proliferate, when they react with antigen-presenting cells. Prior to these reactions at the cell level, the complex between of the antigen peptides on antigen presenting cells and MHC class II molecules binds to the corresponding T cell antigen receptor (TCR). This causes various biochemical changes in the cells, and the signal is transmitted into nuclei to start the transcription of specific DNAs and to produce respective proteins. As a result, reactions at the cell level are raised. For example, cells infected with a virus produce virus proteins and they are degraded into peptides by proteasomes in the cytoplasm. A part of the peptides enters endoplasmic reticulum through TAP, forms stable complex with MHC class I molecules just produced, and transfers to the cell surface. The peptide transferred to the cell surface is recognized specifically by CD8-positive T cells, but the T cells can not yet destroy the infected cells at this stage. These T cells reacted to with the antigen expresses IL-2 receptor (IL-2R), are differentiated into CTL cellular cytotoxicity upon IL-2 action, and destroy their target cells to kill them in the next time when they meet the same antigen peptide/MHC class I complex. Cytokines required for the differentiation into CTL are not only IL-2 but also IFNγ or other cytokines, which are thought to have similar actions. Thus, lymphokines secreted by T cells are necessary for the differentiation into CTL. The lymphokines are produced as the result that CD4-positive Th1 cells (CD4-positive T cells secreting IL-2 or INFγ) recognize the antigen peptides derived from the same virus with class II molecules. In some cases, without the help of CD4-positive T cells, CD8-positive T cells react with antigens and produce IL-2 and other cytokines. When CD8-positive T cells are differentiated into CTL, granules increase in the cytoplasm. These granules comprise various high molecular weight proteins, represented by perforin. Perforin resembles a membrane attack complex (MAC) composed of the fifth to ninth components of complement, and makes holes in the cell membrane of target cells. In addition, the granules comprise serine proteases, LT, and proteoglycan, etc. Moreover, if CD8-positive cells differentiated into CTL receive antigen stimulation, they also secrete lymphokines such as IFNγ, LT, TNF, or IL-2. Moreover, T cells show blast transformation phenomenon, when they react with hemagglutinin (phytohemagglutinin, PHA) or ConA.

Matured T cells not yet stimulated at all are called resting T cells, and have smaller cell size and shorter lifetime, a few days. When they receive stimulation, the cells enlarge as already mentioned above, and are apt to react with various kinds of stimulation. Such T cells are called activated T cells. A part of the activated T cells become memory T cells, which bring secondary immunoreaction if they receive the same antigen stimulation. Memory T cells are thought to be kept in circulating around the body for a few years or decades.

B cells not yet stimulated at all are called resting B cells like in the case of T cells, and proliferating B cells stimulated with multivalent antigens or CD40L, are called activated B cells. Since resting B cells have no costimulator molecules, which stimulate T cells with signals through TCR, such as B7-1 (CD80) or B7-2 (CD86), presenting antigens to resting T cells are thought only to stimulate TCR and to be unable to express CD40 ligands (CD40L) or produce lymphokines. Therefore, it is thought that activated helper T cells stimulated with antigen presented by other antigen-presenting cells react with the antigen presented by resting B cells. Namely, if an antigen invades, first, dendritic cells (cells having extremely dendritic projections) expressing B7 molecules or macrophages activated by reacting with microorganisms present the antigen and stimulate resting helper T cells to activate them so as to express CD40L. The activated helper T cells then bind to resting B cells presenting the same antigen and stimulate their CD40. Once B cells are activated by stimulation with multivalent antigens or CD40L, they also express B7 molecules, activate helper T cells by stimulating CD28 on their surface with TCR, and allow the helper T cells to express CD40L or produce lymphokines. B cells that show changes such as the expansion of the cell size with stimulation but not show antibody secretion are called activated B cells. If B cells so matured meet antigens, the IgM production increases together with the stimulation from T cells and the IgM molecules so produced are secreted by turning from the membrane type into secretory type. Moreover, they produce isotypic antibodies other than IgM, such as IgG upon the humoral factors from T cells. This is called isotype switching or class switching. B cells secreting antibodies are called antibody-secreting cells. A part of them becomes morphologically characteristic cells and is called a plasma cell (Knowledge of Immunology, Ohmsha, (1996)).

Incidentally, in various reactions of immune system, the subpopulation of white blood cells, namely, T lymphocytes, B lymphocytes, NK, neutrophils, etc., often show dynamics different from one another. Even the same lymphocytes as mentioned above show dynamics different from one another depending on whether the cells are activated or resting. These facts imply the existence of recognition mechanism specific to the subpopulation of white blood cells, further, recognition mechanism specific to the state of cells, and, in particular, cell adhesion molecules (cell adhesion proteins).

Cell adhesion molecules, namely, or cell adhesion proteins are, in general, the molecules that adhere cells to each other in the development and differentiation of individuals or in migration of cells to local site, and are known to be essential molecules for organic and functional contacts in a living body.

Cell adhesion molecules are roughly classified from their structural characteristics into five (5) families, immunoglobulin superfamily, integrin family, selectin family, cadherin family, and CD44 family. Adhesion molecules belonging to immunoglobulin superfamily are characterized by the existence of repeated loop-like domains formed with disulfide bonds. Examples thereof are intercellular adhesion molecule-1 "ICAM-1" and vascular cell adhesion molecule-1 "VCAM-1." In addition, adhesion molecules belonging to integrin family are characterized by α/β heterodimer structure. Examples thereof are "VLA-1 to 6" lymphocyte function-associated antigen-1 "LFA-1", "Mac-1," and "p150/90." Molecules belonging to selectin family have lectin-like domain, EGF-like domain, and complement domain in this order from N terminus. Examples thereof are "E-selectin" and "P-selectin." Examples of cadherin family are "E-cadherin," "N-cadherin," and "P-cadherin," and an example of CD44 family is "CD44".

The specific function of these adhesion molecules is known to be adhesion of white blood cells to vascular endothelial cells or of lymphocytes to antigen-presenting cells. From recent various studies, it has been gradually revealed that adhesion molecules are involved not only in these functions but also in various diseases.

In particular, there are many reports on diseases and expression abnormality of adhesion molecules. For example, as for rheumatoid arthritis (RA), the expression of both "Mac-1" and "p150/95" was reportedly strengthened in RA synoviocytes (Allen et al., Arthritis Rheum., 32:947, 1989). It has also been reported that various cells expressed "ICAM-1" strongly and ectopically on RA synovial membrane (Hale et al., Arthritis Rheum., 32:22, 1989). Another report implied that "ELAM-1" was also involved in the adhesion of neutrophils to vascular endothelial cells and that the overexpression of these molecules was involved in infiltration of neutrophils (especially, into synovial fluid), which is observed in RA synovial fluid (Laffon et al., Arthritis Rheum., 32:386, 1989). Strong expression of "CD44" in vascular endothelial cells and A-type synoviocytes on RA synovial membrane was reported (Heynes et al., Arthritis Rheum., 34:1434, 1991).

There are reports on the relationship between systemic lupus erythematosus (SLE) and the expression abnormality of adhesion molecules. For example, adhesion ability of T lymphocytes to cultured vascular endothelial cells was reportedly lowered in SLE patients, compared to healthy volunteers. In peripheral lymphocytes of SLE patients, adhesion molecules "ICAM-1", "VLA-4", and "IFA-1" to were strongly expressed (Haskard et al., Rheumatol. Int., 9:33, 1989).

In autoimmune thyroiditis diseases, it was reported that "ICAM-1" was expressed when a thyroid follicular cells were stimulated with interferon-γ, interleukin-1, and tumor necrosis factor, and that the formation of cluster of follicular cells and mononuclear cells was inhibited by anti-"ICAM-1" antibody (Weetman et al., Eur. J. Immunol., 20:271, 1990).

In hepatitis, it is thought that the chances of adhesion between hepatocytes and inflammatory cells increases since there are two pathways of adhesion, "ICAM-1" and "LFA-3", and "LFA-1" and "CD2", to thereby promote presentation of antigens and activation of inflammatory cells. In particular, in hepatitis B, "LFA-3" molecules are strongly expressed in hepatocytes, in which viruses are actively proliferating, and "ICAM-1" well correlates with the degree of hepatitis. It is thus implied that "LFA-3" is involved in the exclusion of viruses and "ICAM-1" promotes T cells to present antigen and regulates inflammation reaction. In "ICAM-1"-negative and HBc antigen-positive hepatocytes, chronic virus infection, a kind of immunounresponsiveness, may occur due to no interaction between lymphocytes and hepatocytes. It has also been reported that serum "ICAM-1" in chronic liver disease may correlate with the degree of hepatocyte damage because the serum "ICAM-1" concentrations in acute hepatitis patients, chronic active hepatitis patients, and liver cirrhosis patients were higher than that in healthy volunteers and chronic persisting hepatitis patients, and the concentration was high in the case of histologically progressing active hepatitis (Mod. Phys., 15:73-76, 1995).

In a model animal of arteriosclerosis, adhesion and invasion of monocytes and lymphocytes to vascular endothelium were observed at very early stages of the onset of the disease. It is thus thought that the interaction of these hemocytes with endothelium is the first step of the onset of arteriosclerosis. Various reports show the expression of adhesion molecules in actual arteriosclerosis nidus including the expression of "ICAM-1" in human arteriosclerosis nidus (Poston et al., Am. J. Pathol., 140:665, 1992) and the expression of "VCAM-1" in arteriosclerosis nidus of a hypercholesterolemia rabbit (Cybulsky et al., Science, 251:788, 1991). A recent report revealed that the expression of "VCAM-1" was observed in human arteriosclerosis nidus, and, in particular, strong expression in smooth muscle cells migrating to intima and in monocytes/macrophages. In addition, since the expression of "MCP-1" was enhanced in rabbit and human arteriosclerosis nidus, suggesting that "MCP-1" promotes the formation of arteriosclerosis nidus through the migration of monocytes/macrophages (Current Therapy 12:1485-1488, 1994).

The relationship between tumor metastasis and adhesion molecule abnormality has also been reported. For example, if E-cadherin-decreased cancer cells showed strong invasiveness, but the invasiveness was inhibited by introducing the cDNA of E-cadherin into the cancer cells, the invasiveness was recovered when E-cadherin antibodies antiserum was added to the cells. This suggests the tight relationship between the decrease in the expression of E-cadherin and invasiveness of tumor cells (Frixen et al., 113:173, 1991). In actual clinical cases, the relationship between the decrease of the expression of E-cadherin and metastasis is pointed out in various kinds of cancer such as hepatoma, esophageal cancer, gastric cancer, and breast cancer. It has also been reported that "VLA-4" molecules, a ligand for "VCAM-1", were highly expressed in metastatic melanoma, gastric cancer, and breast cancer, suggesting that this molecule can could be utilized for the implantation to vascular endothelial cells in metastasis. In addition, based on experiments using various tumor cell lines, it has been reported that epithelial cancer, such as gastric cancer, colon large intestine cancer, lung cancer, hepatoma, or pancreatic cancer, adhered to vascular endothelial cells through E-selectin (Takada et al., Cancer Res., 53:354, 1993).

On the other hand, therapeutic approach to treat diseases by targeting these adhesion molecules have been made. For example, it was reported that anti-rat "ICAM-1" antibody strongly inhibited inflammatory reaction in rat autoimmune arthritis model. It has also been reported that the administration of anti-"ICAM-1" antibody inhibited the onset of arthritis in adjuvant synovitis in one of animal models of RA (Nihon et al., 14:571-577, 1991). It was further reported that the metastasis formation of inoculated tumor was remarkably inhibited if a large amount of peptides having REG sequence, which is that an amino acid sequence in an extracellular matrix protein recognized and bound by some integrins, were administered to a gallbladder cancer mouse, and that in in vitro system RGD peptides and anti-β1 subunit antibody inhibited the motion and infiltration of tumor cells (Yamada et al., Cancer Res., 50:4485, 1990).

In the following, the present invention is described in detail by clarifying the meanings of terms used herein the present invention and the general production methods of polypeptides, fusion polypeptides, genes, antibodies, transgenic mice, and knockout mice of the present invention. However, it is needless to say that the meanings of the terms are not to be interpreted limitedly by the definition given herein.

"Mitogen" used herein is also called also mitogenic factor and means a substance which induces cell division. Immunologically, it means a substance inducing blastogenesis of lymphocytes polyclonally and inducing cell division. Examples thereof are lectins such as PHA and PWM, Concanavalin A (ConA), lipopolysaccharides, streptolysin S, and anti-lymphocyte antibody. It is known that Concanavalin A and PHA act only on T lymphocytes, that lipopolysaccharides act only on B lymphocytes, and that PWM acts on both lymphocytes.

The term "lymphoblast cell" used herein is also called also a large lymphocyte, lymphoblast, or immunoblast, and means a lymphocyte belonging to a large lymphocyte among lymphocytes existing in lymphoid tissues (lymph node, spleen, thymus, bone marrow, lymph duct, tonsil, etc.) and blood.

The term "activated lymphocyte" used herein, for example, a lymphocyte mentioned below, but is not limited thereto. For example, the term means a lymphocyte activated by some stimulation. As mentioned above, lymphocytes are classified into T cells, B cells, and natural killer cells. T cells are classified into CD4-positive cells and CD8-positive cells. Therefore, the "activated lymphocytes" of the present invention include mainly activated T cells, activated B cells, and activated natural killer cells, and activated T cells include activated CD4-positive cells and activated CD8-positive cells.

Upon reacting with antigens presented by antigen-presenting cells, CD4-positive T cells secrete various cytokines, newly express receptors for these cytokines, enlarge their own size, start cell dividing, proliferate, and are activated. Activated CD4-positive T cells include those in such a state.

CD8-positive T cells express IL-2R when they react with antigens. When IL-2 acts on IL-2R, the cells are differentiated into CTL, which has cellular cytotoxicity. CTL destroy their its target cells to kill them when they meet the same antigen peptide/MHC class I complex. When CD8-positive T cells are differentiated into CTL, granules increase in the cytoplasm. These granules comprise various high molecular weight proteins, represented by perforin. Perforin resembles MAC composed of the fifth to ninth components of complement, and makes holes in the cell membrane of target cells. The granules also comprise serine proteases, LT, and proteoglycan. If CD8-positive cells receive antigen stimulation and are differentiated into CTL, they also secrete lymphokines such as IFNγ, LT, TNF, or IL-2. Activated CD8-positive T cells include those in such a state.

T cells show blast formation phenomenon when they react with hemagglutinin (phytohemagglutinin, PHA) or Concanavalin A (ConA). Activated T cells comprise include those in such a state.

B cells express B7 molecules, activate helper T cells by stimulating CD28 on their surface with TCR, allow the helper T cells to express CD40L or produce lymphokines. When the cells receive stimulation, they change to expand their cell size or proliferate. Activated B cells include those in such a state. In the present invention, activated B cells include those secreting antibodies (antibody-secreting cells and plasma cells).

Activated natural killer cells mean those showing cytotoxic action on tumor cells or virus-infected cells as mentioned above. In the present invention, activated lymphocytes include thymus cells stimulated by Concanavalin A (ConA).

The "activated lymphoblast cell" used herein includes an activated "lymphoblast" that is generated when the lymphoblast mentioned above is stimulated with "mitogen" mentioned above such as Concanavalin A.

The term "resting lymphocyte" used herein, in some case, an non-activated lymphocyte, which has not received the stimulation to activate cells, in contrast to an activated lymphocyte mentioned above.

The "gene" of the present invention includes a genomic DNA and a cDNA.

The "human-derived" substance of the present invention includes natural substance isolated from a human body component (organ, tissue, cell, body fluid, etc.), and recombinant substance produced by recombinant DNA technology. When the substance is protein or polypeptide, the substance includes an artificial protein and polypeptide having an amino acid sequence where one or more amino acids are substituted, deleted, or added.

The "cell surface molecule" of the present invention is that derived from a mammal such as human, rat, mouse, guinea pig, and rabbit, preferably that derived from human, rat, or mouse, and more preferably that derived from human.

Specifically, the "cell surface molecule" of the present invention is that characterized by having, at least, properties described below.

(a) the cell surface molecule is expressed in, at least, thymocytes and mitogen-stimulated lymphoblast cells;

(b) an antibody reactive to the cell surface molecule induces adhesion between mitogen-stimulated lymphoblast cells;

(c) an antibody reactive to the cell surface molecule induces proliferation of peripheral blood lymphocytes under the coexistence within the presence of an antibody against CD3;

(d) the cell surface molecule has a partial amino acid sequence represented by Phe-Asp-Pro-Pro-Pro-Phe in its extracellular region; and (e) the cell surface molecule has a partial amino acid sequence represented by Tyr-Met-Phe-Met in its cytoplasmic region.

Preferably, the "cell surface molecule" comprises the following "polypeptide" of the present invention.

The "polypeptide" of the present invention is that which constitutes the above-mentioned "cell surface molecule" of the present invention. Examples thereof are as follows.

(1) A polypeptide encoded by a DNA hybridizing with a DNA comprising a nucleotide sequence of SEQ ID NO: 1 under stringent conditions;

(2) A polypeptide having an amino acid sequence having 60% or more homology with an amino acid sequence of SEQ ID NO: 2;

(3) A polypeptide having an amino acid sequence of SEQ ID NO: 2 or an amino acid sequence substantially the same as the amino acid sequence (namely, a polypeptide constituting "human JTT-1 antigen" and its derivative);

(4) A polypeptide having an amino acid sequence encoded by a nucleotide sequence corresponding to nucleotide residues 26 to 625 of SEQ ID NO: 3 or an amino acid sequence substantially the same as the amino acid sequence (namely, a polypeptide constituting "human JTT-1 antigen" and its derivative);

(5) A polypeptide having an amino acid sequence encoded by a nucleotide sequence corresponding to nucleotide residues 35 to 637 of SEQ ID NO: 4 or an amino acid sequence substantially the same as the amino acid sequence (namely, a polypeptide constituting "rat JTT-1 antigen" and its derivative);

(6) A polypeptide having an amino acid sequence encoded by a nucleotide sequence corresponding to nucleotide residues 1 to 603 of SEQ ID NO: 5 or an amino acid sequence substantially the same as the amino acid sequence (namely, a polypeptide constituting "mouse JTT-1 antigen" and its derivative);

(7) A polypeptide having an amino acid sequence encoded by a nucleotide sequence corresponding to nucleotide residues 35 to 685 of SEQ ID NO: 6 or an amino acid sequence substantially the same as the amino acid sequence (namely, a polypeptide constituting a "mutant of rat JTT-1 antigen" and its derivative); and (8) A polypeptide having an amino acid sequence encoded by a DNA encoding a polypeptide constituting the cell surface molecule of the present invention, wherein the DNA is introduced into the transformant identified by an international deposit accession No. FERM BP-5725 or, having amino acid sequence substantially the same as the amino acid sequence (namely, a polypeptide constituting a "human JTT-1 antigen" and its derivative).

To determine the "percent homology" of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In one embodiment the two sequences are the same length.

To determine percent homology between two sequences, the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877 is used. Such an algorithm is incorporated into the NBLAST and XBLAST programs of Altschul, et al. (1990) *J. Mol. Biol.*

215:403-410. BLAST nucleotide searches are performed with the NBLAST program, score=100, word length=12 to obtain nucleotide sequences homologous to a nucleic acid molecules of the invention. BLAST protein searches are performed with the XBLAST program, score=50, word length=3 to obtain amino acid sequences homologous to a VRK1 or VRK2 protein molecules. To obtain gapped alignments for comparison purposes, Gapped BLAST is utilized as described in Altschul et al. (1997) *Nucleic Acids Res.* 25:3389-3402. When utilizing BLAST and Gapped BLAST programs, the default parameters of the respective programs (e.g., XBLAST and NBLAST) are used. See http://www.ncbi.nlm.nih.gov.

Furthermore, the present invention relates to a DNA that specifically hybridizes under moderate or highly stringent conditions to a DNA encoding a protein of the present invention and comprises at least 15 nucleotide residues. The DNA can be used, for example, as a probe to detect or isolate a DNA encoding a protein of the present invention, or as a primer for PCR amplification. An example is DNA consisting of at least 15 nucleotides complementary to the nucleotide sequence of SEQ ID NO: 1, NO: 3, NO:4, NO:5 or NO:6.

Standard hybridization conditions (e.g., moderate or highly stringent conditions) are known to those skilled in the art and can be found in *Current Protocols in Molecular Biology*, John Wiley & Sons, N.Y. (1989), 6.3.1-6.3.6, hereby incorporated by reference. Moderate hybridization conditions are defined as equivalent to hybridization in 2× sodium chloride/sodium citrate (SSC) at 30° C., followed by one or more washes in 1×SSC, 0.1% SDS at 50-60° C. Highly stringent conditions are defined as equivalent to hybridization in 6× sodium chloride/sodium citrate (SSC) at 45° C., followed by one or more washes in 0.2×SSC, 0.1% SDS at 50-65° C.

Examples of "stringent conditions" are as follows. When a probe with 50 or more nucleotides is used and hybridization is performed in 0.9% NaCl, the standard of temperature where 50% dissociation occurs (Tm) is calculated using the following formula and the temperature for hybridization can be determined according to the following formula.

$$Tm = 82.3°\,C. + 0.41 \times (G+C)\,\% - 500/n - 0.61 \times (\text{formamide})\,\%$$

(n means the number of the nucleotide of probe). Temperature=Tm −25° C.

In addition, when a probe with 100 or more nucleotides (G+C=40 to −50%) is used, it should be considered that Tm varies as (1) and (2) mentioned below.
(1) Tm descends by about 1° C. per 1% mismatch.
(2) Tm descends by 0.6 to 0.7° C. per 1% formamide.

Accordingly, the temperature conditions for the combination of completely complementary strands can be set as follows.
(A) 65 to 75° C. (formamide not added)
(B) 35 to 45° C. (in the presence of 50% formamide)

The temperature conditions for the combination of incompletely complementary strands can be set as follows.
(A) 45 to 55° C. (formamide not added
(B) 35 to 42° C. (in the presence of 30% formamide)

The temperature conditions when a probe with 23 or less nucleotides is used can be 37° C. or can be calculated using the following formula.

$$\text{Temperature} = 2°\,C. \times (\text{the number of } A+T) + 4°\,C. \times (\text{the number of } C+G) - 5°\,C.$$

Here, "having substantially the same amino acid sequence" means to include a polypeptide having an amino acid sequence where multiple amino acids, preferably 1 to 10 amino acids, particularly preferably 1 to 5 amino acids, in the amino acid sequence shown in Sequence Listing are substituted, deleted, and/or modified, and a polypeptide having an amino acid sequence where multiple amino acids, preferably 1 to 10 amino acids, particularly preferably 1 to 5 amino acids, are added to the amino acid sequence shown in Sequence Listing, as long as the polypeptide has substantially the same biological properties as the polypeptide having the amino acid sequence shown in Sequence Listing.

Such substitution, deletion, or insertion of amino acids can be performed by the usual method (Experimental Medicine: SUPPLEMENT, "Handbook of Genetic Engineering" (1992); and so on).

Examples thereof are synthetic oligonucleotide-directed mutagenesis (gapped duplex method), point metagenesis by which a point mutation is introduced at random by treatment with nitrite or sulfite, the method by which a deletion mutant is prepared with Bal31 enzyme and the like, cassette mutagenesis, linker scanning method, miss incorporation method, mismatch primer method, DNA segment synthesis method, etc.

Synthetic oligonucleotide-directed mutagenesis (gapped duplex method) can be, for example, performed as follows. The region desired to be mutagenized is cloned into M13 phage vector having amber mutation to prepare the single-stranded phage DNA. After RF I DNA of M13 vector without amber mutation is linearized by restriction enzyme treatment, DNA is mixed with the single-stranded phage DNA mentioned above, denatured, and annealed thereby forming "gapped duplex DNA." A synthetic oligonucleotide into which mutations are introduced is hybridized with the gapped duplex DNA and the closed-circular double-stranded DNAs are prepared by the reactions with DNA polymerase and DNA ligase. *E. coli* mutS cells, deficient in mismatch repair activity, are transfected with this DNA., *E. coli* cells without suppressor activity are infected with the grown phages, and only phages without amber mutation are screened.

The method by which a point mutation is introduced with nitrite utilizes, for example, the principle as mentioned below. If DNA is treated with nitrite, bases are deaminated to change adenine into hypoxanthine, cytosine into uracil, and guanine into xanthine. If deaminated DNA is introduced into cells, "A:T" and "G:C" are replaced with "G:C" and "A:T", respectively, because hypoxanthine, uracil, and xanthine form a base pair with cytosine, adenine, and thymine, respectively, in the DNA replication. Actually, single-stranded DNA fragments treated with nitrite are hybridized with "gapped duplex DNA", and thereafter mutant strains are separated by manipulating in the same way as synthetic oligonucleotide-directed mutagenesis (gapped duplex method).

Conservative amino acid substitutions can also be made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

Alphabetical triplet or single letter codes used to represent amino acids in the present specification or figures mean amino acids as follows. (Gly/G) glycine, (Ala/A) alanine, (Val/V) valine, (Leu/L) leucine, (Ile/I) isoleucine, (Ser/S) serine, (Thr/T) threonine, (Asp/D) aspartic acid, (Glu/E) glutamic acid, (Asn/N) asparagine, (Gln/Q) glutamine, (Lys/K) lysine, (Arg/R) arginine, (Cys/C) cysteine, (Met/M) methionine, (Phe/F) phenylalanine, (Tyr/Y) tyrosine, (Trp/W) tryptophane, (His/H) histidine, (Pro/P) proline.

The "polypeptide" constituting the above-mentioned "cell surface molecule" of the present invention is a transmembrane protein, which penetrates cell membrane, and the "cell surface molecule" is composed of one or two of these transmembrane polypeptides.

Here, a "transmembrane protein" means a protein that connects with membrane through the hydrophobic peptide region penetrating the lipid bilayer of the membrane once or several times and whose structure is, as a whole, composed of three main regions, that is, extracellular region, transmembrane region, and cytoplasmic region, as seen in many receptors or cell surface molecules. Such a transmembrane protein constitutes each receptor or cell surface molecule by existing in the form of a monomer, homodimer, heterodimer or oligomer with another chain(s) having the same or different amino acid sequence.

The "polypeptide fragment" of the present invention is a fragment from the above-defined "polypeptide" of the present invention, and preferably the extracellular region of the polypeptide. One to five amino acids, if desired, can be added to the N terminus and/or C terminus of this region.

Here, an "extracellular region" means the whole or a portion from the partial structure (partial region) from the entire structure of the above-mentioned transmembrane protein where the partial structure exists outside of the membrane. In other words, it means the whole or a portion of the region of the transmembrane protein except the region integrated incorporated into the membrane (transmembrane region) and the region existing in the cytoplasm following the transmembrane region in the membrane (cytoplasmic regions).

"The constant region or a portion of the constant region of human immunoglobulin (Ig) heavy chain" used herein means the constant region or the Fc region of human-derived immunoglobulin heavy chain (H chain) as described above, or a portion of them. The immunoglobulin can be any immunoglobulin belonging to any class and any subclass. Specifically, examples of the immunoglobulin are IgG (IgG1, IgG2, IgG3, and IgG4), IgM, IgA (IgA1 and IgA2), IgD, and IgE. Preferably, the immunoglobulin is IgG (IgG1, IgG2, IgG3, or IgG4), or IgM. Examples of particularly preferable immunoglobulin in of the present invention are those belonging to human-derived IgG (IgG1, IgG2, IgG3, or IgG4).

Immunoglobulin has a Y-shaped structural unit in which four chains composed of two homologous light chains (L chains) and two homologous heavy chains (H chains) are connected through disulfide bonds (S—S bonds). The light chain is composed of the light chain variable regions (VL) and the light chain constant region (CL). The heavy chain is composed of the heavy chain variable regions (VH) and the heavy chain constant region (CH).

The heavy chain constant region is composed of some domains having the amino acid sequences inherent in each class (IgG, IgM, IgA, IgD, and IgE) and each subclass (IgG1, IgG2, IgG3, and IgG4, IgA1, and IgA2).

The heavy chain of IgG (IgG1, IgG2, IgG3, and IgG4) is composed of VH, CH1 domain, hinge region, CH2 domain, and CH3 domain in this order from N terminus.

Similarly, the heavy chain of IgG1 is composed of VH, $C\gamma_1 1$ domain, hinge region, $C\gamma_1 2$ domain, and $C\gamma_1 3$ domain in this order from N terminus. The heavy chain of IgG2 is composed of VH, $C\gamma_2 1$ domain, hinge region, $C\gamma_2 2$ domain, and $C\gamma_2 3$ domain in this order from N terminus. The heavy chain of IgG3 is composed of VH, $C\gamma_3 1$ domain, hinge region, $C\gamma_3 2$ domain, and $C\gamma_3 3$ domain in this order from N terminus. The heavy chain of IgG4 is composed of VH, $C\gamma_4 1$ domain, hinge region, $C\gamma_4 2$ domain, and $C\gamma_4 3$ domain in this order from N terminus.

The heavy chain of IgA is composed of VH, $C\alpha 1$ domain, hinge region, $C\alpha 2$ domain, and $C\alpha 3$ domain in this order from N terminus.

Similarly, the heavy chain of IgA1 is composed of VH, $C\alpha_1 1$ domain, hinge region, $C\alpha_1 2$ domain, and $C\alpha_1 3$ domain in this order from N terminus. The heavy chain of IgA2 is composed of VH, $C\alpha_2 1$ domain, hinge region, $C\alpha_2 2$ domain, and $C\alpha_2 3$ domain in this order from N terminus.

The heavy chain of IgD is composed of VH, $C\delta 1$ domain, hinge region, $C\delta 2$ domain, and $C\delta 3$ domain in this order from N terminus.

The heavy chain of IgM is composed of VH, $C\mu 1$ domain, $C\mu 2$ domain, $C\mu 3$ domain, and $C\mu 4$ domain in this order from N terminus and have no hinge region as seen in IgG, IgA, and IgD.

The heavy chain of IgE is composed of VH, $C\epsilon 1$ domain, $C\epsilon 2$ domain, $C\epsilon 3$ domain, and $C\epsilon 4$ domain in this order from N terminus and have no hinge region as seen in IgG, IgA, and IgD.

If, for example, IgG is treated with papain, it is cleaved at the slightly N terminal side beyond the disulfide bonds existing in the hinge region where the disulfide bonds connect the two heavy chains to generate two homologous Fab, in which a heavy chain fragment composed of VH and CH1 is connected with one light chain through a disulfide bond, and one Fc, in which two homologous heavy chain fragments composed of the hinge region, CH2 domain, and CH3 domain are connected through disulfide bonds (See "Immunology Illustrated", original 2nd ed., Nankodo, pp. 65-75 (1992); and "Focus of Newest Medical Science 'Recognition Mechanism of Immune System'", Nankodo, pp. 4-7 (1991); and so on).

Namely, "a portion of a constant region of immunoglobulin heavy chain" of the present invention means a portion of a constant region of an immunoglobulin heavy chain having the structural characteristics as mentioned above, and preferably, is the constant region without C1 domain, or the Fc region. Specifically, examples thereof are the region composed of hinge region, C2 domain, and C3 domain in the case from each of IgG, IgA, and IgD, and are the region composed of C2 domain, C3 domain, and C4 domain in the case from each of IgM and IgE. A particularly preferable example thereof is the Fc region of human-derived IgG1.

The "fusion polypeptide" of the present invention is that composed of the extracellular region of the "polypeptide" constituting the above-described "cell surface molecule" of the present invention and "a constant region or a portion of a constant region of human immunoglobulin (Ig) heavy chain." Preferably, it is a fusion polypeptide composed of an extracellular region of a polypeptide of the present invention and a portion of a constant region of human IgG heavy chain, and particularly preferably, it is a fusion polypeptide composed of an extracellular region of a polypeptide of the present invention and the region (Fc) composed of a hinge region, CH2 domain, and CH3 domain of human IgG heavy chain. Moreover, IgG1 is preferable among IgG. In addition, a polypeptide derived from human, mouse, or rat (preferably, human) is preferable as the polypeptide of the present invention.

The fusion polypeptide of the present invention has the advantage that the fusion polypeptide can be purified extremely easily by using affinity column chromatography using the property of protein A, which binds specifically to the immunoglobulin fragment because the fusion polypeptide of the present invention has a portion of a constant region (for example Fc) of an immunoglobulin such as IgG as mentioned above as a fusion partner. Moreover, since various antibodies against the Fc of various immunoglobulin are available, an immunoassay for the fusion polypeptides can be easily performed with antibodies against the Fc.

The polypeptide, polypeptide fragment, and fusion polypeptide of the present invention can be produced not only by recombinant DNA technology as mentioned below but also by a method well known in the art such as a chemical synthetic method and a cell culture method, or a modified method thereof.

The "gene" of the present invention comprises a DNA encoding the above-mentioned polypeptide or polypeptide fragment of the present invention, and includes any gene having a nucleotide sequence encoding the polypeptide or polypeptide fragment of the present invention.

Examples of the gene are those encoding the polypeptide or polypeptide fragment mentioned below.

(1) A polypeptide encoded by a DNA hybridizing with a DNA comprising a nucleotide sequence of SEQ ID NO: 1 under stringent conditions;

(2) A polypeptide having an amino acid sequence having 60% or more homology with an amino acid sequence of SEQ ID NO: 2;

(3) A polypeptide having an amino acid sequence of SEQ ID NO: 2 or an amino acid sequence substantially the same as the amino acid sequence (namely, a polypeptide constituting "human JTT-1 antigen" and its derivative);

(4) A polypeptide having an amino acid sequence encoded by a nucleotide sequence corresponding to nucleotide residues 26-625 of SEQ ID NO: 3 or an amino acid sequence substantially the same as the amino acid sequence (namely, a polypeptide constituting "human JTT-1 antigen" and its derivative);

(5) A polypeptide having an amino acid sequence encoded by a nucleotide sequence corresponding to nucleotide residues 35-637 of SEQ ID NO: 4 or an amino acid sequence substantially the same as the amino acid sequence (namely, a polypeptide constituting "rat JTT-1 antigen" and its derivative);

(6) A polypeptide having an amino acid sequence encoded by a nucleotide sequence corresponding to nucleotide residues 1-603 of SEQ ID NO: 5 or an amino acid sequence substantially the same as the amino acid sequence (namely, a polypeptide constituting "mouse JTT-1 antigen" and its derivative);

(7) A polypeptide having an amino acid sequence encoded by a nucleotide sequence corresponding to nucleotide residues 35-685 of SEQ ID NO: 6 or an amino acid sequence substantially the same as the amino acid sequence (namely, a polypeptide constituting a "mutant of rat JTT-1 antigen" and its derivative); and (8) A polypeptide having an amino acid sequence encoded by a DNA encoding a polypeptide constituting the cell surface molecule of the present invention, wherein the DNA is introduced into the transformant identified by an international deposit accession No. FERM BP-5725 or, having an amino acid sequence substantially the same as said amino acid sequence (namely, a polypeptide constituting a "human JTT-1 antigen" and its derivative).

Here, "substantially the same amino acid sequence" means as defined above.

Specific examples of the gene of the present invention are DNAs or their fragments mentioned below.

(1) A DNA comprising a nucleotide sequence of SEQ ID NO: 1, and a DNA hybridizing with the DNA under stringent conditions;

(4) A DNA comprising a nucleotide sequence corresponding to nucleotide residues 26-625 of SEQ ID NO: 3;

(5) A DNA comprising a nucleotide sequence corresponding to nucleotide residues 35-637 of SEQ ID NO: 4;

(6) A DNA comprising a nucleotide sequence corresponding to nucleotide residues 1-603 of SEQ ID NO: 5;

(7) A DNA comprising a nucleotide sequence corresponding to nucleotide residues 35-685 of SEQ ID NO: 6;

(8) A DNA encoding a polypeptide constituting a cell surface molecule of the present invention, wherein the DNA is introduced into a transformant identified by an international deposit accession No. FERM BP-5725.

The DNA encoding a portion of a constant region of immunoglobulin heavy chain, which is a part of a fusion polypeptide of the present invention, can be cDNA, or genomic DNA comprised of intons between every exon (the DNA encoding, for example, CH1 domain, hinge region, CH2 domain, CH3 domain, CH4 domain and so on).

The DNA of the present invention includes any DNA comprised of any codons as long as the codons encode the same amino acids.

The DNA of the present invention can be a DNA obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

The DNA encoding the polypeptide of the present invention can be obtained by the usual method such as a method to clone cDNA from mRNA encoding the polypeptide of the present invention, a method to isolate genomic DNA and then splice them, chemical synthesis and so on.

(1) cDNA can be cloned from the mRNA encoding the polypeptide of the present invention by, for example, the method described below.

First, the mRNA encoding a cell surface molecule (polypeptide) of the present invention is prepared from tissues or cells (for example, thymus cells or spleen-derived lymphoblast cells stimulated with ConA) expressing and producing a cell surface molecule (polypeptide) of the present invention. mRNA can be prepared isolating total RNA by a known method such as quanidine-thiocyanate method (Chirgwin et al., Biochemistry, 18:5294, 1979), hot phenol method, or AGPC method, and subjecting it to affinity chromatography using oligo-dT cellulose or poly-U Sepharose.

Then, with the mRNA obtained as a template, cDNA is synthesized, for example, by a well-known method using reverse transcriptase such as the method of Okayama et al. (Mol. Cell. Biol. 2:161, 1982; ibid. 3:280, 1983) or the method of Hoffman et al. (Gene 25:263, 1983), and converted into double-stranded cDNA. A cDNA library is prepared by transforming *E. coli* with plasmid vectors, phage vectors, or cosmid vectors having this cDNA or by transfecting *E. coli* after in vitro packaging.

The plasmid vectors used in this invention are not limited as long as they are replicated and maintained in hosts. Any phage vectors that can be replicated in hosts can also be used.

Examples of usually used cloning vectors are pME18S, λZA-PII (lZAPII), pUC19, λgt10, λgt11, and so on. When the vector is applied to immunological screening as mentioned below, the vector having a promoter that can express a gene encoding the polypeptide of the present invention in a host is preferably used.

cDNA can be inserted into a plasmid by, for example, the method of Maniatis et al. (Molecular Cloning, A Laboratory Manual, second edition, Cold Spring Harbor Laboratory, p. 1.53, 1989). cDNA can be inserted into a phage vector by, for example, the method of Hyunh et al. (DNA cloning, a practical approach, Vol. 1, p. 49 (1985)). These methods can be simply performed by using a commercially available cloning kit (for example, a product from Takara Shuzo). The recombinant plasmid or phage vector thus obtained is introduced into appropriate host cells such as a prokaryote (for example, E. coli: XL1Blue MRF', DH5α, HB101, MC1061/P3, etc.).

Examples of a method for introducing a plasmid into a host are calcium chloride method, calcium chloride/rubidium chloride method described in Molecular Cloning, A Laboratory Manual (second edition, Cold Spring Harbor Laboratory, p. 1.74 (1989)), and electroporation method. Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham).

The cDNA encoding the polypeptide of the present invention can be isolated from the cDNA library so prepared according to the method mentioned above by combining general cDNA screening methods.

For example, a clone comprising the desired cDNA can be screened by a known colony hybridization method (Crunstein et al., Proc. Natl. Acad. Sci. USA, 72:3961, 1975) or plaque hybridization method (Molecular Cloning, A Laboratory Manual, second edition, Cold Spring Harbor Laboratory, p. 2.108 (1989)) using $^{32}$P-labeled chemically synthesized oligonucleotides as probes, which are corresponding to the amino acid sequence of the polypeptide of the present invention. Alternatively, a clone having a DNA fragment encoding a specific region within the polypeptide of the present invention can be screened by amplifying the region by PCR with synthetic PCR primers.

When a cDNA library prepared using a cDNA expression vector (for example, λZAPII phage vector) is used, the desired clone can be screened by the antigen-antibody reaction using an antibody against the polypeptide of the present invention. A screening method using PCR method is preferably used when many clones are subjected to screening.

The nucleotide sequence of the DNA thus obtained can be determined by Maxam-Gilbert method (Maxam et al., Proc. Natl. Acad. Sci. USA, 74:560, 1977) or the dideoxynucleotide synthetic chain termination method using phage M13 (Sanger et al., Proc. Natl. Acad. Sci. USA, 74:5463-5467, 1977). The whole or a portion of the gene encoding the polypeptide of the present invention can be obtained by excising the clone obtained as mentioned above with restriction enzymes and so on.

(2) The DNA encoding the polypeptide of the present invention can be isolated from the genomic DNA derived from the cells expressing the polypeptide of the present invention as mentioned above by the following methods.

Such cells are solubilized preferably by SDS or proteinase K, and the DNAs are deproteinized by repeating phenol extraction. RNAs are digested preferably with ribonuclease. The DNAs obtained are partially digested with appropriate restriction enzymes, and the DNA fragments obtained are amplified with appropriate phage or cosmid to generate a library. Then, clones having the desired sequence are detected, for example, by using radioactively labeled DNA probes, and the whole or a portion of the gene encoding the polypeptide of the present invention is obtained from the clones by excision with restriction enzyme and so on.

cDNA encoding a human-derived polypeptide can be obtained as follows. After a cosmid library into which human genomic DNA (chromosomal DNA) is introduced is prepared ("Laboratory Manual: Human Genome Mapping", Maruzen press), positive clones comprising the DNA of the coding region of the desired protein are obtained by screening the cosmid library. Then, the cDNA library mentioned above is screened with the coding DNA excised from the positive clone as a probe to prepare the human cDNA.

(3) The DNA of the present invention can also be chemically synthesized by the usual method, based on the nucleotide sequence of SEQ ID NO: 1, 3, 4, 5, or 6.

The present invention also relates to a recombinant vector comprising the DNA encoding an above-mentioned cell surface molecule (polypeptide) of the present invention. The recombinant vector of the present invention is not limited as long as it can be replicated and maintained or can autonomously replicate in various prokaryotic and/or eukaryotic hosts. The vector of the present invention includes plasmid vectors and phage vectors.

The recombinant vector can easily be prepared by ligating the DNA encoding the polypeptide of the present invention with a vector for recombination available in the art (plasmid DNA and bacteriophage DNA) by the usual method. Specific examples of the vectors for recombination used are E. coli-derived plasmids such as pBR322, pBR325, pUC12, pUC13, and pUC19, yeast-derived plasmids such as pSH19 and pSH15, and Bacillus subtilis-derived plasmids such as pUB110, pTP5, and pC194. Examples of phages are a bacteriophage such as λ phage, and an animal or insect virus (pVL1393, Invitrogen) such as a retrovirus, vaccinia virus, and nuclear polyhidrosis virus.

An expression vector is useful for expressing the DNA encoding the polypeptide of the present invention and for producing the polypeptide of the present invention. The expression vector is not limited as long as it expresses the gene encoding the polypeptide of the present invention in various prokaryotic and/or eukaryotic host cells and produces this protein. Examples thereof are pEFneo (Proc. Natl. Acad. Sci. USA 91:158-162, 1994), pEF-BOS (Nucleic Acids Res. 18:5322, 1990), pME18S (Experimental Medicine: SUPPLEMENT, "Handbook of Genetic Engineering" (1992)), pMAL C2, and so on.

When bacteria, particularly E. coli are used as host cells, an expression vector is generally comprised of, at least, a promoter/operator region, an initiation codon, the DNA encoding the polypeptide of the present invention, termination codon, terminator region, and replicon.

When yeast, animal cells, or insect cells are used as hosts, an expression vector is preferably comprised of, at least, a promoter, an initiation codon, the DNA encoding the polypeptide of the present invention, and a termination codon. It may also comprise the DNA encoding a signal peptide, enhancer sequence, 5'- and 3'-untranslated region of the gene encoding the polypeptide of the present invention, splicing junctions, polyadenylation site, selectable marker region, and replicon. The expression vector may also contain, if required, a gene for gene amplification (marker) that is usually used.

A promoter/operator region to express the polypeptide of the present invention in bacteria comprises a promoter, an operator, and a Shine-Dalgarno (SD) sequence (for example, AAGG). For example, when the host is *Escherichia*, it preferably comprises Trp promoter, lac promoter, recA promoter, λPL promoter, lpp promoter, tac promoter, or the like. Examples of a promoter to express the polypeptide of the present invention in yeast are PHO5 promoter, PGK promoter, GAP promoter, ADH promoter, and so on. When the host is *Bacillus*, examples thereof are SL01 promoter, SP02 promoter, penP promoter and so on. When the host is a eukaryotic cell such as a mammalian cell, examples thereof are SV40-derived promoter, retrovirus promoter, heat shock promoter, EF promoter, and so on, and preferably SV-40, SRα, and retrovirus-derived one. As a matter of course, the promoter is not limited to the above examples. In addition, to use an enhancer is effective for expression.

A preferable initiation codon is, for example, a methionine codon (ATG).

The commonly used termination codon (for example, TAG, TGA, TAA, and so on) is illustrated as a termination codon.

Usually used natural or synthetic terminators are used as a terminator region.

A replicon means a DNA capable of replicating the whole DNA sequence in host cells, and includes a natural plasmid, an artificially modified plasmid (DNA fragment prepared from a natural plasmid), a synthetic plasmid, and so on. Examples of a preferable plasmids are pBR322 or its artificial derivatives (DNA fragment obtained by treating pBR322 with appropriate restriction enzymes) for *E. coli*, yeast 2μ plasmid or yeast chromosomal DNA for yeast, and pEFneo, pME18S, pRSVneo ATCC 37198, pSV2dhfr ATCC 37145, pdBPV-MMTneo ATCC 37224, pSV2neo ATCC 37149, etc., for mammalian cells.

An enhancer sequence, polyadenylation site, and splicing junction that are usually used in the art, such as those derived from SV40 can be also used.

A selectable marker usually used can be used according to the usual method. Examples thereof are resistance genes for antibiotics, such as tetracycline, neomycin, ampicillin, or kanamycin, and thymidine kinase gene.

Examples of a gene for gene amplification are dihydrofolate reductase (DHFR) gene, thymidine kinase gene, neomycin resistance gene, glutamate synthase gene, adenosine deaminase gene, ornithine decarboxylase gene, hygromycin-B-phophotransferase gene, aspartate transcarbamylase gene, etc.

The expression vector of the present invention can be prepared by continuously and circularly linking at least the above-mentioned promoter, initiation codon, DNA (gene) encoding the polypeptide of the present invention, termination codon, and terminator region, to an appropriate replicon. If desired, appropriate DNA fragments (for example, linkers, restriction sites generated with other restriction enzyme), can be used by the usual method such as digestion with a restriction enzyme or ligation using T4 DNA ligase.

Transformants of the present invention can be prepared by introducing the expression vector mentioned above into host cells.

Host cells used in the present invention are not limited as long as they are compatible with an expression vector mentioned above and can be transformed. Examples thereof are various cells such as natural cells or artificially established recombinant cells usually used in technical field of the present invention (for example, bacteria (*Escherichia* and *Bacillus*), yeast (*Saccharomyces*, *Pichia*, etc.), animal cells, or insect cells.

*E. coli* or animal cells are preferably used. Specific examples are *E. coli* (DH5α, XL1Blue MRF', TB1, HB101, etc.), mouse-derived cells (COP, L, C127, Sp2/0, NS-1, NIH 3T3, etc.), rat-derived cells, hamster-derived cells (BHK, CHO-K1, CHO, etc.), monkey-derived cells (COS1, COS3, COS7, CV1, Velo, etc.), and human-derived cells (HEK293, Hela, diploid fibroblast-derived cells, myeloma, Namalwa, etc.).

An expression vector can be introduced (transformed (transduced)) into host cells by known method.

Transformation can be performed, for example, according to the method of Cohen et al. (Proc. Natl. Acad. Sci. USA 69:2110, 1972), protoplast method (Mol. Gen. Genet. 168: 111, 1979), or competent method (J. Mol. Biol. 56:209, 1971) when the hosts are bacteria (*E. coli*, *Bacillus subtilis*, etc.), the method of Hinnen et al. (Proc. Natl. Acad. Sci. USA 75:1927, 1978), or lithium method (J. Bacteriol. 153:163, 1983) when the host is *Saccharomyces cerevisiae*, the method of Graham (Virology 52:456, 1973) when the hosts are animal cells, and the method of Summers et al. (Mol. Cell. Biol. 3:2156-2165, 1983) when the hosts are insect cells.

The polypeptide of the present invention can be produced by cultivating transformants (in the following this term includes transductants) comprising an expression vector prepared as mentioned above in nutrient media.

The nutrient media preferably comprise carbon source, inorganic nitrogen source, or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meet extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, etc.).

Cultivation is performed by a method known in the art. Cultivation conditions such as temperature, pH of the media, and cultivation time are selected appropriately so that the polypeptide of the present invention is overproduced.

Specific media and cultivation conditions used depending on host cells are illustrated below, but are not limited thereto.

When the hosts are bacteria, actinomycetes, yeasts, filamentous fungi, liquid media comprising the nutrient source mentioned above are appropriate. The media with pH 5 to 8 are preferably used.

When the host is *E. coli*, examples of preferable media are LB media, and M9 media (Miller et al., Exp. Mol. Genet., Cold Spring Harbor Laboratory, p. 431 (1972)). Using these media, cultivation can be performed usually at 14 to 43° C. for about 3 to 24 hours with aeration and stirring, if necessary.

When the host is *Bacillus*, cultivation can be performed usually at 30 to 40° C. for about 16 to 96 hours with aeration and stirring, if necessary.

When the host is yeast, examples of media are Burkholder minimal media (Bostian, Proc. Natl. Acad. Sci. USA, 77:4505, 1980). The pH of the media is preferably 5 to 8. Cultivation can be performed usually at 20 to 35° C. for about 14 to 144 hours with aeration and stirring, if necessary.

When the host is an animal cell, examples of media are MEM media containing about 5 to 20% fetal bovine serum (Science 122:501, 1952), DMEM media (Virology 8:396, 1959), RPMI1640 media (J. Am. Med. Assoc. 199:519, 1967), and 199 media (Proc. Soc. Exp. Biol. Med. 73:1, 1950). The pH of the media is preferably about 6 to 8. Cultivation can be performed usually at about 30 to 40° C. for about 15 to 72 hours with aeration and stirring, if necessary.

When the host is an insect cell, an example of media is Grace's media containing fetal bovine serum (Proc. Natl. Acad. Sci. USA 82:8404, 1985). The pH thereof is preferably about 5 to 8. Cultivation can be performed usually at about 20 to 40° C. for 15 to 100 hours with aeration and stirring, if necessary.

Cultivation of transformants as mentioned above, in particular animal cells can overexpress the polypeptide of the present invention on the surface of the cells.

The polypeptide of the present invention can be produced as a soluble polypeptide fragment such as an extracellular region fragment by preparing the transformants as mentioned above using the DNA encoding the extracellular region or each domain and by cultivating the transformants to allow them to secrete the soluble polypeptide into the culture supernatant. In addition, a fusion polypeptide of the present invention can be prepared similarly.

Namely, a culture filtrate (supernatant) is obtained by the method such as filtration or centrifugation of the obtained culture, and the polypeptide or polypeptide fragment of the present invention is purified and isolated from the culture filtrate by the usual method commonly used in order to purify and isolate a natural or synthetic protein.

Examples of the isolation and purification method are a method utilizing solubility, such as salting out and solvent precipitation method, a method utilizing the difference in molecular weight, such as dialysis, ultrafiltration, gel filtration, and sodium dodecyl sulfate-polyacrylamide gel electrophoresis, a method utilizing charges, such as ion exchange chromatography and hydroxylapatite chromatography, a method utilizing specific affinity, such as affinity chromatography, a method utilizing the difference in hydrophobicity, such as reverse phase high performance liquid chromatography, and a method utilizing the difference in isoelectric point, such as isoelectric focusing.

When the polypeptide or a polypeptide fragment of the present invention exists in the periplasm or cytoplasm of cultured transformants, first, the fungus bodies or cells are harvested by the usual method such as filtration or centrifugation and suspended in appropriate buffer. After the cell wall and/or cell membrane of the cells and so on are disrupted by the method such as lysis with sonication, lysozyme, and freeze-thawing, the membrane fraction comprising the polypeptide of the present invention is obtained by the method such as centrifugation or filtration. The membrane fraction is solubilized with a detergent such as Triton-X100 to obtain the crude extract. Finally, the polypeptide or the polypeptide fragment is isolated and purified from the crude extract by the usual method as illustrated above.

The "transgenic mouse" of the present invention is a transgenic mouse wherein the DNA (cDNA or genomic DNA) prepared as mentioned above encoding the polypeptide of the present invention derived from animals except mice (non-self polypeptide) have been integrated into its endogenous locus of the mouse. The transgenic mouse expresses the non-self polypeptide and secretes the polypeptide into its body.

The transgenic mouse can be prepared according to the method as usually used for producing a transgenic animal (for example, see "Newest Manual of Animal Cell Experiment", LIC press, Chapter 7, pp. 361-408, (1990)).

Specifically, for example, embryonic stem cells (ES cells) obtained from normal mouse blastocysts are transformed with an expression vector in which the gene encoding human-derived polypeptide of the present invention (i.e., "human JTT-1 antigen") has been operably inserted. ES cells in which the gene encoding the human-derived polypeptide of the present invention has been integrated into the endogenous gene are screened by the usual method. Then, the ES cells screened are microinjected into a fertilized egg obtained from another normal mouse (blastocyst) (Proc. Natl. Acad. Sci. USA 77:7380-7384, 1980; U.S. Pat. No. 4,873,191). The blastocyst is transplanted into the uterus of another normal mouse as the foster mother. Then, founder mice (progeny mice) are born from the foster mother mouse. By mating the founder mice with normal mice, heterogeneic transgenic mice are obtained. By mating the heterogeneic transgenic mice with each other, homogenetic transgenic mice are obtained according to Mendel's laws.

Knockout mouse of the present invention is a mouse wherein the endogenous gene encoding the mouse-derived polypeptide of the present invention (i.e., "mouse JTT-1 antigen") has been knocked out (inactivated). It can be prepared, for example, by positive-negative selection method in which homologous recombination is applied (U.S. Pat. Nos. 5,464,764; 5,487,992; and 5,627,059; Proc. Natl. Acad. Sci. USA 86:8932-8935, 1989; Nature 342:435-438, 1989; etc.).

The "antibody" of the present invention can be a polyclonal antibody (antiserum) or a monoclonal antibody, and preferably a monoclonal antibody.

Specifically, it is an antibody reactive to (against, which binds to) the above-mentioned polypeptide or polypeptide fragment of the present invention.

The antibody of the present invention can be natural antibodies obtained by immunizing mammals such as mice, rats, hamsters, guinea pigs, and rabbits with the antigen, such as cells (natural cells, cell lines, tumor cells, etc.) expressing "cell surface molecules" of the present invention, transformants overexpressing the polypeptide or cell surface molecules of the present invention on the surface thereof prepared using recombinant DNA technology on the cell surface, or "polypeptide fragments" or "fusion polypeptides" of the present invention. The antibody of the present invention also includes chimeric antibodies and humanized antibodies (CDR-grafted antibodies) that can be produced by recombinant DNA technology, and human antibodies that can be produced using human antibody-producing transgenic animals.

The monoclonal antibody includes those having any one isotype of IgG, IgM, IgA, IgD, or IgE. IgG or IgM is preferable.

The polyclonal antibody (antisera) or monoclonal antibody of the present invention can be produced by the known methods. Namely, a mammal, preferably, a mouse, rat, hamster, guinea pig, rabbit, cat, dog, pig, goat, horse, or cattle, or more preferably, a mouse, rat, hamster, guinea pig, or rabbit is immunized, for example, with an antigen mentioned above with Freund's adjuvant, if necessary.

The polyclonal antibody can be obtained from the antiserum obtained from the animal so immunized. In addition, the monoclonal antibodies are produced as follows. Hybridomas are prepared from the antibody-producing cells obtained from the animal so immunized and myeloma cells that are not capable of producing autoantibodies. The hybridomas are cloned, and clones producing the monoclonal antibodies showing the specific affinity to the antigen used for immunizing the mammal are screened.

Specifically, the monoclonal antibody can be produced as follows. Immunizations are performed by injecting or implanting once or several times the antigen as mentioned above as an immunogen, if necessary, with Freund's adjuvant, subcutaneously, intramuscularly, intravenously, through the footpad, or intraperitoneally into a non-human mammal, specifically a mouse, rat, hamster, guinea pig, or rabbit, preferably a mouse, rat, or hamster (including a transgenic animal generated so as to produce antibodies derived from another animal such as the transgenic mouse producing human antibody mentioned below). Usually, immunizations are performed once to four times every one to fourteen days after the first immunization. Antibody-producing cells are obtained from the mammal so immunized in about one to five days after the last immunization. The frequency and interval of immunizations can be appropriately arranged depending on property of the immunogen used. Hybridomas that secrete a monoclonal antibody can be prepared by the method of Köhler and Milstein (Nature 256:495-497, 1975) and by its modified method. Namely, hybridomas are prepared by fusing antibody-producing cells contained in a spleen, lymph node, bone marrow, or tonsil obtained from the non-human mammal immunized as mentioned above, preferably a spleen, with myelomas without autoantibody-producing ability, which are derived from, preferably, a mammal such as a mouse, rat, guinea pig, hamster, rabbit, or human, or more preferably, a mouse, rat, or human.

For example, mouse-derived myeloma P3/X63-AG8.653 (653), P3/NSI/1-Ag4-1 (NS-1), P3/X63-Ag8.U1 (P3U1), SP2/0-Ag14 (Sp2/0, Sp2), PAI, F0, or BW5147, rat-derived myeloma 210RCY3-Ag.2.3., or human-derived myeloma U-266AR1, GM1500-6TG-A1-2, UC729-6, CEM-AGR, D1R11, or CEM-T15 can be used as a myeloma used for the cell fusion.

Hybridoma clones producing monoclonal antibodies can be screened by cultivating hybridomas, for example, in microtiter plates and by measuring the reactivity of the culture supernatant in the well in which hybridoma growth is observed, to the immunogen used for the immunization mentioned above, for example, by enzyme immunoassay such as RIA and ELISA.

The monoclonal antibodies can be produced from hybridomas by cultivating the hybridomas in vitro or in vivo such as in the ascites fluid of a mouse, rat, guinea pig, hamster, or rabbit, preferably a mouse or rat, more preferably mouse and isolating the antibodies from the resulting the culture supernatant or ascites fluid of a mammal.

Cultivating hybridomas in vitro can be performed depending on the property of cells to be cultured, on the object of a test study, and on the various conditions of a cultivating method, by using known nutrient media or any nutrient media derived from known basal media for growing, maintaining, and storing the hybridomas to produce monoclonal antibodies in culture supernatant.

Examples of basal media are low calcium concentration media such as Ham'F12 medium, MCDB153 medium, or low calcium concentration MEM medium, and high calcium concentration media such as MCDB104 medium, MEM medium, D-MEM medium, RPMI1640 medium, ASF104 medium, or RD medium. The basal media can contain, for example, sera, hormones, cytokines, and/or various inorganic or organic substances depending on the objective.

Monoclonal antibodies can be isolated and purified from the culture supernatant or ascites fluid mentioned above by saturated ammonium sulfate precipitation, euglobulin precipitation method, caproic acid method, caprylic acid method, ion exchange chromatography (DEAE or DE52), affinity chromatography using anti-immunoglobulin column or protein A column.

Preferable examples of monoclonal antibodies of the present invention are as follows.

(1) A monoclonal antibody reactive to a polypeptide having an amino acid sequence of SEQ ID NO: 2, a polypeptide fragment derived from the polypeptide, or a human-derived cell surface molecule composed of the polypeptide;

(2) A monoclonal antibody reactive to a polypeptide of the present invention, a polypeptide fragment derived from the polypeptide, or a cell surface molecule composed of the polypeptide, wherein the effect of the monoclonal antibody on mitogen-stimulated lymphoblast cells is substantially the same as the effect of a monoclonal antibody produced by a hybridoma identified by an international deposit accession No. FERM BP-5707 on mitogen-stimulated rat lymphoblast cells; and (3) A monoclonal antibody reactive to a polypeptide of the present invention, a polypeptide fragment derived from the polypeptide, or a cell surface molecule composed of the polypeptide, wherein the effect of the monoclonal antibody on mitogen-stimulated lymphoblast cells is substantially the same as the effect of a monoclonal antibody produced by a hybridoma identified by an international deposit accession No. FERM BP-5708 on mitogen-stimulated rat lymphoblast cells.

In addition, the monoclonal antibody of the present invention includes that produced by the hybridoma identified by an international deposit accession No. FERM BP-5707 or No. FERM BP-5708.

The "chimeric monoclonal antibody" of the present invention is a monoclonal antibody prepared by genetic engineering, and specifically means a chimeric antibody such as mouse/human chimeric monoclonal antibody whose variable regions are derived from immunoglobulin of an non-human mammal (mouse, rat, hamster, etc.) and whose constant regions are derived from human immunoglobulin.

The constant region derived from human immunoglobulin has the amino acid sequence inherent in each isotype such as IgG (IgG1, IgG2, IgG3, IgG4), IgM, IgA, IgD, and IgE. The constant region of the recombinant chimeric monoclonal antibody of the present invention can be that of human immunoglobulin belonging to any isotype. Preferably, it is the constant region of human IgG.

The chimeric monoclonal antibody of the present invention can be produced, for example, as follows. Needless to say, the production method is not limited thereto.

A mouse/human chimeric monoclonal antibody can be prepared, referring to Experimental Medicine: SUPPLEMENT, Vol. 1.6, No. 10 (1988); and examined published Japanese patent application (JP-B) No. Hei 3-73280. Namely, it can be prepared by operably inserting CH gene (C gene encoding the constant region of H chain) obtained from the DNA encoding human immunoglobulin downstream of active VH genes (rearranged VDJ gene encoding the variable region of H chain) obtained from the DNA encoding a mouse monoclonal antibody isolated from the hybridoma producing the mouse monoclonal antibody, and CL gene (C gene encoding the constant region of L chain) obtained from the DNA encoding human immunoglobulin downstream of active VL genes (rearranged VJ gene encoding the variable region of L chain) obtained from the DNA encoding the mouse monoclonal antibody isolated from the hybridoma, into the same or different vectors so as for them to be expressed, following by transforming host cells with the expression vector, and then by cultivating the transformants.

Specifically, DNAs are first extracted from mouse monoclonal antibody-producing hybridomas by the usual method, digested with appropriate restriction enzymes (for example, EcoRI and HindIII), electrophoresed (using, for example, 0.7% agarose gel), and analyzed by Southern blotting. After an electrophoresed gel is stained, for example, with ethidium bromide and photographed, the gel is given with marker positions, washed twice with water, and soaked in 0.25 M HCl for 15 minutes. Then, the gel is soaked in 0.4 N NaOH solution for 10 minutes with gently stirring. The DNAs are transferred to a filter for 4 hours by the usual method. The filter is recovered and washed twice with 2×SSC. After the filter is sufficiently dried, it is baked at 75° C. for 3 hours. After baking, the filter is treated with 0.1×SSC/0.1% SDS at 65° C. for 30 minutes. Then, it is soaked in 3×SSC/0.1 SDS. The filter obtained is treated with prehybridization solution in a plastic bag at 65° C. for 3 to 4 hours.

Next, $^{32}$P-labeled probe DNA and hybridization solution are added to the bag and reacted at 65° C. about 12 hours. After hybridization, the filter is washed under appropriate salt concentration, reaction temperature, and time (for example, 2×SSC-0.1% SDS, room temperature, 10 minutes). The filter is put into a plastic bag with a little 2×SSC, and subjected to autoradiography after the bag is sealed.

Rearranged VDJ gene and VJ gene encoding H chain and L chain of a mouse monoclonal antibody are identified by Southern blotting mentioned above. The region comprising the identified DNA fragment is fractioned by sucrose density gradient centrifugation and inserted into a phage vector (for example, Charon 4A, Charon 28, λEMBL3, λEMBL4, etc.). E. coli (for example, LE392, NM539, etc.) is transformed with the phage vector to generate a genomic library. The genomic library is screened by plaque hybridization such as Benton-Davis method (Science 196:180-182, 1977) using appropriate probes (H chain J gene, L chain (κ) J gene, etc.) to obtain positive clones comprising rearranged VDJ gene or VJ gene. By making the restriction map and determining the nucleotide sequence of the clones obtained, it is confirmed that genes comprising the desired, rearranged VH (VDJ) gene or VL (VJ) gene are obtained.

Separately, human CH gene and human CL gene used for chimerization are isolated. For example, when a chimeric5 antibody with human IgG1 is produced, Cγ1 gene was a CH gene, and Cκ gene as a CL gene, are isolated. These genes can be isolated from human genomic library with mouse Cγ1 gene and mouse Cκ gene, corresponding to human Cγ1 gene and human Cκ gene, respectively, as probes, taking advantage of high homology between the nucleotide sequences of mouse immunoglobulin gene and that of human immunoglobulin gene.

Specifically, DNA fragments comprising human Cκ gene and an enhancer region are isolated from human λ Charon 4A HaeIII-AluI genomic library (Cell 15:1157-1174, 1978), for example, with a 3 kb HindIII-BamHI fragment of clone Ig146 (Proc. Natl. Acad. Sci. USA 75:4709-4713, 1978) and a 6.8 kb EcoRI fragment of clone MEP10 (Proc. Natl. Acad. Sci. USA 78:474-478, 1981) as probes. In addition, for example, after human fetal hepatocyte DNA is digested with HindIII and fractioned by agarose gel electrophoresis, a 5.9 kb fragment is inserted into λ788 and then human Cγ1 gene is isolated with the probes mentioned above.

Using mouse VH gene, mouse VL gene, human CH gene, and human CL gene so obtained, and taking promoter region and enhancer region into consideration, human CH gene is inserted downstream mouse VH gene and human CL gene is inserted downstream mouse VL gene into an expression vector such as pSV2gpt or pSV2neo with appropriate restriction enzymes and DNA ligase by the usual method. In this case, chimeric genes of mouse VH gene/human CH gene and mouse VL gene/human CL gene can be respectively inserted in the same expression vector or in different expression vectors.

Chimeric gene-inserted expression vector(s) thus prepared are introduced into myelomas that do not produce antibodies, for example, P3X63◦Ag8◦653 cells or SP210 cells by protoplast fusion method, DEAE-dextran method, calcium phosphate method, or electroporation method. The transformants are screened by cultivating in media containing a drug corresponding to the drug resistance gene inserted into the expression vector and, then, cells producing desired chimeric monoclonal antibodies are obtained.

Desired chimeric monoclonal antibodies are obtained from the culture supernatant of antibody-producing cells thus screened.

The "humanized monoclonal antibody (CDR-grafted antibody)" of the present invention is a monoclonal antibody prepared by genetic engineering and specifically means a humanized monoclonal antibody wherein a portion or the whole of the complementarity determining regions of the hypervariable region are derived from the complementarity determining regions of the hypervariable region from a monoclonal antibody of an non-human mammal (mouse, rat, hamster, etc.), the framework regions of the variable region are derived from the framework regions of the variable region from human immunoglobulin, and the constant region is derived from human a constant region from immunoglobulin.

The complementarity determining regions of the hypervariable region exists in the hypervariable region in the variable region of an antibody and means three regions which directly and complementary binds to an antigen (complementarity-determining residues, CDR1, CDR2, and CDR3). The framework regions of the variable region means four comparatively conserved regions lying upstream, downstream or between the three complementarity determining regions (framework region, FR1, FR2, FR3, and FR4).

In other words, a humanized monoclonal antibody means that in which the whole region except a portion or the whole of the complementarity determining regions of the hypervariable region of a nonhuman mammal-derived monoclonal antibody have been replaced with their corresponding regions derived from human immunoglobulin.

The constant region derived from human immunoglobulin has the amino acid sequence inherent in each isotype such as IgG (IgG1, IgG2, IgG3, IgG4), IgM, IgA, IgD, and IgE. The constant region of a humanized monoclonal antibody in the present invention can be that from human immunoglobulin belonging to any isotype. Preferably, it is the constant region of human IgG. The framework regions of the constant region derived from human immunoglobulin are not particularly limited.

The humanized monoclonal antibody of the present invention can be produced, for example, as follows. Needless to say, the production method is not limited thereto.

For example, a recombinant humanized monoclonal antibody derived from mouse monoclonal antibody can be prepared by genetic engineering, referring to unexamined Japanese patent publication (JP-WA) No. Hei 4-506458 and unexamined Japanese patent publication (JP-A) No. Sho 62-296890. Namely, at least one mouse H chain CDR gene and at least one mouse L chain CDR gene corresponding to the mouse H chain CDR gene are isolated from hybridomas producing mouse monoclonal antibody, and human H chain gene encoding the whole regions except human H chain CDR corresponding to mouse H chain CDR mentioned above and human L chain gene encoding the whole region except human L chain CDR correspond to mouse L chain CDR mentioned above are isolated from human immunoglobulin genes.

The mouse H chain CDR gene(s) and the human H chain gene(s) so isolated are operably inserted into an appropriate vector so that they can be expressed. Similarly, the mouse L chain CDR gene(s) and the human L chain gene(s) are operably inserted into another appropriate vector so that they can be expressed. Alternatively, the mouse H chain CDR gene(s)/human H chain gene(s) and mouse L chain CDR gene(s)/human L chain gene(s) can be operably inserted into the same expression vector so that they can be expressed. Host cells are transformed with the expression vector thus prepared to obtain transformants producing humanized monoclonal antibody. By cultivating the transformants, desired humanized monoclonal antibody is obtained from culture supernatant.

The "human monoclonal antibody" of the present invention is immunoglobulin in which the entire regions comprising the variable and constant region of H chain, and the variable and constant region of L chain constituting immunoglobulin are derived from the gene encoding human immunoglobulin.

The human antibody can be produced in the same way as the production method of polyclonal or monoclonal antibodies mentioned above by immunizing, with an antigen, a transgenic animal which for example, at least human immunoglobulin gene(s) have been integrated into the locus of a non-human mammal such as a mouse by the usual method.

For example, a transgenic mouse producing human antibodies is prepared by the methods described in Nature Genetics 7:13-21, 1994; Nature Genetics 15:146-156, 1997; JP-WA Nos. Hei 4-504365 and Hei 7-509137; Nikkei Science 6:40-50, 1995; International patent publication No. WO94/25585; Nature 368:856-859, 1994; and JP-WA No. Hei 6-500233.

In addition, recently developed technique for producing a human-derived protein from the milk of a transgenic cow or pig can also be applied (Nikkei Science, pp. 78-84, April, 1997).

The "portion of an antibody" used in the present invention means a partial region of the monoclonal antibody as mentioned above, and specifically, means $F(ab')_2$, Fab', Fab, Fv (variable fragment of antibody), sFv, dsFv (disulfide stabilized Fv), or dAb (single domain antibody) (Exp. Opin. Ther. Patents 6:441-456, 1996).

"$F(ab')_2$" and "Fab'" can be produced by treating immunoglobulin (monoclonal antibody) with a protease such as pepsin and papain, and means an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH(H chain variable region) and CHγ1 (γ1 region in the constant region of H chain) are connected at their C terminal regions through a disulfide bond. Each of such two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called $F(ab')_2$.

The "pharmaceutical composition" of the present invention comprises any one of the "polypeptides" of the present invention as defined above; "homodimer molecule", "polypeptide fragment", "fusion polypeptide" comprising the polypeptide; "homodimer molecule" comprising the fusion polypeptides, "antibody", or "portion of an antibody"; and a pharmaceutically acceptable carrier.

The "pharmaceutically acceptable carrier" includes a excipient, a diluent, an expander, a decomposition agent, a stabilizer, a preservative, a buffer, an emulsifier, an aromatic, a colorant, a sweetener, a viscosity increasing agent, a flavor, a solubility increasing agent, or other additives. Using one or more of such carriers, a pharmaceutical composition can be formulated into tablets, pills, powders, granules, injections, solutions, capsules, troches, elixirs, suspensions, emulsions, or syrups. The pharmaceutical composition can be administered orally or parenterally. Other forms for parenteral administration include a solution for external application, suppository for rectal administration, and pessary, prescribed by the usual method, which comprises one or more active ingredient.

The dosage can vary depending on the age, sex, weight, and symptom of a patient, effect of treatment, administration route, period of treatment, or the kind of active ingredient (polypeptide or antibody mentioned above) contained in the pharmaceutical composition. Usually, the pharmaceutical composition can be administered to an adult in a dose of 10 µg to 1000 mg (or 10 µg to 500 mg) per one administration. Depending on various conditions, the dosage less than that mentioned above may be sufficient in some cases, and the dosage more than that mentioned-above may be necessary in other cases.

In particular, the injection can be produced by dissolving or suspending the antibody in a non-toxic, pharmaceutically acceptable carrier such as physiological saline or commercially available distilled water for injection with adjusting a concentration to 0.1 µg antibody/ml carrier to 10 mg antibody/ml carrier. The injection thus produced can be administered to a human patient in need of treatment in a dose of 1 µg to 100 mg/kg body weight, preferably 50 µg to 50 mg/kg body weight once or more times a day. Examples of administration route are medically appropriate administration routes such as intravenous injection, subcutaneous injection, intradermal injection, intramuscular injection, or intraperitoneal injection, preferably intravenous injection.

The injection can also be prepared into a non-aqueous diluent (for example, propylene glycol, polyethylene glycol, vegetable oil such as olive oil, and alcohol such as ethanol), suspension, or emulsion.

The injection can be sterilized by filtration with a bacteria-non-penetrated filter, by mixing bactericide, or by irradiation. The injection can be produced in the form that is prepared upon use. Namely, it is freeze-dried to be a sterile solid composition, and can be dissolved in sterile distilled water for injection or another solvent before use.

The pharmaceutical composition of the present invention can be applied to treating or preventing various autoimmune diseases, allergic diseases, or inflammatory diseases caused by the activation of lymphocytes such as T cells and the regulation of activated lymphocyte functions. Examples of the diseases are rheumatoid arthritis, multiple sclerosis, autoimmune thyroiditis, allergic contact dermatitis, chronic inflammatory dermatosis such as lichen planus, systemic lupus erythematosus, insulin dependent diabetes mellitus, and psoriasis.

The therapeutic effect of the pharmaceutical composition of the present invention for symptom of various diseases can be tested by the usual method by administering it to an known disease model animal.

Examples of the model include (1) a (NZB/NZW) F1 mouse, a model for human systemic lupus erythematosus (SLE) (Science 125:1225-1227, 1994); (2) experimental allergic encephalomyelitis (EAE), a model for multiple sclerosis (MS) (J. Clin. Invest. 95:2783-2789, 1995); (3) an NOD (non-obese diabetes) mouse, a model for insulin dependent diabetes mellitus (IDDM) (J. Exp. Med. 181:1145-1155, 1995); (4) rat nephritis model by renal glomerulus basement membrane immunity, Goodpasture's nephritis model (Eur. J.

Immunol. 24:1249-1254, 1994); and (5) a DBA/1 mouse, a model for human rheumatoid arthritis (Eur. J. Immunol. 26:2320-2328, 1996).

Subfigure (a) shows the state of the cells in the absence of any hybridoma supernatant, subfigure (b) shows the state of cell aggregation induced by "JTT-1 antibody," subfigure (c) shows the state of the cell aggregation in the presence of "anti-ICAM-1 antibody" together with "JTT-1 antibody," and subfigure (d) shows the state of the cell aggregation in the presence of "JTT-2 antibody" together with "JTT-1 antibody."

FIG. 2 are micrographs showing the state of aggregation of FTL435 cells and rat activated lymphoblasts induced by "JTT-1 antibody" and the state of inhibition of the cell aggregation by "JTT.2 antibody."

Subfigure (a) shows the state of FTL435 cells in the absence of any antibody, subfigure (b) shows the state of FTL435 cells in the presence of PMA, subfigure (c) shows the state of FTL435 cells in the presence of "JTT-1 antibody," subfigure (d) shows the state of FTL435 cells in the presence of anti-LFA-1 antibody together with "JTT-1 antibody," subfigure (e) shows the state of FTL435 cells in the presence of anti-CD18 antibody together with "JTT-1 antibody," subfigure (f) shows the state of FTL435 cells in the presence of anti-ICAM-1 antibody together with "JTT-1 antibody," subfigure (g) shows the state of activated lymphoblasts in the absence of any antibody, subfigure (h) shows the state of activated lymphoblasts in the presence of PMA, subfigure (i) shows the state of activated lymphoblasts in the presence of "JTT-1 antibody," subfigure (j) shows the state of activated lymphoblasts in the presence of anti-LFA-1 antibody together with "JTT-1 antibody," subfigure (k) shows the state of activated lymphoblasts in the presence of anti-CD18 antibody together with "JTT-1 antibody," and subfigure (l) shows the state of activated lymphoblasts in the presence of anti-ICAM-1 antibody together with "JTT-1 antibody."

Figure 3:
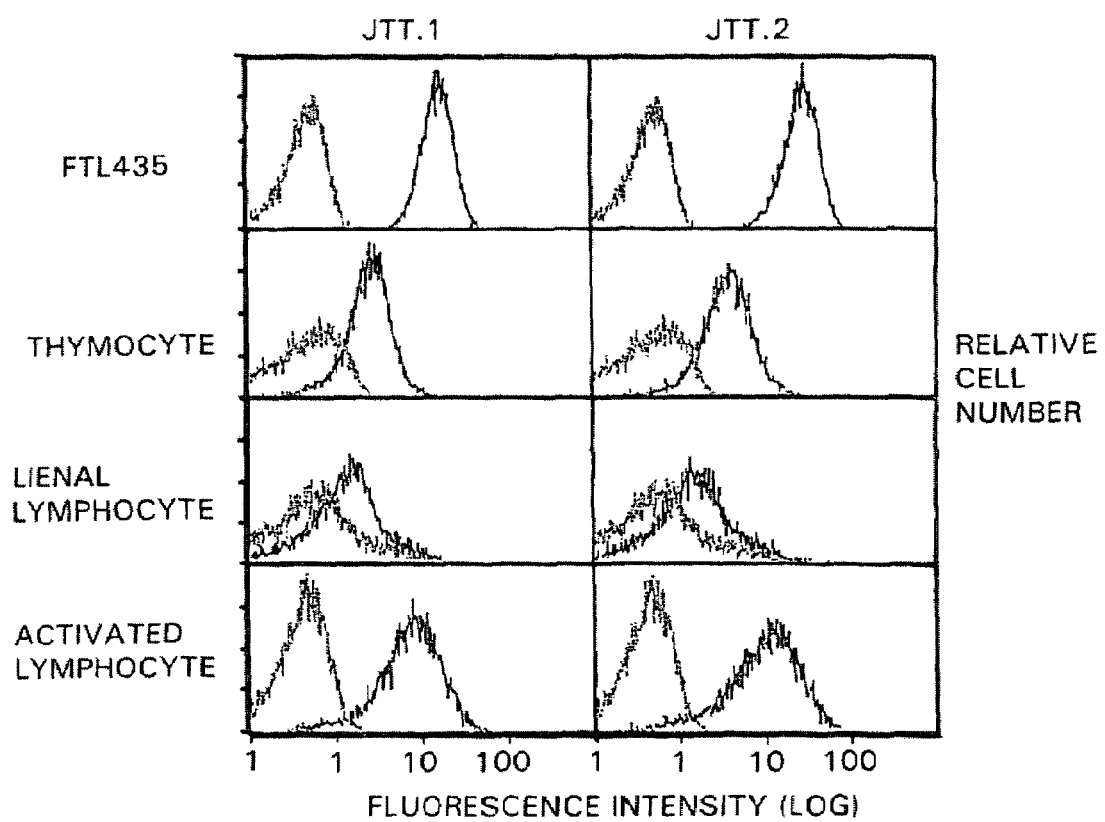

FIG. 3 shows the expression state of "JTT-1 antigen" and "JTT-2 antigen" in various cells measured with a flow-cytometer.

Figure 4:
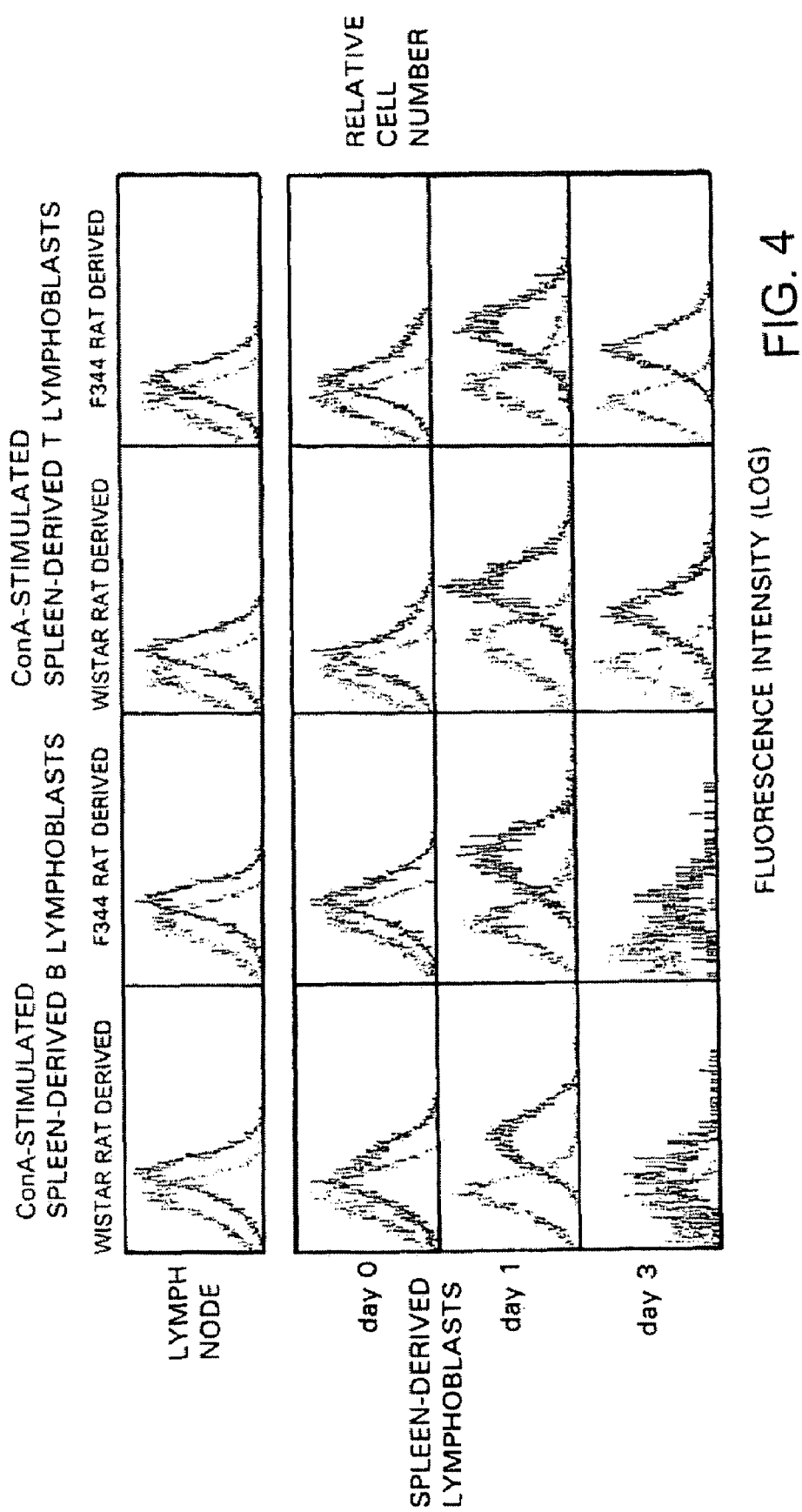

FIG. 4 shows the expression state of "JTT-1 antigen" in various lymphocytic cells measured with a flow-cytometer.

Figure 5:
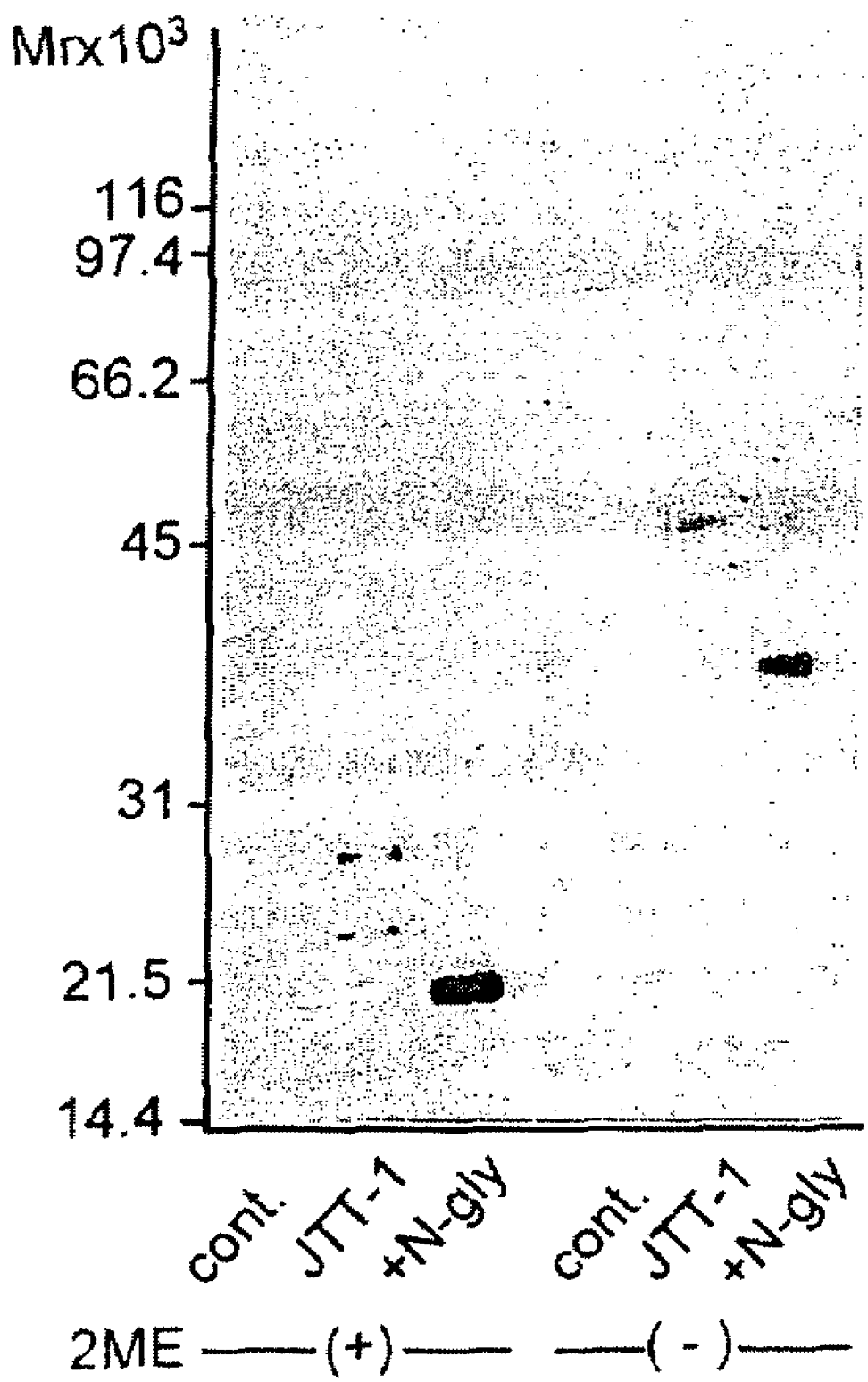

FIG. 5 is a photograph showing electrophoretogram of "JTT-1 antigen" analyzed by SDS-PAGE.

FIG. 6 are micrographs showing the state of adhesion of rat thymocytes to the microtiter plate coated with purified "JTT-1 antigen," where the adhesion is induced in the presence of "JTT-1 antibody," and the state of inhibition of the cell adhesion by "JTT-2 antibody."

Subfigure (a) shows the state of adhesion of the cells to the plate which has not been coated with "JTT-1 antigen," subfigure (b) shows the state of adhesion of the cells to the plate coated with "JTT-1 antigen" in the absence of any antibody, subfigure (c) shows the state of adhesion of the cells to the plate coated with "JTT-1 antigen" in the presence of the Fab fragments of "JTT-1 antibody," and subfigure (d) shows the state of adhesion of the cells to the plate coated with "JTT-1 antigen" in the presence of "JTT-2 antibody" together with the Fab fragments of "JTT-1 antibody."

Figure 7:
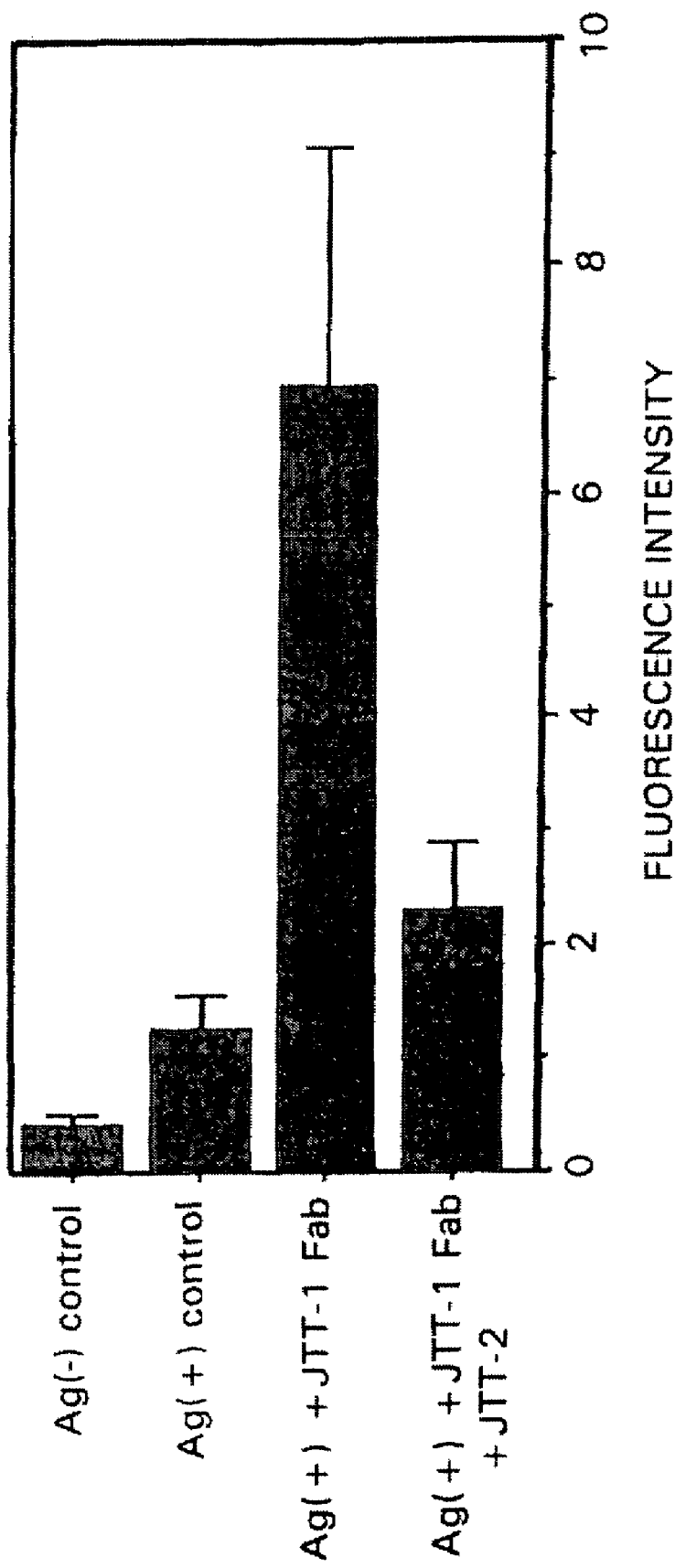

FIG. 7 shows the relative cell number of thymocytes adhering to the plate coated with purified "JTT-1 antigen" measured in terms of fluorescence intensity.

"Ag(−)" shows the relative cell number in the plate which has not been coated with "JTT-1 antigen," "Ag(+)" shows the relative cell number in the plate coated with "JTT-1 antigen" in the absence of any antibody, "Ag(+)+JTT-1 Fab" shows the relative cell number in the plate coated with "JTT-1 antigen" in the presence of the Fab fragments of "JTT-1 antibody", and "Ag(+)+JTT-1 Fab+JTT-2" shows the relative cell number in the plate coated with "JTT-1 antigen" in the presence of "JTT-2 antibody" together with the Fab fragments of "JTT-1 antibody."

Figure 8:
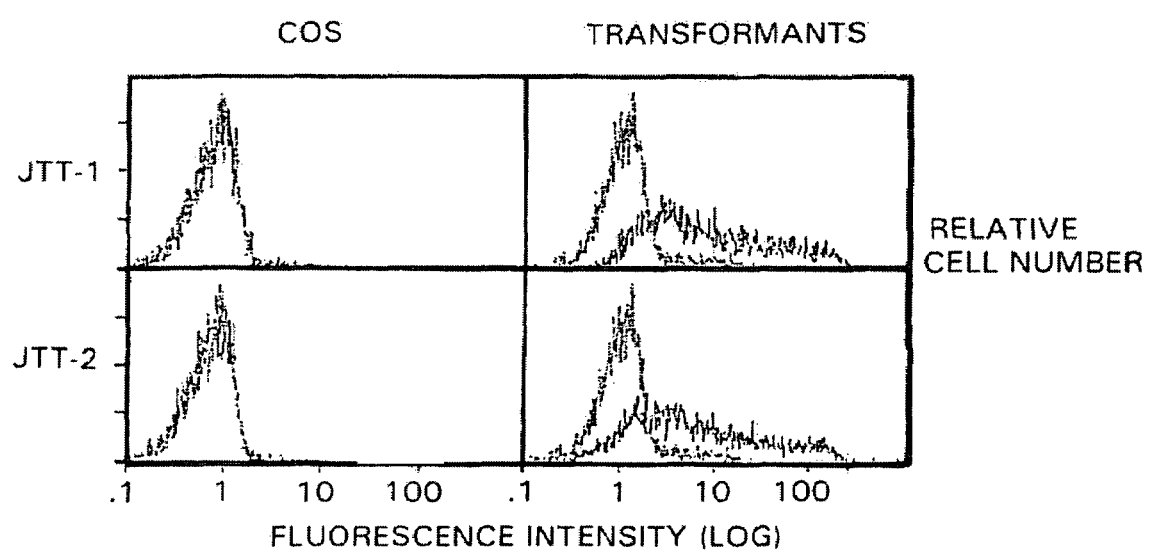

FIG. 8 shows the expression state of "rat JTT-1 antigen" and "rat JTT-2 antigen" in COS cells transformed with cDNA encoding "rat JTT-1 antigen" with a flow-cytometer.

Figure 9:
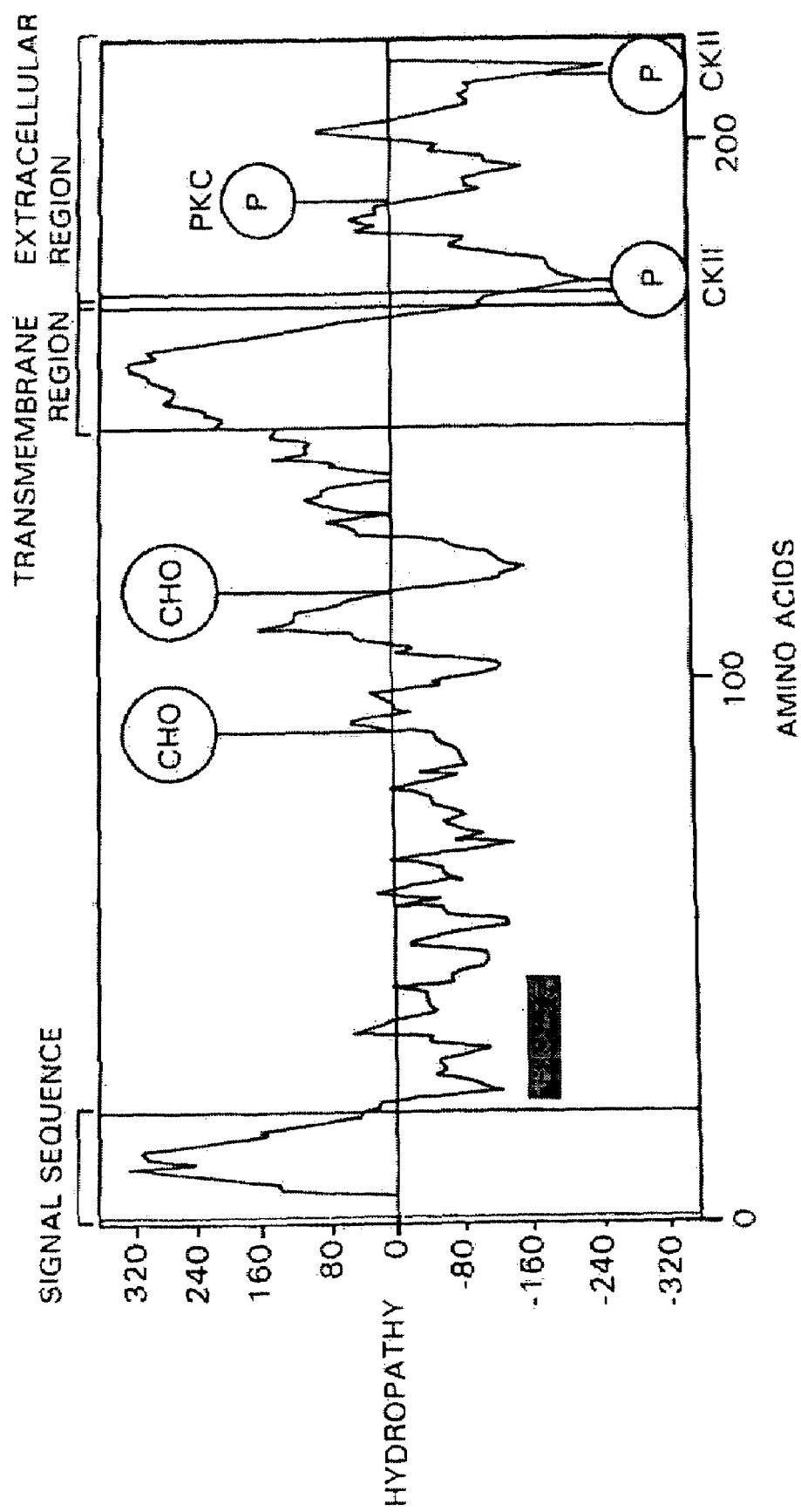

FIG. 9 shows the structural characteristics of amino acid sequence of "JTT-1 antigen" revealed by hydropathy plot analysis.

Figure 10:
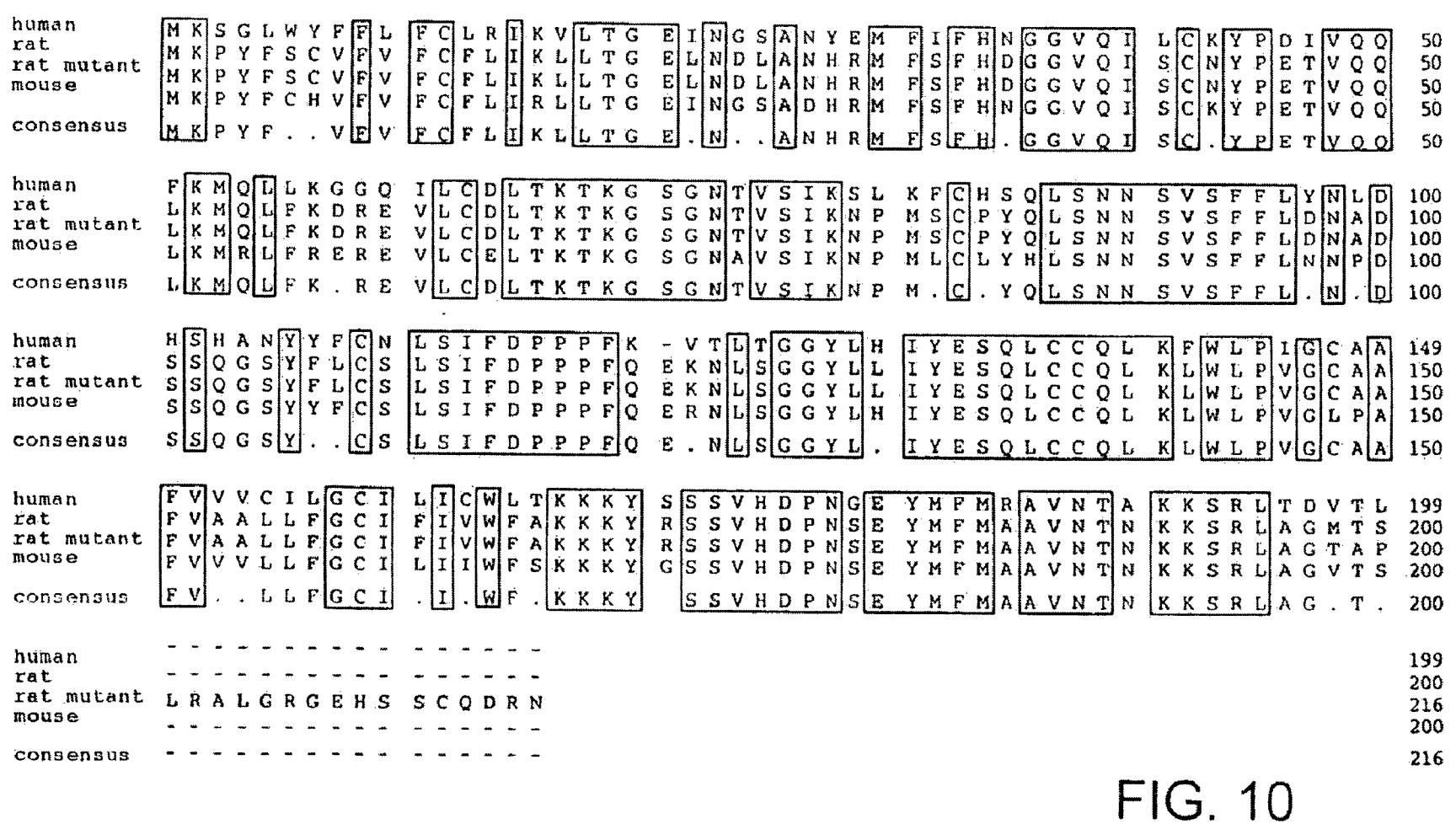

FIG. 10 shows the homology among amino acid sequences of human, rat, and mouse "JTT-1 antigen" and "rat JTT-1 antigen" mutant.

Figure 11:
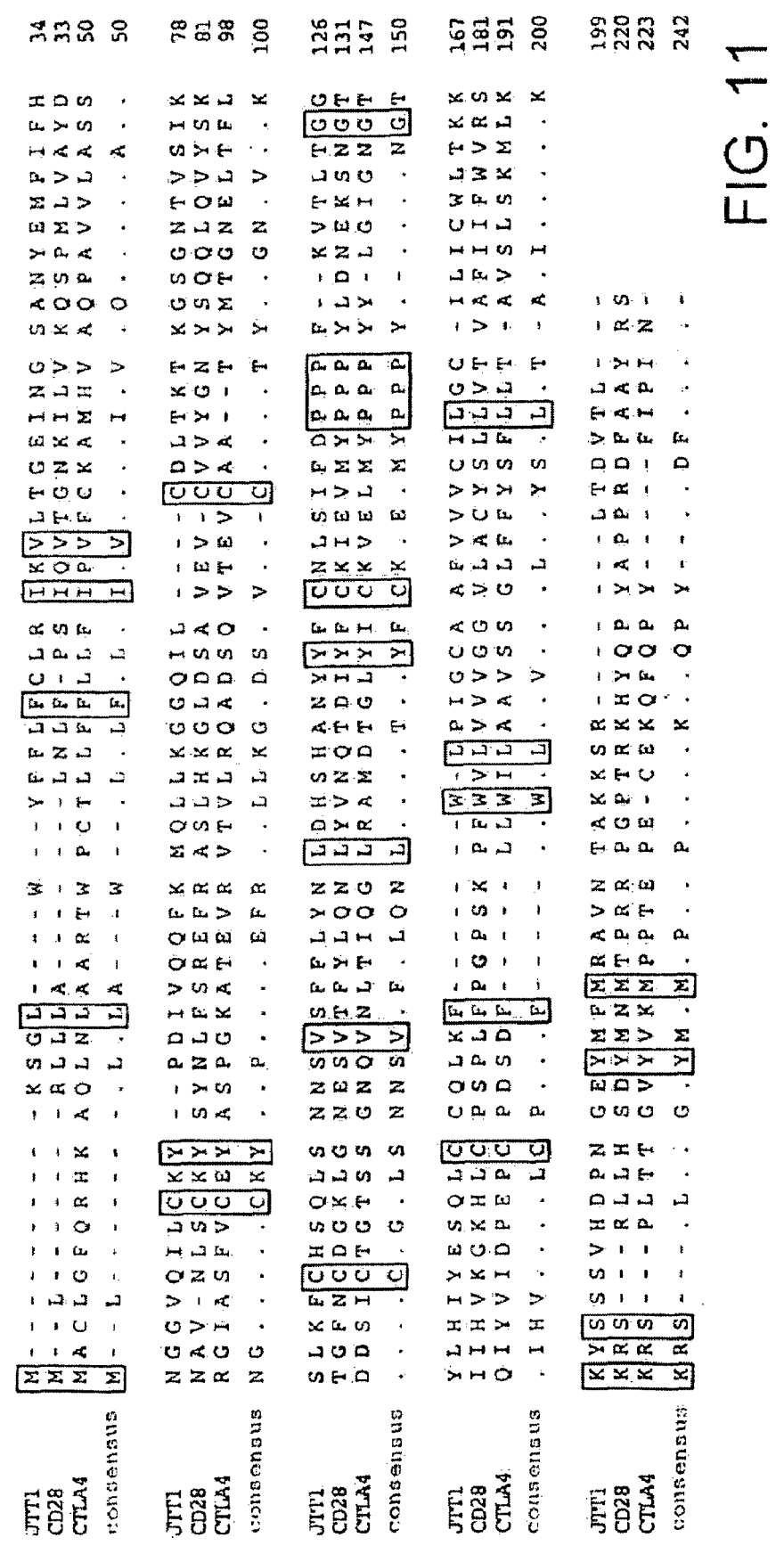

FIG. 11 shows the homology among amino acid sequences and conservation state of motifs in "human JTT-1 antigen," "human CD28 molecule", and "human CTLA-4 molecule."

Figure 12:
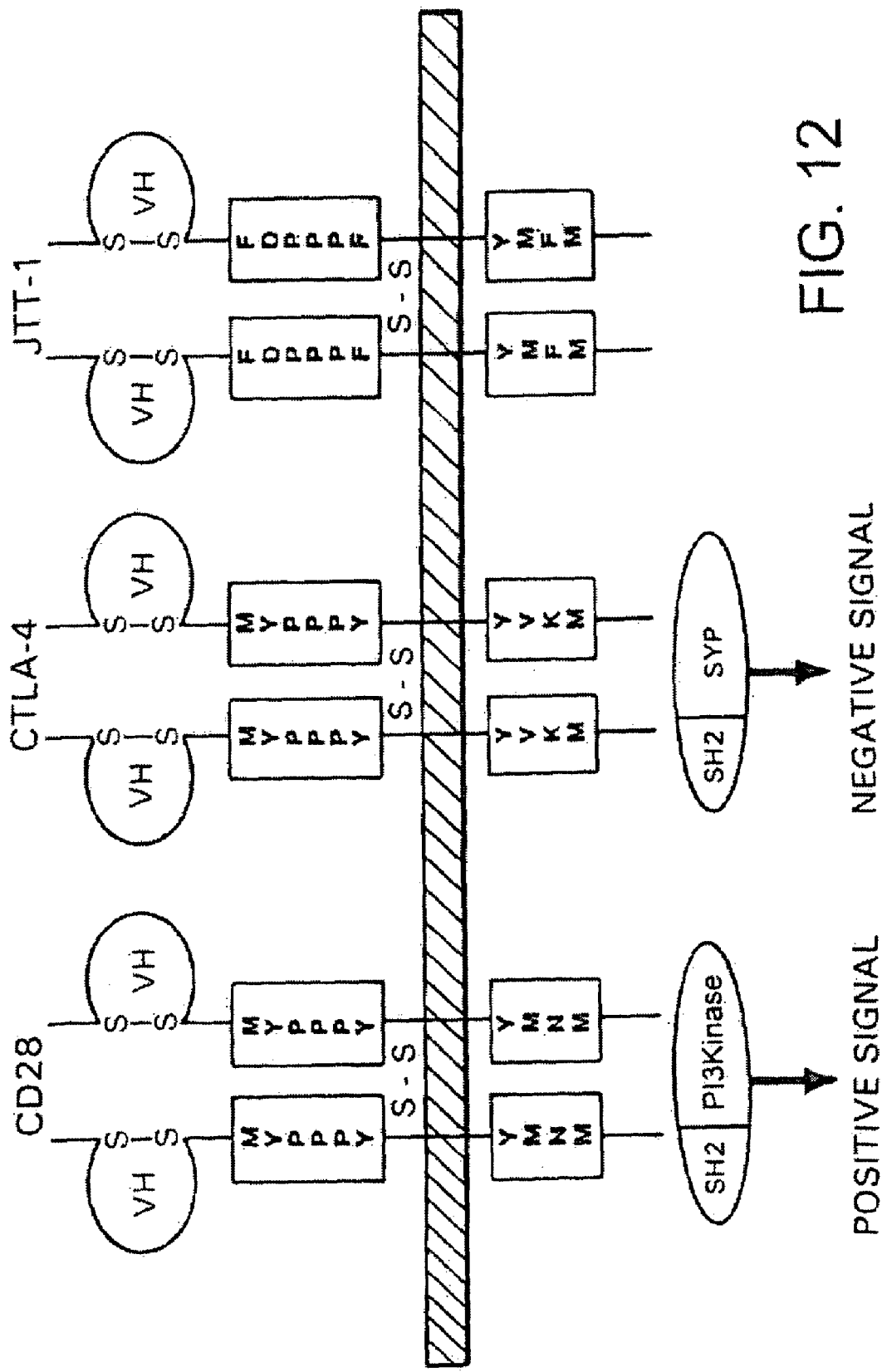

FIG. 12 schematically shows the protein secondary structure of, and their similarity among "human JTT-1 antigen," "human CD28 molecule," and "human CTLA-4 molecule."

Figure 13:
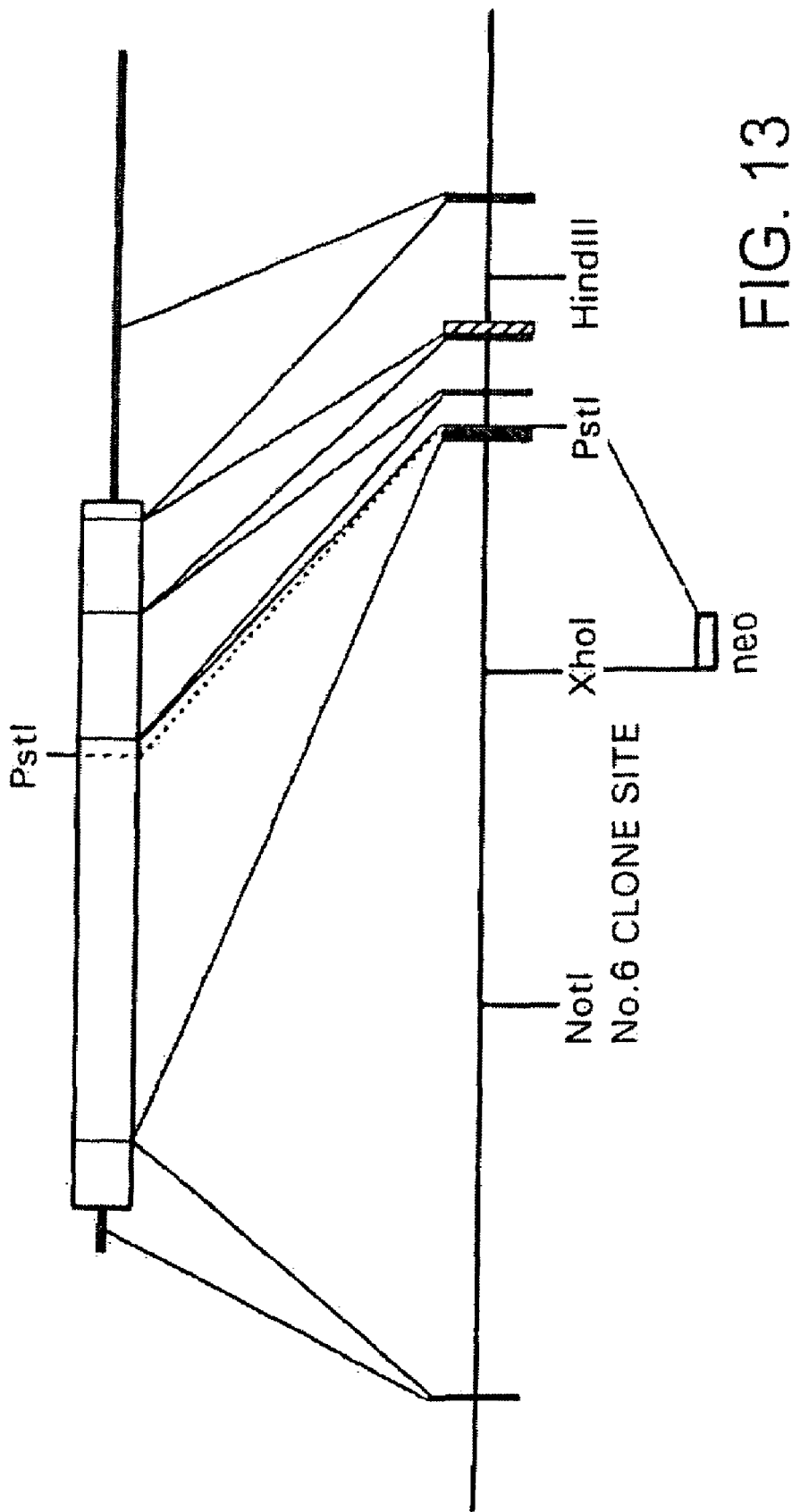

FIG. 13 schematically shows the structure of the genomic DNA encoding "mouse JTT-1 antigen."

FIG. 14 shows the difference in amino acid sequences between "rat JTT-1 antigen" and its alternative splicing mutant.

Figure 15:
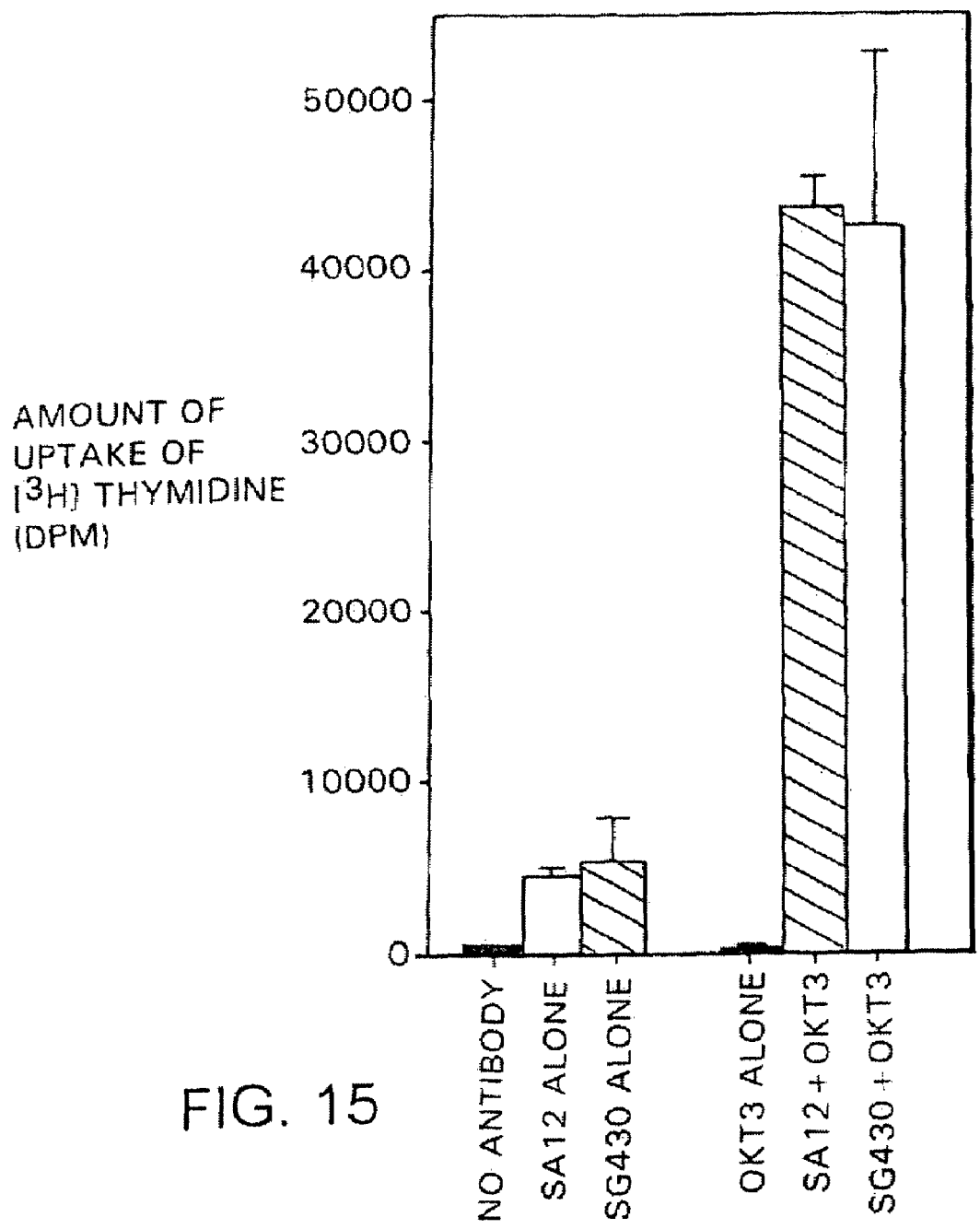

FIG. 15 shows the degree of the growth of human peripheral blood lymphocytes induced by the monoclonal antibody against "human JTT-1 antigen," where the degree of the growth was measured by [$^3$H] thymidine uptake.

The ordinate shows the amount of uptake (dpm) of [$^3$H] thymidine into the cells.

Figure 16:
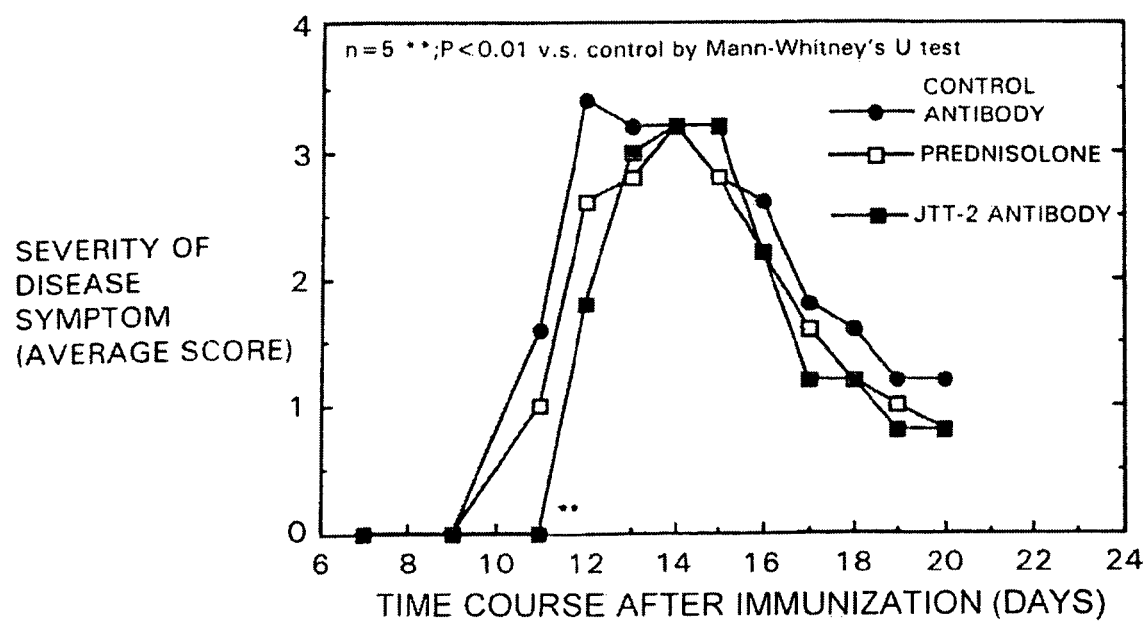

FIG. 16 shows the therapeutic effect of the monoclonal antibody against "JTT-1 antigen" on experimental allergic encephalomyelitis (EAE) in a disease model rat.

The ordinate shows the scored degree of disease symptom, and the abscissa shows the days after immunization for induction of EAE.

Figure 17:
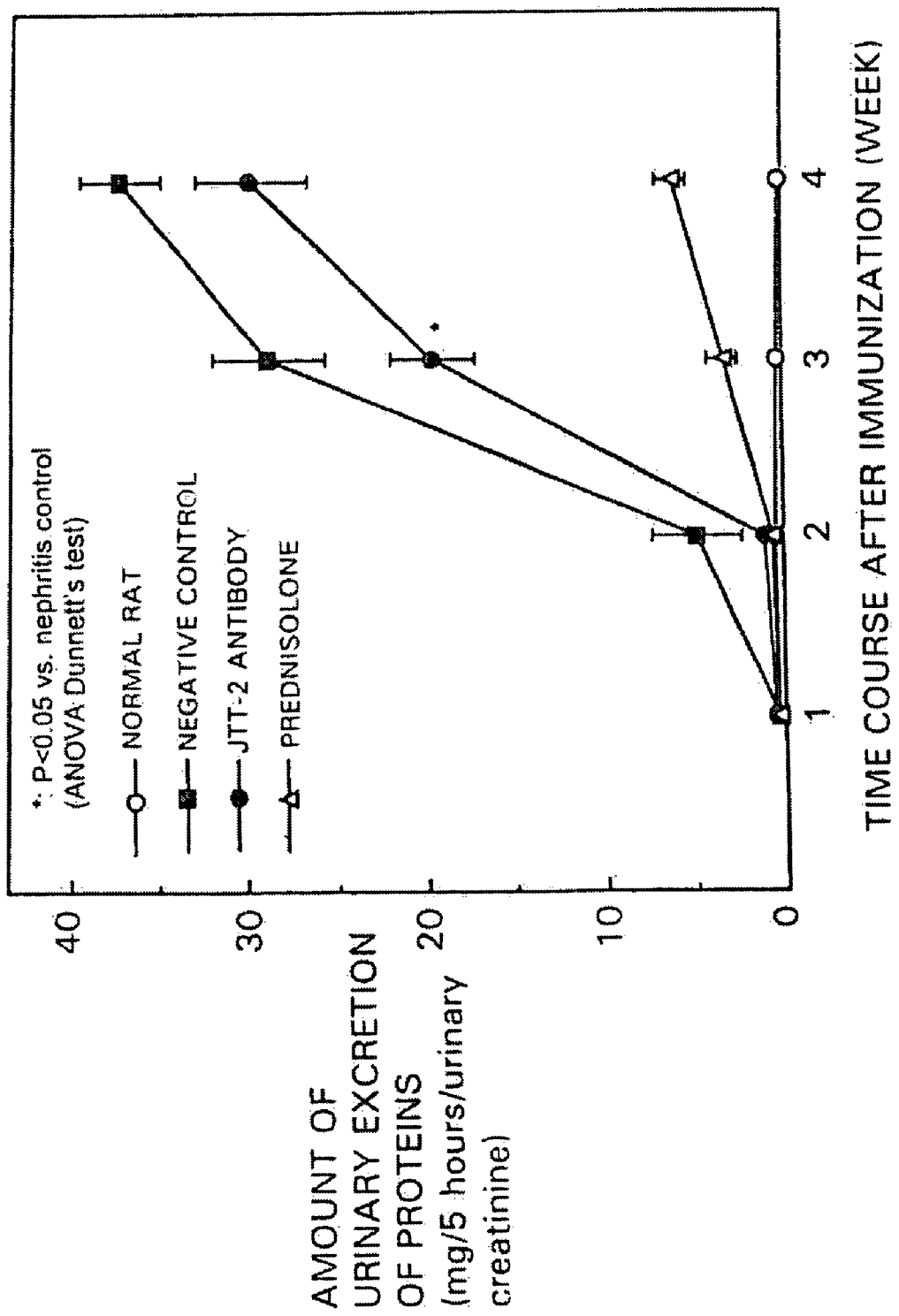

FIG. 17 shows the therapeutic effect of the monoclonal antibody against "JTT-1 antigen" on glomerulonephritis in a disease model rat.

Figure 18:
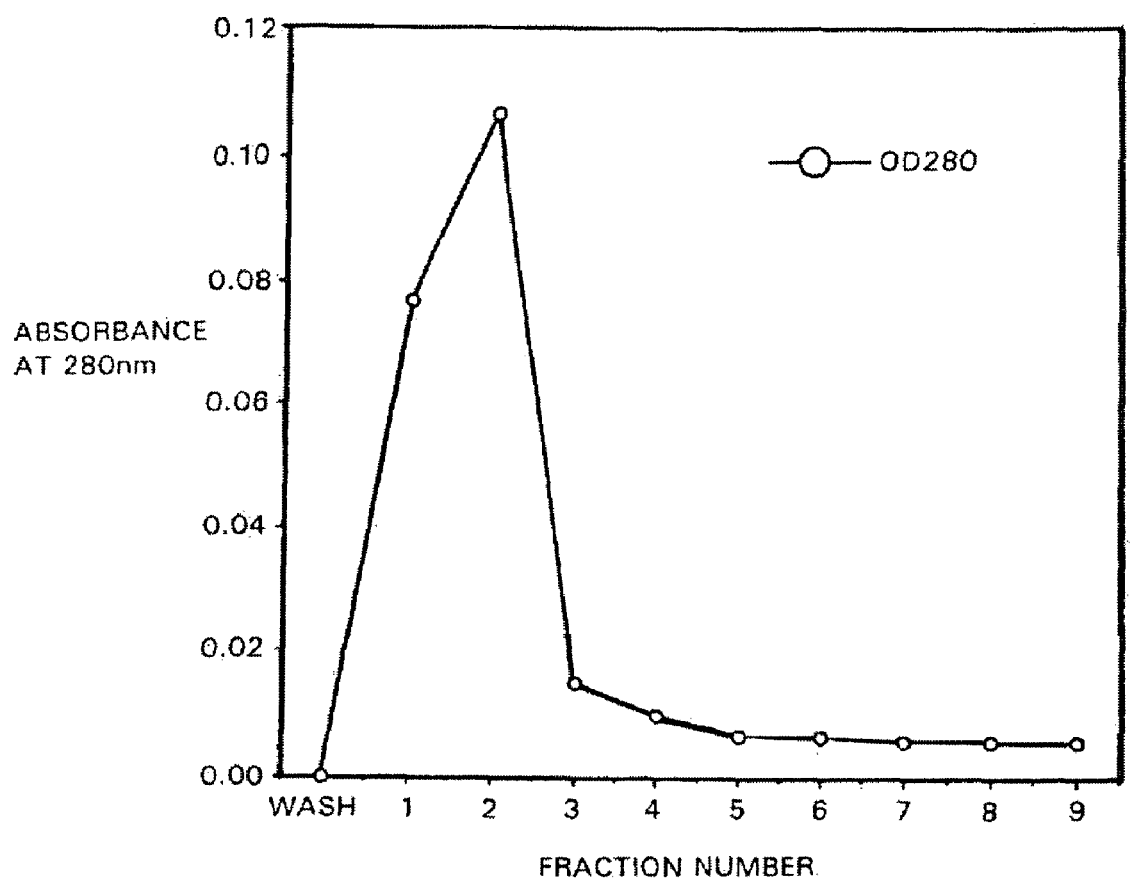

The ordinate shows the amount of urinary excretion of proteins, and the abscissa shows the time course (week) after immunization for induction of glomerulonephritis FIG. 18 shows a column histogram in purification of fusion polypeptide between "rat JTT-1 antigen" extracellular region and human IgFc (rJTT-1-IgFc) with protein A Sepharose column.

Figure 19:
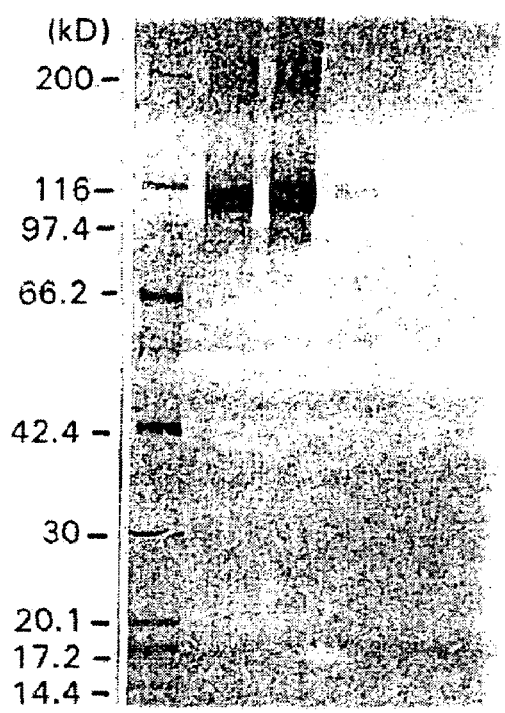

FIG. 19 is a photograph showing electrophoretogram of rJTT-1-IgFc analyzed by SDS-PAGE.

Figure 20:
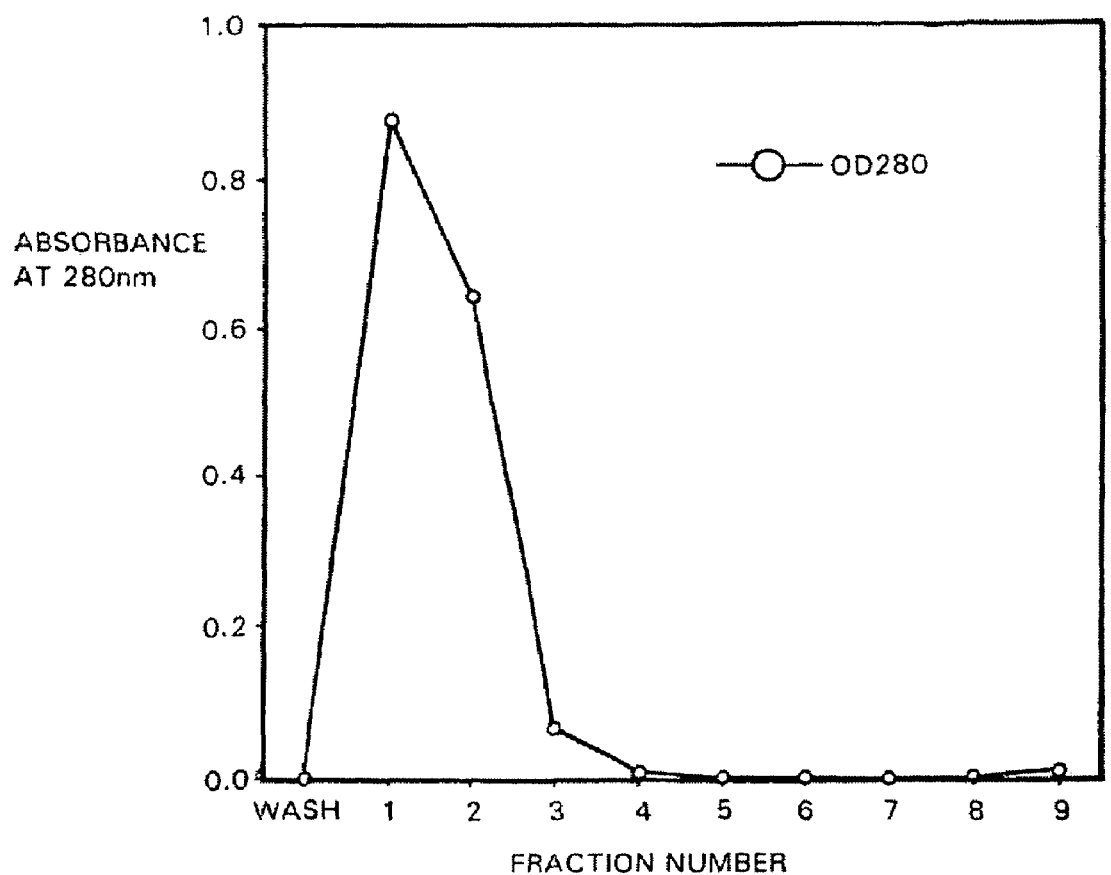

FIG. 20 shows a column histogram in purification of fusion polypeptide between "human JTT-1 antigen" extracellular region and human IgFc (hJTT-1-IgFc) with protein A Sepharose column.

Figure 21:
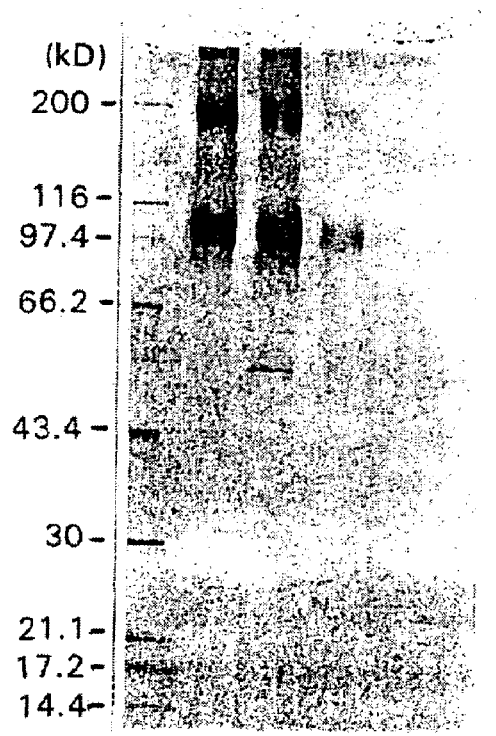

FIG. 21 is a photograph showing electrophoretogram of hJTT-1-IgFc analyzed by SDS-PAGE.

Figure 22:
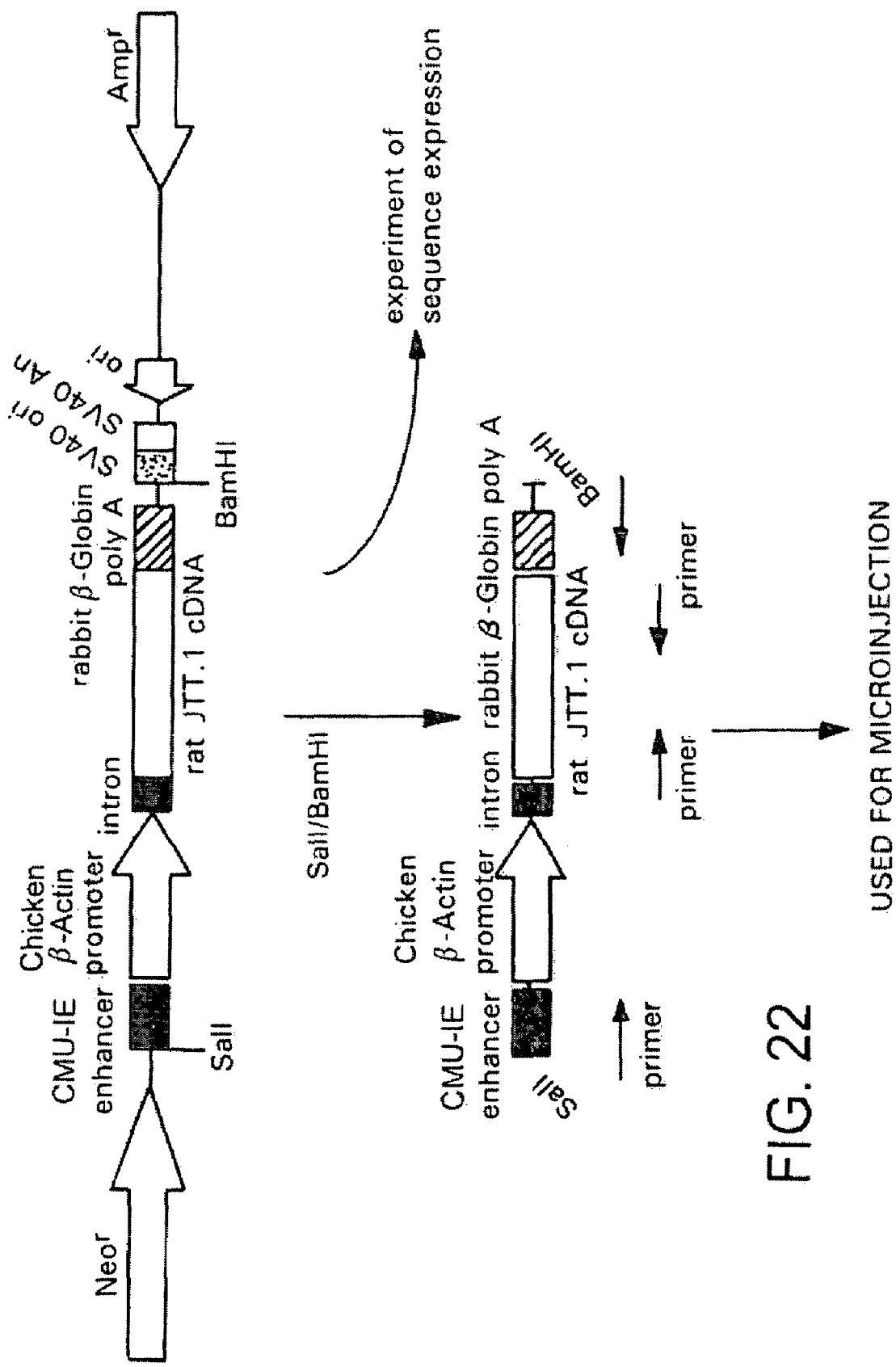

FIG. 22 schematically shows the structure of the gene transfer (targeting) vector used for preparation of a transgenic mouse into which the cDNA encoding "rat JTT-1 antigen" has been introduced.

BEST MODE FOR IMPLEMENTING THE INVENTION

The present inventions are described in more detail with reference to Examples below, but are not to be construed to be limited thereto.

EXAMPLE 1

Preparation of Monoclonal Antibodies

Antibody-producing hybridomas were prepared according to the method of Köhler et al. (Omori et al., Blood, 81:101-111, 1993), and monoclonal antibodies were prepared according to the method of Kannagi et al. (Handbook of Experimental Immunology, 4:117.21-117.21, 1986).

First, rat thymoma cell line FTL435 cells were administered as an immunizing antigen to BALB/c mice into their footpad in an amount of $10^7$ cells/mouse at intervals of 0, 7, 14, and 28 days. The mixture of the antigen with Freund's complete adjuvant was administered only in the first immunization. Two days after the last immunization, the lymph nodes of the mice were taken out and fused with mouse myeloma cells PAI (JCR No. B0113; Stocker et al., Res. Disclosure, 217:155, 1982) by the usual method to obtain many hybridomas producing monoclonal antibodies.

EXAMPLE 2

Screening of Hybridomas and Characterization of Monoclonal Antibodies

The hybridomas prepared in Example 1 were screened by analyzing the effect of the antibodies produced in the culture supernatant of the hybridomas on FTL435 cells, which were used as the immunogen. FTL435 cells ($5 \times 10^6$ cells/ml, 0.1 ml) were seeded into each well of a 96-well microtiter plate and cultivated at 37° C. for an hour in the presence of culture supernatant of each hybridoma (10 μg/ml each). The results obtained for hybridoma clones "JTT-1" and "JTT-2" are shown in FIG. 1 and FIG. 2.

Figure 1A:
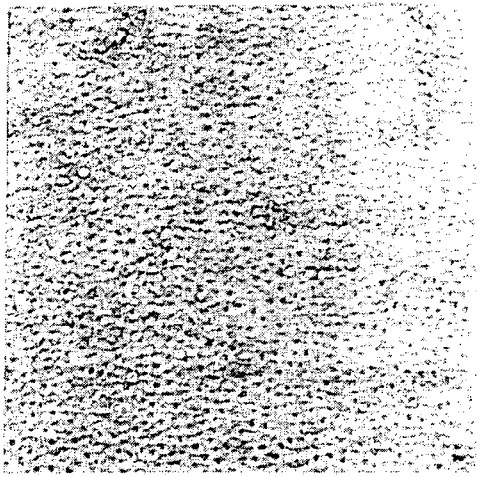
FIG. 1 are micrographs showing the state of aggregation of FTL435 cells induced by "JTT-1 antibody" and the state of inhibition of the cell aggregation by "JTT.2 antibody."
Figure 1B:
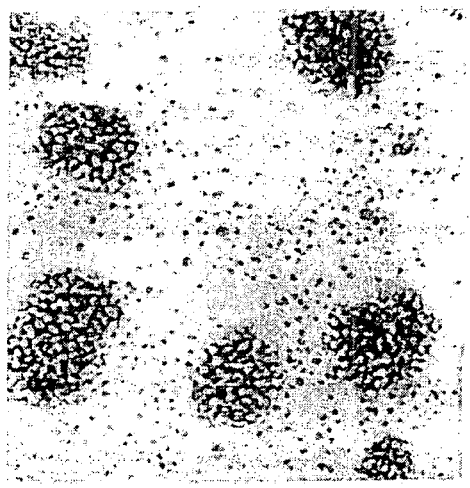
Figure 1C:
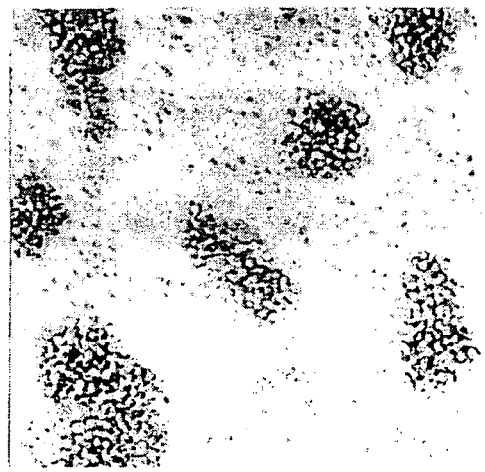
Figure 1D:
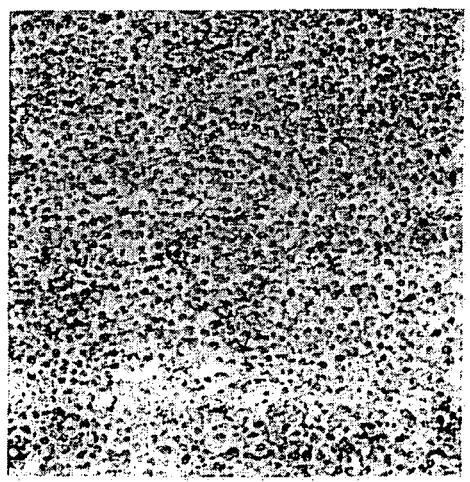

It was revealed that a monoclonal antibody produced by hybridoma clone "JTT-1" ("JTT-1 antibody") strongly agglutinated FTL435 cells (FIG. 1(b) and FIG. 2(c)) and that addition of "JTT-2 antibody" strongly inhibited the aggregation of FTL435 cells induced by "JTT-1 antibody" stimulation (FIG. 1(d)). The assays, in which no hybridoma supernatant was added, were used as controls (FIG. 1(a) and FIG. 2(a)).

In order to determine whether the aggregation of FTL435 cells induced by "JTT-1 antibody" stimulation was caused by the cell adhesion between intercellular adhesion molecule-1 (ICAM-1) and lymphocyte function-associated antigen-1 (LFA-1), which is a representative known pathway of cell adhesion, FTL435 cells were cultivated at 37° C. for an hour in the presence of anti-rat ICAM-1 antibody 1A29 (10 μg/ml; IgG1) or anti-rat LFA-1 antibody (10 μg/ml; IgG2a) together with "JTT-1 antibody."

The aggregation of FTL435 cells by "JTT-1 antibody" stimulation was inhibited by neither anti-ICAM-1 antibody nor anti-LFA-1 antibody (anti-ICAM-1 antibody, FIG. 1(c) and FIG. 2(f); anti-LFA-1 antibody, FIG. 2(d)).

In order to further analyze the cell agglutination ability of "JTT-1 antibody," the ability to agglutinate rat lymphoblast cells activated with concanavalin A stimulation was analyzed in the same manner as mentioned above. The results are shown in FIG. 2.

Similar to the effect on FTL435 cells, the aggregation of activated lymphoblast cells was induced by "JTT-1 antibody" stimulation (FIG. 2(i)). The aggregation of activated lymphoblast cells by "JTT-1 antibody" stimulation was mostly inhibited by anti-LFA-1 antibody (FIG. 2(j)) and anti-ICAM-1 antibody (FIG. 2(l)). (However, Partial Aggregation Occurred.)

As understood from the control assay (FIG. 2(g)), in which no antibody was added, activated lymphocytes such as activated lymphoblasts showed no aggregation through cell adhesion unless they receive the stimulation with phorbol myristate acetate (PMA, which activates LFA-1) (FIG. 2(h)) or "JTT-1 antibody" (FIG. 2(i)). Therefore, the fact that anti-LFA-1 antibody partially inhibited cell aggregation by "JTT-1 antibody" stimulation indicates that LFA-1 in activated lymphoblast cells was activated by "JTT-1 antibody" stimulation. This also indicates that molecules recognized by "JTT-1 antibody" are involved in some signal transmission.

Hybridoma clones "JTT-1" and "JTT-2" have been deposited under the Budapest Treaty with international depository authority, National Institute of Bioscience and Human-Technology, Agency of Industrial Science and Technology, Ministry of International Trade and Industry, Japan (1-1-3, Higashi, Tsukuba-shi, Ibaraki, Japan) since Oct. 11, 1996 with an international accession Nos. FERM BP-5707 and FERM BP-5708, respectively.

Analysis using mouse monoclonal antibody isotype identification kit (Amersham) determined that the isotype of monoclonal antibodies produced from each hybridoma (JTT-1 antibody and JTT-2 antibody) were both IgG1.

EXAMPLE 3

Reactivity of "JTT-1 Antibody" and "JTT-2 Antibody" to Various Cells

In order to analyze the expression pattern of molecules recognized by "JTT-1 antibody" and "JTT-2 antibody" in various cells, the reactivities of the antibodies to various cells were examined. Molecules recognized by "JTT-1 antibody" or "JTT-2 antibody" are designated "JTT-1 antigen" or "JTT-2 antigen", respectively.

A five- to ten-week-old Wistar rat (150 to 250 g) was killed by anesthesia with diethyl ether. The thymus and spleen were taken out of its chest and abdomen, respectively, by celiotomy, and homogenized to prepare cell suspension. The resulting spleen cells were cultivated in RPMI1640 medium containing 2 μg/ml concanavalin A and 10% FCS at 37° C. for 3 days to prepare activated lymphoblasts.

FTL435 cells, thymocytes, spleen cells, and activated lymphoblasts ($5 \times 10^5$ cells each) were reacted with "JTT-1 antibody" or "JTT-2 antibody" and then with FITC-labeled anti-mouse IgG (Cappel). The fluorescence intensity of the stained cells was measured with EPICS-Elite flow cytometer.

The results are shown in FIG. 3. In FTL435 cells, the strong expression of each "JTT-1 antigen" and "JTT-2 antigen" was observed. While the antigens were expressed in thymocytes, they were expressed only a little in spleen cells. However, in activated lymphoblasts obtained by simulating spleen cells with concanavalin A, "JTT-1 antigen" and "JTT-2 antigen" were strongly expressed. In addition, in each kind of cells, the expression pattern of "JTT-1 antigen" and "JTT-2 antigen" coincided with each other. These results indicate that "JTT-1 antigen" and "JTT-2 antigen" are the same molecules.

EXAMPLE 4

Reactivity of "JTT-1 Antibody" to Various Lymphocytic Cells

In order to analyze the expression pattern of molecules ("JTT-1 antigen") recognized by "JTT-1 antibody" in various lymphocytic cells, the reactivity of "JTT-1 antibody" to lymph nodes, T lymphoblasts derived from spleen, and B lymphoblasts derived from spleen of two kinds of rats (Wistar rat and F344 rat) was analyzed.

A five- to ten-week-old Wistar rat and F344 rat (150 to 250 g) were killed by anesthesia with diethyl ether. The lymph nodes and spleen were taken out of each rat by celiotomy, and homogenized to prepare cell suspension. The resulting cell suspension from spleen was cultivated in RPMI1640 medium containing 2 μg/ml concanavalin A (ConA) and 10% FCS at 37° C. for 3 days. Activated T lymphoblasts and activated B lymphoblasts were obtained from each rat after 1-day and 3-day cultivation. In addition, spleen-derived T lymphoblasts and B lymphoblasts obtained before lymph node cells and ConA were added were used as controls.

Each cells ($5 \times 10^5$ cells each) were reacted with biotin-labeled anti-rat T cell antibody or biotin-labeled anti-rat B cell antibody (10 μg/ml, Seikagaku Corporation), and subsequently with phycoerythrin-labeled streptavidin. The cells were then reacted with 10 μg/ml FITC-labeled "JTT-1 antibody." The fluorescence intensity of the stained cells was measured with EPICS-Elite flow cytometer.

The results are shown in FIG. 4. In both activated T lymphoblasts and activated B lymphoblasts from Wistar rat and F344 rat, the strong expression of "JTT-1 antigen" was observed from day 1 of activation with ConA stimulation. In addition, the expression pattern of "JTT-1 antigen" in each kind of cells almost perfectly coincided with each other.

EXAMPLE 5

Characterization of "JTT-1 Antigen" and "JTT-2 Antigen" by Immunoprecipitation

"JTT1 antigen" and "JTT-2 antigen" were characterized by immunoprecipitation using FTL435 cells.

(1) Preparation of Biotinylated Soluble Cell Surface Molecules

FTL435 cells were washed with PBS, suspended in physiological saline containing 100 μg/ml NHS-biotin and 0.1 M HEPES (pH 8.0) to adjust $1 \times 10^7$ cells/ml, and incubated at room temperature for 40 minutes. The cells were washed three times with PBS, lysis buffer (1% NP-40, 10 mM Tris-HCl (pH 7.4), 0.15 M NaCl) was added thereto to adjust $5 \times 10^7$ cells/ml, and the mixture was allowed to react at 4° C. for 30 minutes to lyse the cells. The cell lysate obtained was centrifuged, and the supernatant comprising biotinylated soluble cell surface molecules was stored at −80° C.

(2) Immunoprecipitation and SDS-PAGE Analysis

The purified sample of "JTT-1 antibody" purified by the usual method from the culture supernatant of the hybridoma clone "JTT-1" prepared in Example 1 was mixed with protein G-Sepharose beads to adjust 2 mg/ml, and allowed to react at 4° C. for an hour to bind the antibody with the beads. After the beads were washed, 500 μl of the biotinylated FTL435 cell lysate was added to 10 μl of the beads, and the mixture was allowed to react at 4° C. for 2 hours. After the beads were washed with lysis buffer three times, 50 μl of glycanase buffer (sodium phosphate buffer (pH 7.0) containing 0.15% SDS) was added to the beads, and the mixture was boiled to elute the bound molecules trapped by the antibody-bound beads. 1.25% NP-40 and 20 U/ml N-glycanase were added to a fraction of the sample so eluted, and the mixture was allowed to react overnight to digest N-linked sugar chains.

An equal volume of sample buffer (Enprotech) for SDS-PAGE was added to 5 μl of the eluted sample in the presence or absence of 2-mercaptoethanol, and the mixture was boiled. After electrophoresis, the gel was transferred to a PVDF membrane. The membrane was blocked with 3% BSA-PBS and reacted with peroxidase-labeled streptavidin to detect biotinylated soluble cell surface molecules trapped by "JTT-1 antibody" with ECL system (Amersham) as described in the manual.

The results are shown in FIG. 5. The "JTT-1 antibody"-recognized molecule ("JTT-1 antigen") on FTL435 cells showed the molecular weight of about 47 kD under the non-reduced conditions ("(−)" in FIG. 5) and about 24 kD and 28 kD under the reduced conditions ("(+)" in FIG. 5). As the result of digestion of N-linked sugar chains ("+N-gly" in FIG. 5), "JTT-1 antigen" was converged on a single band of about 36 kD under the non-reduced conditions and about 20 kD under the reduced conditions. These results suggest that "JTT-1 antigen" forms a dimer in which the same core proteins have different sugar chains. Completely the same results were obtained in the experiment performed as mentioned above using "JTT-2 antibody." Considering these results together with the results of Example 3 and Example 7 below, "JTT-1 antigen" (molecule recognized by "JTT-1 antibody") and "JTT-2 antigen" (molecule recognized by "JTT-2 antibody") have been thought to be identical to each other.

EXAMPLE 6

Adhesion Experiment of Rat Thymocytes to Purified "JTT-1 Antigen" and N Terminal Amino Acid Analysis The following experiments were performed to analyze whether the molecule that "JTT-1 antibody" recognizes ("JTT-1 antigen") functions as an adhesion molecule. N-terminal amino acid analysis was also performed.

(1) Preparation of "JTT-1 antibody"-affinity column The purified sample (2 mg in 2 ml) of "JTT-1 antibody" purified by the usual method from the culture supernatant of the hybridoma clone "JTT-1" prepared in Example 1 was mixed with 1 ml of protein G-Sepharose resin, and the mixture was allowed to react at 4° C. for an hour. The resin was washed three times with 200 mM triethanolamine (pH 8.2). The resin was then incubated in triethanolamine (pH 8.2) containing 10 mM dimethyl pimelimidate (DMP) at room temperature for an hour to covalently bind "JTT-1 antibody" to the resin.

(2) Purification of "JTT-1 Antigen"

FTL435 cells were cultivated in RPMI1640 medium containing 10% FCS. The cells were harvested by centrifugation to obtain a pellet and washed with PBS three times. Lysis buffer (1% NP-40, 10 mM Tris-HCl (pH 7.4), 0.15 M NaCl) was added to the washed pellet to adjust $5 \times 10^7$ cells/ml, and the mixture was allowed to react at 4° C. for 30 minutes to lyse the cells. The cell lysate obtained was centrifuged, and the supernatant containing soluble cell surface molecules was stored at −80° C.

The lysate (400 ml) was loaded onto "JTT-1 antibody"-affinity column. After the column was washed with 50 ml of the lysis buffer and 20 ml of PBS, "JTT-1 antigen" was eluted with 0.2 M glycine buffer (pH 2.8). 1 M Tris buffer was added to the "JTT-1 antigen" so eluted for neutralization. "JTT-1 antigen" obtained was stored at −80° C.

(3) Determination of N Terminal Amino Acid Sequence

After the purified "JTT-1 antigen" was subjected to SDS-PAGE, the N-terminal amino acid sequence was determined by the usual method. The result revealed that "JTT-1 antigen" contained an amino acid sequence Glu-Leu-Asn-Asp-Leu-Ala-Asn-His-Arg.

(4) Adhesion Experiment

A five- to ten-week-old Wistar rat (150 to 250 g) was killed by anesthesia with diethyl ether. The thymus was taken out of its chest by celiotomy and homogenized to prepare thymocyte suspension. 10μ',7'-bis(carboxyethyl)carboxyfluorescein tetraacetoxy-methyl ester (BCECF-AM; Molecular Probes) was added to the suspension, and the mixture was incubated at 37° C. for 30 minutes to fluorescently label the thymocytes. The cells were washed with PBS and suspended in RPMI1640 medium containing 10% FCS to adjust $2 \times 10^7$ cells/ml.

The purified "JTT-1 antigen" obtained in (2) was coated on a 96-well ELISA plate at the concentration of 10 μl/well overnight. After the plate was washed with PBS, 200 μl/well of PBS containing 3% BSA was added to the plate, and blocking was performed for 2 hours. After the plate was washed with PBS, (1) only fluorescence-labeled thymocytes ($2 \times 10^7$ cells/ml, 0.1 ml); (2) fluorescence-labeled thymocytes (same concentration) and "JTT-1 antibody" Fab fragments prepared by the usual method (5μ "JTT-1 antibody" Fab fragments (same concentration), and "JTT-2 antibody" (10μ° C. for an hour. In order to remove unbound cells, each well was washed once with RPMI1640 medium containing 10% FCS. Each well was observed with light microscope. Then, 100 μl of 0.1% NP-40 was added to each well, and the cells adhered to the plate were lysed. The relative cell number of fluorescence-labeled thymocytes adhered to each well was counted by measuring the fluorescence intensity at 538 nm (excited at 485 nm) with Fluoroscan II Microplate Fluorometer (Flow Laboratories). The assay in which a plate was not coated with purified "JTT-1 antigen" was used as a control.

The results of light microscopy observation are shown in FIG. 6.

Figure 6A:
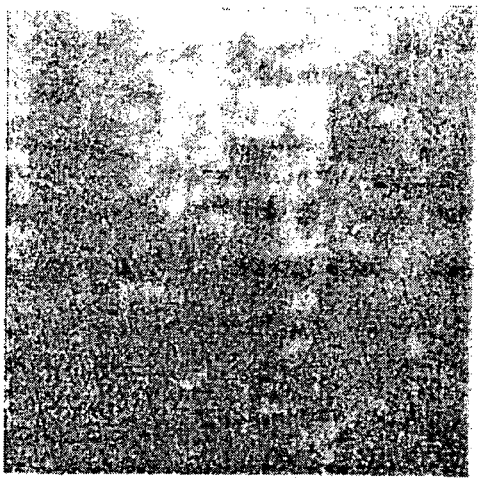
Figure 6B:
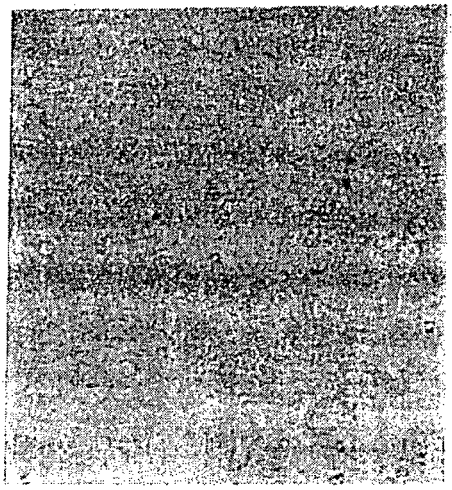
Figure 6C:
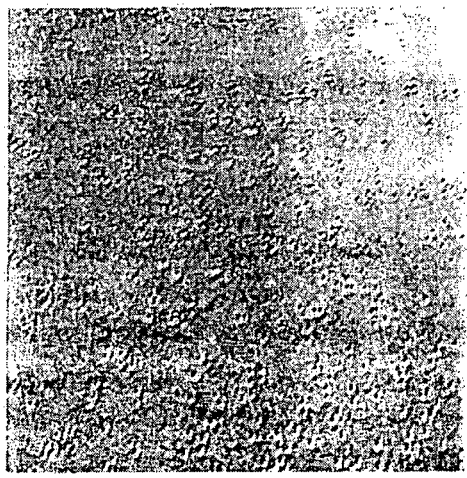
Figure 6D:
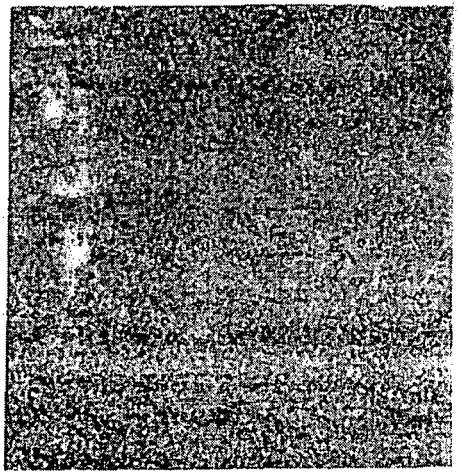

Thymocytes significantly adhered to purified "JTT-1 antigen" only in the presence of "JTT-1 antibody" Fab fragments (FIG. 6(c)). The adhesion was significantly inhibited by "JTT-2 antibody" (FIG. 6(d)).

FIG. 7 shows the relative cell number of thymocytes adhered to "JTT-1 antigen" coated on each well in terms of fluorescent intensity.

From these results, it was revealed that "JTT-1 antigen" functions as an adhesion molecule.

EXAMPLE 7

Cloning of cDNA Encoding Rat "JTT-1 Antigen"

1. Preparation of cDNA Library
1-(1) Extraction of Poly(A)⁺ RNA from ConA-stimulated Rat Lymphoblasts ConA-stimulated lymphoblasts (ConA blast) derived from rat spleen (about $1 \times 10^6$ cells/ml) were centrifuged (2,000×g) at 4° C. for 5 minutes. The precipitated cells were suspended with ISOGEN (Nippon Gene) and extracted with chloroform with shaking to collect the supernatant. After isopropanol was added to the obtained supernatant, the mixture was allowed to stand at room temperature for 10 minutes and centrifuged at 12,000×g at 4° C. for 10 minutes to precipitate RNA. The precipitated RNA was washed with ethanol and dissolved in TE buffer. Poly(A)⁺ RNA was purified from the total RNA so obtained with "mRNA Purification Kit" (Pharmacia).

1-(2) Preparation of cDNA

With 5 μg of the poly(A)⁺ RNA prepared above as a template, cDNA was synthesized with "Time Saver cDNA Synthesis Kit" (Pharmacia). "Oligo dT primer" (Pharmacia) having NotI site was used to increase the efficiency of screening. EcoRI adapter was added, and digestion with NotI was performed to obtain cDNA with unidirectionality. Size fractionation was then performed with Spun Column (Pharmacia).

1-(3) Insertion into a Vector

The obtained cDNA having EcoRI- and NotI-ends was ligated with pME18S (Hara et al., EMBO J., 11:1875-1884, 1992) digested with EcoRI and NotI. "DNA Ligation Kit" (Takara Shuzo) was used for the ligation. *E. coli* DH5 cells (Toyobo) were transformed with the reaction product so obtained. Transformants were cultivated until O.D. value (at 600 nm) reached 0.6 and harvested to recover plasmid DNAs with a library. QUIAGEN-Tip (QUIAGEN) was used for purification of plasmid DNAS.

2. Screening of cDNA Library

Screening was performed according to panning method (Seed et al., Proc. Natl. Acad. Sci. USA, 84:3365-3369, 1987).

2-(1) Gene Transfer into COS Cells

The library so obtained was introduced into COS7 cells by electroporation (Potter et al., Proc. Natl. Acad. Sci. USA, 85:2288-2292). The transformants were cultivated for 60 hours after introduction, the supernatant was removed, and the pellet was washed with PBS three times. After the pellet was treated with PBS (containing 0.5 mM EDTA) at 37° C. for 30 minutes, the cells were removed by pipetting. Only living cells were then collected with "Lymphprep" (NY-COMED).

2-(2) Concentration of Gene-expressing Cells by Panning

The living cells obtained above were suspended in PBS (containing 5% FCS and 0.5 mM EDTA). The cell suspension was transferred to a culture dish coated with "JTT-1 antibody" and incubated at room temperature for 3 hours. After cells not binding to the culture dish were removed and the culture dish was washed with PBS three times, plasmid DNAs were collected from the cells binding to the culture dish by Hirt method (Hirt, J. Mol. Biol., 26:365-369). *E. coli* DH10B (GIBCO BRL) were transformed with the plasmid DNA so obtained. The plasmid DNAs were amplified and purified with the transformants as in (1)-3 mentioned above. The procedures described in (1) and (2) were then repeated twice.

2-(3) Isolation of the Positive Clone

After the third panning, transformed *E. coli* DH10B cells were cultivated overnight on LB plates containing ampicillin to obtain colonies. Twenty drug-resistant colonies were cultivated, plasmid DNAs were collected by alkaline miniprep method (Maniatis et al., Molecular Cloning, A Laboratory Manual, Cold Spring Harbor Laboratory, Cold Spring Harbor, N.Y.), and the insert DNA was analyzed. Agarose gel electrophoresis revealed that the clone having about 0.9 kb cDNA (designated "T132A7") was concentrated.

"T132A7" was transiently expressed in COS7 cells again with the method described in (1). After "T132A7"-introduced cells were reacted with "JTT-1 antibody" or "JTT-2 antibody", and then with FITC-labeled anti-mouse IgG (Cappel), the fluorescence intensity of the stained cells was measured with EPICS-Elite flow cytometer (Coulter). "JTT-1 antibody" and "JTT-2 antibody" strongly recognized the "T132A7" gene product. The results are shown in FIG. 8.

3. Determination of the Nucleotide Sequence and the Amino Acid Sequence

The nucleotide sequence of clone "T132A7" was determined by dideoxy method with "Auto Read Sequencing Kit"

(Pharmacia) and "A.L.F. DNA Sequencer" (Pharmacia). In addition, the deduced amino acid sequence of "rat JTT-1 antigen" encoded by the nucleotide sequence was analyzed with gene analysis software "GENEWORKS" (IntelliGenetics). The nucleotide sequence and the deduced amino acid sequence were shown in SEQ ID NO: 4.

The amino acid sequence (composed of 200 amino acid residues) deduced from the cloned gene comprises the same amino acid sequence as the N terminal amino acid sequence determined in Example 6-(3). Considering that clone "T132A7"-introduced cells strongly react with "JTT-1 antibody," it can be concluded that clone "T132A7" comprises the cDNA encoding "rat JTT-1 antigen."

4. Computer Analysis

Hydropathy analysis of the primary structure of the deduced amino acid sequence of "JTT-1 antigen" was performed according to the method of Kite and Doolittle (Kite et al., J. Mol. Biol., 157:105-132, 1982) (FIG. 9). The results revealed that "JTT-1 antigen" is a transmembrane protein having a signal sequence at the N-terminus. In addition, the results of motif analysis revealed that "JTT-1 antigen" has two Asn-linked sugar chain binding sites in the extracellular domain, and two casein kinase phosphorylation sites and one protein kinase C phosphorylation site in the cytoplasmic domain. In FIG. 9 "CHO" means N-linked sugar chain binding site; "P", phosphorylation site; "CKII", casein kinase II; and "PKC", protein kinase C.

EXAMPLE 8

Cloning of cDNA Encoding "Human JTT-1 Antigen"

1. Preparation of a Probe

The cDNA (about 0.9 kb) encoding "rat JTT-1 antigen" was generated by digesting the clone "T132A7" obtained in Example 7 with restriction enzymes EcoRI and NotI, and separated by agarose gel electrophoresis. The separated DNA fragments were purified with "QUIAEX gel extraction kit" (QUIAGEN), and the obtained DNA fragments were labeled with $^{32}$P using "Ready-To-Go DNA labelling kit" (Pharmacia). These labeled DNA fragments were used as probes for plaque hybridization.

2. Preparation of cDNA Library 2-(1) Extraction of Poly(A)$^+$ RNA

Poly(A)$^+$ RNA was extracted from ConA-stimulated lymphoblasts (ConA blast) derived from human peripheral blood in the same manner as in Example 7-1-(1).

2-(2) Preparation of cDNA

With 5 μg of the poly(A)$^+$ RNA so prepared as a template, cDNAs were synthesized with "oligo dT primer" (Pharmacia) and "Time Saver cDNA Synthesis Kit" (Pharmacia). EcoRI adapter was then added, and size fractionation was performed with Spun Column (Pharmacia).

2-(3) Insertion into a Vector and Packaging

The cDNAs so obtained having EcoRI-ends were ligated with the vector "λZAPII" (Stratagene) digested with EcoRI. "DNA Ligation Kit" (Takara Shuzo) was used for the ligation. After in vitro packaging of the ligated DNA was performed with "GIGA PACK II GOLD" (Stratagene), E. coli XL1Blue MRF' cells (Stratagene) were transfected with the obtained phage particle to generate a cDNA library composed of plaque comprising recombinant phage.

3. Screening of cDNA Library cDNA library was screened by plaque hybridization method (Maniatis et al., Molecular Cloning, A Laboratory Manual, Cold Spring Harbor Laboratory, Cold Spring Harbor, N.Y.) with "Rapid hybridization buffer" (Amersham).

First, the cDNA library so obtained (1×10$^4$) was plated onto agar plates and the replica was produced with "Hybond-N nylon membrane" (Amersham). Plaque hybridization was performed in "Rapid hybridization buffer" (Amersham) using the replica and the $^{32}$P-labeled probe prepared in Example 8-1. First and second screenings were performed to obtain eight positive clones. Single plaques of each clone were isolated and subjected to in vivo excision in accordance with the manual (Stratagene) and seven positive clones were collected as plasmid DNA.

4. Determination of the Nucleotide Sequence

The nucleotide sequences of the seven clones were determined by dideoxy method with "Auto Read Sequencing Kit" (Pharmacia) and "A.L.F. DNA Sequencer" (Pharmacia). The seven clones comprise the same nucleotide sequence. It was found that clone "pBSh41" encodes the full length "human JTT-1 antigen." The cDNA sequence corresponding to the open reading frame (ORF) of "human JTT-1 antigen" is shown in SEQ ID NO: 1, the full length of the deduced amino acid sequence of "human JTT-1 antigen" is shown in SEQ ID NO: 2, and the nucleotide sequence comprising 5' and 3' sequences is shown in SEQ ID NO: 3 (ORF corresponds to the nucleotide residues 26 to 625). It is understood that the nucleotide sequence contained in the clone encodes the full length of "human JTT-1 antigen" because the amino acid sequence (composed of 199 amino acid residues) deduced from the nucleotide sequence shows significant homology with the amino acid sequence of "rat JTT-1 antigen" (FIG. 10). As shown in FIG. 10, the homology between the amino acid sequences of human and rat "JTT-1 antigen" is 60% or more.

E. coli DH10B (GIBCO BRL) transformed with the clone "pBSh41" has been deposited under the Budapest Treaty with international depository authority, National Institute of Bioscience and Human-Technology, Agency of Industrial Science and Technology, Ministry of International Trade and Industry, Japan (1-1-3, Higashi, Tsukuba-shi, Ibaraki, Japan) since Oct. 25, 1996 (an international deposit accession No. FERM BP-5725).

5. Structural Characteristics and Biological Function of "JTT-1 Antigen"

The results of motif search for the deduced amino acid sequence of "human JTT-1 antigen" in known human proteins revealed that "human JTT-1 antigen" has structural similarity to "CD28" and "CTLA-4," human-derived cell membrane proteins belonging to the immunoglobulin superfamily, mentioned in detail above (FIGS. 11 and 12). As mentioned above, "CD28" and "CTLA-4" are extremely important molecules regulating the activation and inhibition of T cells in immune system.

The structural similarity is as follows 1. 20 or more amino acid residues including cysteine residues are highly conserved.

2. Proline repeating sequence, "Pro-Pro-Pro (PPP)", which is essential as the ligand binding region in CD28 and CTLA-4, is conserved.

3. "Tyr-Xaa-Xaa-Met (YxxM)" (Xaa and x represents any amino acid) sequence essential as the signal transmitting region in CD28 and CTLA-4 is conserved in the cytoplasmic region.

From the fact that the same structure with the specific structure of "CD28" and "CTLA-4", which play an important role in regulation of activation of T cells that are main actor in immune mechanism, "JTT-1 antigen" of the present invention is inferred to play an important role like those molecules in regulation of activation of lymphocytes such as T cells which are main actor in immune response.

EXAMPLE 9

Cloning of cDNA Encoding "Mouse JTT-1 Antigen"

1. Preparation of a Probe

The cDNA (about 0.9 kb) encoding "rat JTT-1 antigen" was obtained by digesting the clone "T132A7," cloned in Example 7, with restriction enzymes EcoRI and NotI, and separated by agarose gel electrophoresis. The DNA fragments so separated were purified with "QUIAEX gel extraction kit" (QUIAGEN), and the DNA fragments were labeled with $^{32}$P using "Ready-To-Go DNA labelling kit" (Pharmacia). These labeled DNA fragments were used as a probe for plaque hybridization.

2. Preparation of cDNA Library 2-(1) Extraction of Poly(A)$^+$ RNA

As Example 7-1-(1), poly(A)$^+$ RNAs were extracted from ConA-stimulated lymphoblasts derived from mouse spleen (about 1×10$^6$ cells/ml).

2-(2) Preparation of cDNA Library

With 5 mg of poly(A)$^+$ RNAs prepared in the above as a template, cDNAs were synthesized with oligo dT primer (Pharmacia) and "Time Saver cDNA Synthesis Kit" (Pharmacia). After EcoRI adapter was added to the cDNA, size fractionation was performed with Spun Column (Pharmacia).

2-(3) Insertion of cDNA into a Vector and Packaging

The cDNA so obtained having EcoRI-ends was ligated with the vector 1ZAPII (Stratagene) digested with EcoRI. "DNA Ligation Kit" (Takara Shuzo) was used for the ligation. After in vitro packaging of the ligated DNA was performed with GIGA PACK II GOLD (Stratagene), *E. coli* XL1Blue MRF' cells (Stratagene) were transfected with the phage particle so obtained to generate a cDNA library composed of plaque comprising recombinant phage.

3. Screening of cDNA Library

Screening was performed by plaque hybridization method (Maniatis et al., Molecular Cloning, A Laboratory Manual, Cold Spring Harbor Laboratory, Cold Spring Harbor, N.Y.) using Rapid hybridization buffer (Amersham).

The above-obtained cDNA library (1×10$^4$) was plated onto agar plates and the replica was produced using Hybond-N nylon membrane (Amersham). Plaque hybridization was performed in Rapid hybridization buffer (Amersham) using the replica and the $^{32}$P-labeled probe prepared in Example 9-1. First and second screenings were performed to obtain five positive clones. After single plaque of each clone was isolated, in vivo excision was performed in accordance with Instruction Manual (Stratagene) and five positive clones were collected as plasmid DNA.

4. Determination of the Nucleotide Sequence

The nucleotide sequences of each of the five clones were determined by dideoxy method with "Auto Read Sequencing Kit" (Pharmacia) and "A.L.F. DNA Sequencer" (Pharmacia). The four of the five clones comprise the same nucleotide sequence. The nucleotide sequence of cDNA encoding the full length of "mouse JTT-1 antigen" and the deduced amino acid sequence are shown in SEQ ID NO: 5.

As understood from FIG. 10, "mouse JTT-1 antigen" is composed of 200 amino acid residues like "rat JTT-1 antigen." The homology among the amino acid sequences of mouse, rat, and human "JTT-1 antigens" is significant (60% or more).

5. Analysis of the Locus of "Mouse JTT-1 Antigen" Gene

The locus of the gene encoding "mouse JTT-1 antigen" was analyzed by fluorescence in situ hybridization method.

The cDNA so obtained encoding "mouse JTT-1 antigen" was labeled with $^{32}$P to prepare hybridization probes by the usual method. Using these probes, the 129 SVJ mouse genomic DNA library (Stratagene) was screened to obtain mouse genomic DNA clones comprising the exons encoding "mouse JTT-1 antigen." The structure of the genomic DNA is schematically shown in FIG. 13.

The above-obtained genomic DNA clones were labeled with digoxigenin dUTP by nick translation to prepare probes. The labeled probes were bound to cleaved mouse DNA and hybridized with normal metaphase chromosomes derived from mouse embryonic fibroblasts in the solution containing 50% formaldehyde, 10% dextran sulfate, and 2×SSC. After a slide glass for hybridization was incubated in fluorescence-labeled anti-digoxigenin antibody, specific hybridization signal was detected by staining with DAPI. In the first test, the part near the largest chromosome that was thought to be the chromosome 1, judging from the DNA size and emerged band, was specifically labeled. Based on this information, the above-described genomic DNA clone was co-hybridized with probes specific to the centromere region of the chromosome 1. As a result, the centromere region of the chromosome 1 and the regions near them were specifically labeled. Ten samples of the chromosome 1 showing the specific hybridization were analyzed, and it was revealed that the above-mentioned genomic DNA clone was located at the position of 33% of the distance from the border between heterochromatin and euchromatin to the telomere of the chromosome 1, namely, on the same band "1C3" as the loci of mouse "CD28" and "CTLA-4" genes. As the result that 80 metaphase cells were analyzed, specific labeling was identified at said position for 79 cells.

These results and the results obtained in Example 8 indicating the structural similarity of "JTT-1 antigen" to "CD28" and "CTLA-4" suggest that "JTT-1 antigen," like "CD28" and "CTLA-4," is an important molecule involved in the regulation of the transmission of costimulatory signal and/or activation of lymphocytes.

EXAMPLE 10

Cloning of cDNA Encoding a Mutant of "Rat JTT-1 antigen"

Another cDNA that is thought to encode alternative splicing variant of "rat JTT-1 antigen" cloned in Example 7 was cloned as follows.

1. Preparation of a Probe

The cDNA (about 0.9 kb) encoding "rat JTT-1 antigen" was generated by digesting the clone "T132A7," obtained in Example 7, with restriction enzymes EcoRI and NotI, and separated by agarose gel electrophoresis. The separated DNA fragments were purified with "QUIAEX gel extraction kit" (QUIAGEN), and the obtained DNA fragments were labeled with $^{32}$P using "Ready-To-Go DNA labeling kit" (Pharmacia). These labeled DNA fragments were used as probes for plaque hybridization.

2. Preparation of cDNA Library 2-(1) Extraction of Poly(A)$^+$ RNA

As in Example 7-1-(1), poly(A)$^+$ RNA was extracted from rat thymoma cell line FTL435 (about 1×10$^6$ cells/ml).

2-(2) Preparation of cDNA Library

With 5 mg of the poly(A)$^+$ RNA prepared as mentioned above as a template, cDNAs were synthesized using oligo dT primer (Pharmacia) and "Time Saver cDNA Synthesis Kit" (Pharmacia). After EcoRI adapter was added to the cDNA, size fractionation was performed with Spun Column (Pharmacia).

2-(3) Insertion of cDNA into a Vector and Packaging

The cDNA having EcoRI-end obtained above was ligated with the vector 1ZAPII (Stratagene) digested with EcoRI. "DNA Ligation Kit" (Takara Shuzo) was used for ligation. After in vitro packaging of the ligated DNA was performed with GIGA PACK II GOLD (Stratagene), E. coli XL1Blue MRF' (Stratagene) was transfected with the obtained phage particle to generate a cDNA library composed of plaque comprising recombinant phage.

3. Screening of cDNA Library

Screening was performed by plaque hybridization method (Maniatis et al., Molecular Cloning, A Laboratory Manual, Cold Spring Harbor Laboratory, Cold Spring Harbor, N.Y.) with Rapid hybridization buffer (Amersham).

The above-prepared cDNA library ($1 \times 10^4$) was plated onto agar plates and the replica was produced with Hybond-N nylon membrane (Amersham). Plaque hybridization was performed in Rapid hybridization buffer (Amersham) using the replica and the $^{32}$P-labeled probe prepared in Example 10-1. First and second screenings were performed to obtain two positive clones. After single plaque of each clone was isolated, in vivo excision was performed in accordance with Instruction Manual (Stratagene), and two positive clones were collected as plasmid DNA.

4. Determination of the Nucleotide Sequence

The nucleotide sequences of the two clones were determined by dideoxy method with "Auto Read Sequencing Kit" (Pharmacia) and A.L.F. DNA Sequencer (Pharmacia). The two clones comprise the same nucleotide sequence. The nucleotide sequence of cDNA encoding the full length of the obtained "rat JTT-1 antigen" and the deduced amino acid sequence are shown in SEQ ID NO: 6. The amino acid sequence (SEQ ID NO: 6) deduced from the obtained cDNA sequence was compared with the amino acid sequence (SEQ ID NO: 4) deduced from the obtained cDNA sequence encoding "rat JTT-1 antigen" cloned in Example 7 (FIG. 14). As shown in FIG. 14, the amino acid sequence encoded by the cDNA cloned in this test was completely the same as that encoded by the cDNA encoding "rat JTT-1 antigen" obtained in Example 7, except that (1) C-terminal three continuous amino acid residues (Met-Thr-Ser) changes into Thr-Ala-Pro, and that (2) subsequent to the Thr-Ala-Pro, 16 continuous amino acid residues (Leu-Arg-Ala-Leu-Gly-Arg-Gly-Glu-His-Ser-Ser-Cys-Gln-Asp-Arg-Asn) are added. This indicates that the cDNA cloned in this test encodes the alternative splicing variant of "rat JTT-1 antigen" obtained in Example 7.

EXAMPLE 11

Preparation of Recombinant "Human JTT-1 Antigen"-expressing Cells

The plasmid clone pBSh41 obtained in Example 8 was digested with a restriction enzyme EcoRI, and a DNA fragment comprising the cDNA encoding the full length of "human JTT-1 antigen" was excised. This DNA fragment was inserted with DNA Ligation Kit (Takara Shuzo) into a plasmid pEFneo (Proc. Natl. Acad. Sci. USA 91:158-162, 1994) treated with the same restriction enzyme EcoRI to prepare the expression vector. CHO-K1 cells (ATCC: CCL 61) were transformed with the vector by electroporation. By cultivating the cells in RPMI1640 medium containing 0.8 mg/ml Geneticin (GIBCO BRL) and 10% fetal calf serum for about two weeks, Geneticin-resistant transformants were selected.

The expression of recombinant "human JTT-1 antigen" was confirmed by Northern blotting by the usual method.

EXAMPLE 12

Preparation of Monoclonal Antibodies Against "Human JTT-1 Antigen"

The recombinant "human JTT-1 antigen"-expressing transformants prepared in Example 11 were homogenized and ultracentrifuged (100,000×g). The pellet containing the cell membrane fraction was collected and suspended in PBS. The resulting suspension comprising the cell membrane fraction was injected into the footpad of a BALB/c mouse with complete Freund's adjuvant for the first immunization (day 0). The cell membrane fraction antigen was further administered into its footpad at intervals of 7, 14, and 28 days. Two days after the last immunization, the lymph node cells was taken out. The lymph node cells and mouse myeloma cells PAI (JCR No. B0113; Res. Disclosure 217:155, 1982) were mixed at a ratio of 5:1, and fused using polyethyleneglycol 4000 (GIBCO) as a fusing agent to prepare monoclonal antibody-producing hybridomas. The hybridomas were screened by cultivating them in HAT-containing ASF104 medium (Ajinomoto) supplemented with 10% fetal calf serum and aminopterin. The culture supernatant of each hybridoma was reacted with the recombinant "human JTT-1 antigen"-expressing transformants prepared in Example 11, and the fluorescence intensity of cells stained by reacting them with FITC-labeled anti-mouse IgG (Cappel) was measured with EPICS-ELITE flow cytometer to confirm the reactivity of the monoclonal antibody generated in each culture supernatant to "human JTT-1 antigen." It has been confirmed that 10 or more kinds of hybridomas producing monoclonal antibodies reactive to "human JTT-1 antigen" were obtained.

Each of two kinds (designated clone SA12 and SG430) among these hybridomas ($10^6$ to $10^7$ cells/0.5 ml/mouse) was injected into a ICR nu/nu mouse (female, 7-8 weeks old) intraperitoneally. After 10 to 20 days, celiotomy of the mice was performed under anesthesia, and the two kinds of monoclonal antibodies (SA12 and SG430) reactive to "human JTT-1 antigen" were prepared in a large amount from the ascites fluid extracted by the usual method.

EXAMPLE 13

Effect of the Monoclonal Antibodies Against "Human JTT-1 Antigen" on Human Peripheral Blood Lymphocytes As mentioned in Example 8, it is thought that "JTT-1 antigen" can be involved in the regulation of the activation of lymphocytes in immune reaction like "CD28" and "CTLA-4." In order to prove this, the effect of the monoclonal antibodies against "human JTT-1 antigen" on human lymphocytes was analyzed in light of cell growth as an indication.

To each well of 96-well microtiter plate were added (1) either SA12 or SG430 (1 μg/ml), the monoclonal antibody against "human JTT-1 antigen" prepared in Example 12, or (2) a mixture of either monoclonal antibody SA12 or SG430 (1 μg/ml) with anti-CD3 monoclonal antibody OKT-3 (1 μg/ml, Orthodiagnostic Systems), which is used for adding the primary signal in the activation of lymphocytes. The plate was incubated at 37° C. for 1 hour to coat each well with the antibody. After the plate was washed with RPMI1640 medium, normal human peripheral blood lymphocytes ($1 \times 10^5$ cells/well) were added to each well and incubated in RPMI1640 medium containing 10% fetal calf serum for 3 days. If necessary, 1 ng/ml phorbol myristate acetate (PMA) was added. Then, [$^3$H] thymidine (3.7 μkBq/well) was added to each well, and the plate was incubated at 37° C. for 6 hours. The cells were harvested, and the amount of [$^3$H] thymidine incorporated into DNA was measured with a liquid scintillation counter (Beckman). The assay without any antibody was used as a control. The results are shown in FIG. 15.

In the assay using the plates coated with either monoclonal antibody SA12 or SG430, the number of lymphocytes increased about 10 times compared to the control. In the co-presence of OKT3, the number of lymphocytes increased about 100 times when either monoclonal antibody SA12 or SG430 was used.

These results indicate that "JTT-1 antigen" functions in the regulation of the lymphocyte activation. The fact that the cell growth rate was increased by using together with OKT3 indicates that "JTT-1 antigen" is involved in the transmission of costimulatory signal like "CD28" and "CTLA-4."

EXAMPLE 14

Effect of "JTT-2 Antibody" on Experimental Allergic Encephalomyelitis (EAE)

As above mentioned in detail, recently, many attempts to treat various autoimmune diseases (rheumatoid arthritis, multiple sclerosis, autoimmune thyroiditis, allergic contact dermatitis, chronic inflammatory dermatosis such as lichen planus, systemic lupus erythematosus, insulin dependent diabetes mellitus, psoriasis, etc.) have been made by regulating the transmission of between CD28/CTLA-4 and CD80/CD86. The effect has been already confirmed in various model animals of autoimmune diseases ((1) a model for human systemic lupus erythematosus (SLE); (2) experimental allergic encephalomyelitis (EAE), a model for multiple sclerosis (MS); (3) a model for insulin dependent diabetes mellitus (IDDM); (4) Goodpasture's nephritis model; and (5) human rheumatoid arthritis).

In order to determine whether "JTT-1 antigen" of the present invention is a molecule involved in the activation or inhibition of lymphocytes such as "CD28" and "CTLA-4," model rats for experimental allergic encephalomyelitis (EAE), a model for multiple sclerosis (MS), were produced, and the effect of the titled monoclonal antibody on "JTT-1 antigen" in the model was analyzed.

An emulsion to be used as immunogen was prepared by mixing Hartley guinea pig cerebrospinal homogenate (800 mg/ml physiological saline) with the same amount of Freund's complete adjuvant. Immunization was performed by intradermally injecting the emulsion into left and right foot pads of 15 Lewis rats (female, 6-week-old) in an amount of 0.25 ml per footpad. The administration (immunization) was adjusted so as for the dosages of the homogenate prepared to be 200 mg per rat. This immunization so induces experimental allergic encephalomyelitis (EAE).

The rats so immunized were divided into three groups of five rats each, and any one of (1) to (3) below was intravenously injected into mice of each group immediately after immunization (day 0), and 3, 6, 9, and 12 days after the immunization.

(1) Monoclonal antibody "JTT-2 antibody" against "rat JTT-1 antigen" prepared in Example 2 (dosage: 2 mg/ml PBS, 5 mg/kg)

(2) Prednisolone, steroid agent (dosage: 4 mg/ml PBS, 10 mg/kg)

(3) Control antibody non-reactive to "rat JTT-1 antigen" (dosage: 2 mg/ml PBS, 5 mg/kg)

Symptom was observed in the course of time after the immunization. After the onset of EAE had been found, the degree of the symptom was estimated by scoring the symptom based on the following criteria.

(Score 1) Disappearance of tension of a tail
(Score 2) Dragging of hind legs, and slight paralysis
(Score 3) Dragging of hind legs, and serious paralysis
(Score 4) Paralysis of the whole body, or death The results are shown in FIG. 16. In the group to which the control antibody was administered, the symptom of EAE reached the peak (maximum score) at day 11 to 15 after the immunization, and then gradually recovered. In contrast, in the "JTT-2 antibody"-administered group, the symptom of EAE at day 11 after the immunization was significantly inhibited. This inhibitory effect was significantly higher than that in the prednisolone-administred group.

These results indicate that "JTT-1 antigen" is a molecule that functions in the induction of immune response such as the lymphocyte activation induced by immunization by foreign antigens, and that the regulation of the function of "JTT-1 antigen" or its ligands can inhibit the symptom of various autoimmune diseases.

EXAMPLE 15

Effect of "JTT-2 Antibody" on Glomerulonephritis

For the same purpose as Example 14, glomerulus basement membrane (GBM) nephritis model rats were produced, and the effect of the titled monoclonal antibody on "JTT-1 antigen" in the model was analyzed.

After bovine glomerulus basement membrane (Shigei Medical Institute) digested with collagenase was diluted with physiological saline to 200 μg/ml, the dilution was mixed with Freund's complete adjuvant to prepare an emulsion to be used as immunogen. Immunization was performed by intradermally injecting the emulsion into both hind soles of 48 Wistar kyoto rats (about 200 g) under anesthesia in an amount of about 0.2 ml per footpad (dosage: about 15 Ag). This immunization so induces glomerulus basement membrane (GBM) nephritis.

The immunized rats were divided into eight groups of six rats each, and any one of (1) to (3) below was injected into rats of each group immediately after immunization (day 0), and three times a week for 5 consecutive weeks.

(1) Monoclonal antibody "JTT-2 antibody" against "rat JTT-1 antigen" prepared in Example 2 (dosage: 3 mg/kg (2 ml PBS/kg), intravenous injection)

(2) Prednisolone, steroid agent, as a positive control (suspended in 0.5% carboxymethylcellulose (CMC)) (dosage: 3 mg/kg (5 ml/kg), oral administration)

(3) 0.5% CMC as a negative control (dosage: 5 ml/kg, oral administration)

After the administration of a test substrate, sterilized water (25 ml/kg) was orally administered into each rat forcedly, and urine was collected for 5 hours from each rat which had been kept in a metabolism cage without eating and drinking. After the volume of the collected urine was measured, the urinary protein concentration was measured using Tonein TP-II (Otuka), and the urinary excretion of protein per five hours was calculated (unit: mg protein/5 hours). The above-mentioned urinary collection and urinary protein measurement were performed in the same manner at 1, 2, 3, and 4 weeks after the immunization (day 0).

The results are shown in FIG. 17. Compared to the control group, the urinary excretion of protein at 3 weeks after the immunization was significantly reduced in the "JTT-2 antibody"-administered group.

These results indicate that "JTT-1 antigen" is a molecule that induces immune response such as the lymphocyte activation induced by immunization by foreign antigens, and that the regulation of the function of "JTT-1 antigen" or its ligands can inhibit the symptom of various autoimmune diseases.

EXAMPLE 16

Preparation of the Fusion Protein Between "JTT-1 Antigen" and IgFc

As mentioned in Examples 8, and 13 to 15, "JTT-1 antigen" of the present invention is thought to be a molecule such as "CD28" and "CTLA-4" involved in the transmission of costimulatory signal involved in the regulation of the activation of lymphocytes. In addition, as mentioned in Example 14, a fusion protein (CTLA-4-IgFc) composed of the extracellular domain of "CTLA-4" and the Fc region of human immunoglobulin IgG1 reportedly has therapeutic effects on various autoimmune diseases. In this Example, a fusion protein composed of the extracellular region of "JTT-1 antigen" and human IgGFc was prepared as follows in order to examine whether soluble JTT-1 antigen, like CTLA-4-IgFc, could be applied to therapy of various autoimmune diseases.

(1) Preparation of the Fusion Protein Between "Rat JTT-1 Antigen" and Human IgG1-Fc (rJTT-1-IgFc)

In order to amplify the cDNA encoding the extracellular region of "rat JTT-1 antigen" by PCR, 5' primer having XhoI restriction site (5'-CTGCTCGAGATGAAGCCCTACT-TCTCG-3', SEQ ID NO: 7) and 3' primer having BamHI restriction site (5'-ACCCTACGGGTAACGGATCCT-TCAGCTGGCAA-3', SEQ ID NO:8) at their terminus were designed and synthesized. Using cDNA clone "T132A7" obtained in Example 7 encoding the full length of "rat JTT-1 antigen" as a template, PCR was performed with the primers to prepare the cDNA comprising the cDNA encoding the extracellular region of "rat JTT-1 antigen" having XhoI and BamHI restriction sites at its both ends. The PCR products so obtained were digested with XhoI and BamHI and separated by agarose gel electrophoresis to isolate an about 450-bp band predicted to be the cDNA fragment encoding a desired extracellular region. The isolated cDNA fragment was subcloned into pBluescript II SK (+) (Stratagene) cleaved with XhoI and BamHI. Sequence analysis with an automated fluorescence DNA sequencer (Applied Biosystems) revealed that the cDNA fragment comprises the region encoding amino acid sequence corresponding to the amino acid residues 1 to 141 of "rat JTT-1 antigen" (SEQ ID NO: 4).

On the other hand, the DNA encoding the Fc of human IgG1 as the fusion partner was cut out as an about 1.3 kb BamHI-XbaI DNA fragment by digesting the plasmid (see Cell 61:1303-1313, 1990). Prepared by B. Seed et al. (Massachusetts General Hospital)) with BamHI and XbaI. This fragment comprises exons encoding human IgG1 hinge region, $C\gamma_1 2$, and $C\gamma_1 3$.

The XhoI-BamHI fragment encoding the extracellular region of "rat JTT-1 antigen," and BamHI-XbaI fragment comprising exons encoding the Fc of human IgG1 ("IgFc"), both prepared as mentioned above, were subcloned into pBluescript II SK (+) (Stratagene) cleaved with XhoI and XbaI.

Then, the plasmid was digested with XhoI and XbaI, and an about 1.8 kb DNA fragment comprising the fusion DNA comprising the extracellular region of "rat JTT-1 antigen" and human IgFc was cut out. This fusion DNA fragment was inserted into the XhoI and XbaI sites of the expression vector pME18S (Medical Immunology 20:27-32, 1990; Experimental Medicine: SUPPLEMENT, "Handbook of Genetic Engineering,"Yodosha, pp. 101-107, 1992) with T4 DNA ligase to construct plasmid prJTT-1-IgFc.

HEK293 cells (ATCC CRL1573) subconfluently cultivated as monolayer in DMEM medium containing 10% fetal calf serum and ampicillin were transformed with prJTT-1-IgFc by electroporation to obtain transformants.

The transformants were cultured in serum-free ASF104 medium for 72 hours to express rJTT-1-IgFc.

Using a Protein G Sepharose affinity column (Pharmacia), rJTT-1-IgFc was purified as follows.

The supernatant obtained by centrifuging the culture medium mentioned above was loaded onto Protein G Sepharose affinity column previously equilibrated with binding buffer. After the column was washed with binding buffer, elution was performed with elution buffer. The eluate was collected and dialyzed against phosphate buffer with exchanging the external solution twice or more to obtain pure rJTT-1-IgFc.

The result of affinity chromatography is shown in FIG. 18, and the result of SDS-PAGE of the pure rJTT-1-IgFc so obtained in FIG. 19.

(2) Preparation of the Fusion Protein Between "Human JTT-1 Antigen" and Human IgG1-Fc (hJTT-1-IgFc)

hJTT-1-IgFc was prepared as mentioned above in (1), except for cDNA used as templates and primers for PCR. In this test, the clone "pBSh41" comprising the cDNA encoding the full length "human JTT-1 antigen" prepared in Example 8 was used as a template, and 5'-TAACTGTTTCTCGAGAA-CATGAAGTCAGGC-3' (SEQ ID NO: 9) and 5'-ATC-CTATGGGTAACGGATCCTTCAGCTGGC-3' (SEQ ID NO: 10) were used as primers.

The result of affinity chromatography is shown in FIG. 20, and the result of SDS-PAGE of the pure hJTT-1-IgFc so obtained in FIG. 21.

EXAMPLE 17

Preparation of a Transgenic Mouse in which cDNA Encoding "Rat JTT-1 Antigen" has been Integrated The cDNA encoding the full length of "rat JTT-1 antigen" obtained in Example 7 was inserted into the expression vector pCAGGS (Gene 108:193-200, 1991) having chicken β actin promoter using DNA Blunting Kit (Takara) to obtain plasmid, prJTT-1. In order to prepare a transgenic mouse, prJTT-1 was linearized by restriction enzyme treatment.

A female ICR mouse having a vaginal plug, obtained by mating a white ICR mouse (Nihon LSC) with a male vasoligated white ICR mouse (Nihon SLC), was used as a foster mother mouse. A mouse for obtaining fertilized eggs for introducing "rat JTT-1 antigen" gene thereinto was prepared by mating a female BDF-1 mouse (Nihon SLC) that had been made to superovulate by administered PEAMEX (5 units, Sankyo Zoki) and Pregnil (5 units, Organon) with a male BDF-1 male (Nihon SLC). After mating, the oviduct was excised from the female BDF-1 mouse, and only fertilized eggs were obtained by hyaluronidase treatment and stored in a medium.

The "rat JTT-1 antigen" gene was introduced into the fertilized egg under microscopy using a manipulator according to the usual method. The fertilized egg was fixed with a retaining needle. A solution containing the above-mentioned linearized gene encoding "rat JTT-1 antigen," which was diluted with Tris-EDTA buffer, was microinjected into the male pronucleus of the fertilized eggs with a DNA introduction needle at 37° C.

After gene introduction, only fertilized eggs keeping normal state were selected, and then, the fertilized egg so selected in which the "rat JTT-1 antigen" genes have been introduced was inserted into the ovarian fimbria in the ovary of a foster mother mouse (white ICR mouse).

The tail of a progeny mouse (founder mouse) born from the foster mother mouse was cut off and the genomic gene was collected from it. It was confirmed by PCR that the "rat JTT-1 antigen" gene was integrated into the mouse genome. Then, heterozygous transgenic mice highly expressing "rat JTT-1 antigen" were prepared by mating this founder mouse with a normal mouse. Homozygous transgenic mice can be prepared by mating the heterozygous mice with each other.

The microinjected construct comprising the "rat JTT-1 antigen" gene is schematically shown in FIG. 22.

EXAMPLE 18

Preparation of a Knockout Mouse Whose Endogenous Gene Encoding "Mouse JTT-1 Antigen" has been Inactivated (1) Construction of a Targeting Vector A targeting vector for inactivating (knocking out) the endogenous gene encoding "mouse JTT-1 antigen" through homologous recombination (Nikkei Science, pp. 52-62, May 1994) was prepared as follows.

The PstI-HindIII fragment ("homologous DNA (1)") obtained by digesting the mouse genomic DNA clone comprising the region encoding "mouse JTT-1 antigen" cloned in Example 9-5 with PstI and HindIII was subcloned into pGEM-3 (Promega). Then, pGEM-3 was linearized with XhoI, and neomycin resistance gene ("neo") excised from pMC1-neo-polyA (Stratagene) by treating it with XhoI and SalI was inserted at the upstream of the "homologous DNA" (1) and then ligated them. The above-mentioned mouse genomic DNA clone was digested with XhoI and NotI to cut off an about 5.5 kb gene ("homologous DNA (2)") located upstream of above-mentioned "homologous DNA (1)." Separately, the above-mentioned pGEM-3 into which "neo-homologous DNA (1)" has been inserted was digested with XhoI and HindIII to cut off "neo-homologous DNA (1)." "Homologous DNA (2)" and "neo-homologous DNA (1)" thus obtained were subcloned into pSEAP2-CONT (Clontech) linearized with NotI and HindIII.

After the obtained plasmid, in which "homologous (2)-neo-homologous (1)" has been inserted, was digested and linearized at the downstream of "homologous DNA (1)" with NruI, thymidine kinase gene ("TK") obtained by digesting pMC1-TK (Stratagene) with PvuII was inserted at the downstream of "homologous DNA (1)" to obtain a targeting vector, in which "homologous DNA (2)-neo-homologous (1)" was inserted.

(2) Introduction of the Targeting Vector into ES Cells

Mouse embryonic stem cells (Nature 362:255-258, 1993; Nature 326:292-295, 1987) cultured in DMEM medium containing 15% fetal calf serum were treated with trypsin to be single cells, and the cells were washed three times, followed by adding phosphate buffer thereto to adjust $1 \times 10^7$ cells/ml. The targeting vector mentioned above (25 μg per 1 ml of the cell suspension) was added to the cell suspension, and electric pulse was delivered once under the condition of 350 V/cm (25 μF). Then, $1 \times 10^7$ of ES cells were plated on a 10-cm dish and cultivated in maintenance medium for a day, and the medium was changed to selection medium (containing 250 μg/ml G418 and 2 μM ganciclovir). The cells were cultivated with the medium changed every two days. At the tenth day from the introduction of the targeting vector, 573 neomycin-resistant ES cell clones were obtained under microscopy with a micropipet. Each of the ES cell clones so obtained were cultivated independently on a 24-well plate coated by Feeder cells to obtain 768 neomycin-resistant ES cell replicas.

(3) Screening of Knockout ES Cells

It was confirmed by PCR whether the endogenous gene encoding "mouse JTT-1 antigen" was disrupted (knocked out) through homologous recombination in each of the neomycin-resistant ES cells.

For PCR, (1) primers designed and synthesized based on the sequence of above-mentioned neomycin-resistant gene ("neo") (5'-CGTGATATTGCTGAAGAGCTTGGCGGC-GAATGGGC-3', SEQ ID NO: 11) and (2) primers designed and synthesized based on the sequence of above-mentioned "homologous DNA (1)" (5'-CATTCAAGTTTCAGGGAAC-TAGTCCATGCGTTTC-3', SEQ ID NO: 12) were used.

Each genomic DNA was extracted from each of the neomycin-resistant ES cell and PCRs were performed using the primers with the genomic DNA as a template. PCR was performed 1 cycle of reaction at 94° C. for 3 minutes, 30 cycles of reaction at 94° C. for 1 minute, at 60° C. for 1 minute, and at 72° C. for 3.5 minutes, and 1 cycle of reaction at 72° C. for 10 minutes, and the resulting products were stored at 4° C. When a fragment less than about 4 kb was amplified by this PCR, it could be judged that the endogenous gene encoding "mouse JTT-1 antigen" was disrupted (knocked out) through homologous recombination in the ES cell clone.

A desired PCR product was obtained from three of 768 ES cell clones tested. Genomic southern blottings were performed for these three clones for further screening and confirmation. After genomic DNA was extracted from the three clones and digested with restriction enzyme BamHI, the digested products were subjected to agarose gel electrophoresis. The resulting DNAs were transferred to nylon membrane, and hybridization was performed with a probe prepared from the genomic DNA sequence comprising "mouse JTT-1." The probe was designed based on the sequence outside the site where homologous recombination occurred, which enables to distinguish mutant type genome from normal type genome in size.

As a result, two bands corresponding to mutant type and normal type were observed in one of the three clones. This ES cell clone was used for the preparation of a knockout mouse described below.

(4) Preparation of a Knockout Mouse

The above-obtained ES cells (15 ES cells per blastocyst) whose endogenous gene encoding "mouse JTT-1 antigen" has been inactivated (knocked out) through homologous recombination were microinjected into blastocysts to, which were obtained by mating a female C57BL6 mouse (Nihon Charles River) with male one. Immediately after the microinjection, the blastocysts (about 10 blastocysts per one side of the uterus) were transplanted in the uterus of a foster mother ICR mouse (CLEA Japan), which was 2.5 day-mouse from pseudopregnant treatment. As a result, 38 progeny mice in total were obtained, and 18 out of them were desired chimeric mice. Eleven (11) out of the chimeric mice were the chimeric-mouse in which the contribution to hair color was 80% or more.

The chimeric mice so obtained were then mated with a normal C57BL6 mice to obtain agouti mice whose color is derived from hair color gene of the ES cells.

EXAMPLE 19

Preparation of Pharmaceutical Composition Comprising Antibody

Each of the monoclonal antibody (50-150 µg/ml), "JTT-1 antibody" and "JTT-2 antibody" against "rat JTT-1 antigen," prepared in Example 1, and monoclonal antibodies, "SA12" and "SG430" against "human JTT-1 antigen," prepared in Example 12, was added to injectable distilled water (10 ml) to prepare injection.

INDUSTRIAL APPLICABILITY

Novel cell surface molecules (called "JTT-1 antigen") of the present invention derived from mammals such as human, mouse, and rat are characterized as follows.
(1) "JTT-1 antigen" had the following similarity with "CD28," a cell surface molecule on lymphocytes such as T cells, which transmits costimulatory signal important for T cell activation through cell adhesion, and "CTLA-4," a cell surface molecule on lymphocytes such as T cells, which regulates the function of activated lymphocytes such as activated T cells, cooperating with the signal.
  (i) 20 or more amino acid residues including cysteine residues are highly conserved;
  (ii) Proline repeating sequence, "Pro-Pro-Pro (PPP)," which is essential as the ligand binding region, is conserved in the extracellular region;
  (iii) "Tyr-Xaa-Xaa-Met (YxxM)" (Xaa and x represents any amino acid) sequence essential as the signal transmitting region is conserved in the cytoplasmic region; and
  (iv) The locus of the gene encoding "mouse JTT-1 antigen" on mouse chromosome is "1C3", like "CD28" and "CTLA-4."
(2) "JTT-1 antigen" can mediate cell adhesion of thymocytes, lymphoblasts stimulated with mitogen such as ConA, thymomas, like "CD28" and "CTLA-4" that mediate cell adhesion.
(3) "JTT-1 antigen" is strongly expressed, at least, in thymocytes, lymphoblast cells stimulated with mitogen such as ConA (activated T lymphoblast cells and activated B lymphoblast cells, etc.), peripheral blood lymphocytes, and thymomas.
(4) The antibody against "JTT-1 antigen" significantly proliferates human peripheral blood lymphocytes, and the proliferation is more enhanced in the presence of a monoclonal antibody against CD3 constituting TcR/CD3 complex on T cells that receive the primary signal essential for T cell activation from antigen-presenting cells.
(5) The administration of the antibody against "JTT-1 antigen" significantly inhibits the symptom of experimental allergic encephalomyelitis (EAE).
(6) The administration of the antibody against "JTT-1 antigen" to a model rat for glomerulus basement membrane (GBM) nephritis significantly inhibits the symptom of this disease. "JTT-1 antigen" of the present invention is, like "CD28" and "CTLA-4," thought to be a molecule transmitting the secondary signal (costimulatory signal) essential for the activation of lymphocytes such as T cells, and regulating the function of activated lymphocytes such as activated T cells, cooperating with the signal.

Therefore, polypeptides constituting such cell surface molecules, its polypeptide fragment, and fusion polypeptides therefrom, and antibodies thereto of the present invention can provide extremely useful pharmaceuticals for therapy or prevention of various autoimmune diseases, allergic diseases, or inflammatory diseases, specifically, rheumatoid arthritis, multiple sclerosis, autoimmune thyroiditis, allergic contact dermatitis, chronic inflammatory dermatosis such as lichen planus, systemic lupus erythematosus, insulin dependent diabetes mellitus, and psoriasis, caused by the activation of lymphocytes such as T cells and the abnormality of regulation of activated lymphocyte functions.

Similarly, the genes encoding polypeptides or polypeptide fragments of the present invention can be used in not only gene therapy of various diseases as mentioned above but also preparation of antisense pharmaceuticals.

Among the antibodies of the present invention, human monoclonal antibodies and their pharmaceutical compositions have dramatically increased pharmaceutical value of antibody drugs because they have no antigenicity against human, which has been a serious problem (side effect) of antibody pharmaceuticals containing nonhuman mammal-derived antibodies such as mouse-derived antibodies.

The genes (DNA), polypeptides, polypeptide fragments and antibodies of the present invention are useful not only as pharmaceuticals but also as reagents for searching molecules (ligands) interacting with the cell surface molecules of the present invention, clarifying the function of the ligand, and developing drugs targeting the ligands.

Furthermore, the transgenic mouse of the present invention is extremely useful not only as a model animal for studying physiological function of "JTT-1 antigen" that is a cell surface molecule of the present invention but also as a tool for screening various drugs (low molecular weight compounds, antibodies, antisense substances, polypeptides, etc.) having activity regulating (inhibition, suppression, activation, stimulation, etc.) the function of "JTT-1 antigen." Specifically, such test substances can be administered to the transgenic mouse to measure and analyze various physiological, biological, or pharmacological parameters generated in the mouse, thereby assessing activity of the administered test substances.

In addition, the knockout mouse of the present invention can clarify the function of the cell surface molecules of the present invention by analyzing the characteristics of the mouse from various viewpoints (physiological, biological, pharmacological, pathological, and genetic viewpoints).

What is claimed is:

1. A purified chimeric, humanized or human monoclonal antibody that binds to a polypeptide consisting of SEQ ID NO:2, wherein the antibody binds to the polypeptide when expressed on the surface of a cell.

2. The antibody of claim 1, wherein the antibody is chimeric.

3. The antibody of claim 1, wherein the antibody is humanized.

4. The antibody of claim 1, wherein the antibody is a human antibody.

5. The antibody of claim 2, wherein the antibody has an IgG isotype.

6. The antibody of claim 3, wherein the antibody has an IgG isotype.

7. The antibody of claim 4, wherein the antibody has an IgG isotype.

8. A pharmaceutical composition comprising the antibody of claim 2 and a pharmaceutically acceptable carrier.

9. A pharmaceutical composition comprising the antibody of claim 3 and a pharmaceutically acceptable carrier.

10. A pharmaceutical composition comprising the antibody of claim 4 and a pharmaceutically acceptable carrier.

11. A pharmaceutical composition comprising the antibody of claim 5 and a pharmaceutically acceptable carrier.

12. A pharmaceutical composition comprising the antibody of claim 6 and a pharmaceutically acceptable carrier.

13. A pharmaceutical composition comprising the antibody of claim 7 and a pharmaceutically acceptable carrier.

14. An isolated cell that produces the antibody of claim 5.

15. An isolated cell that produces the antibody of claim 6.

16. An isolated cell that produces the antibody of claim 7.

17. A purified chimeric, humanized or human monoclonal antibody or a portion thereof that binds to a polypeptide consisting of SEQ ID NO:2, wherein the antibody or portion thereof binds to the polypeptide when expressed on the surface of a cell.

18. The antibody or portion thereof of claim 17, wherein the antibody is chimeric.

19. The antibody or portion thereof of claim 17, wherein the antibody is humanized.

20. The antibody or portion thereof of claim 17, wherein the antibody is a human antibody.

21. A pharmaceutical composition comprising the antibody or portion thereof of claim 18 and a pharmaceutically acceptable carrier.

22. A pharmaceutical composition comprising the antibody or portion thereof of claim 19 and a pharmaceutically acceptable carrier.

23. A pharmaceutical composition comprising the antibody or portion thereof of claim 20 and a pharmaceutically acceptable carrier.

24. An isolated cell that produces the antibody or portion thereof of claim 18.

25. An isolated cell that produces the antibody or portion thereof of claim 19.

26. An isolated cell that produces the antibody or portion thereof of claim 20.

* * * * *